United States Patent
Quattropani et al.

(10) Patent No.: US 12,195,455 B2
(45) Date of Patent: Jan. 14, 2025

(54) SUCCINATE AND FUMARATE ACID ADDITION SALTS OF PIPERAZINE DERIVATIVES

(71) Applicant: Asceneuron SA, Lausanne (CH)

(72) Inventors: Anna Quattropani, Rolle (CH);
Santosh S. Kulkarni, Bangalore (IN);
Awadut Gajendra Giri, Bangalore (IN); Robert Hett, Muttenz (CH);
David Malcolm Crowe, Reading (GB)

(73) Assignee: Asceneuron SA, Lausanne (CH)

( * ) Notice: Subject to any disclaimer, the term of this patent is extended or adjusted under 35 U.S.C. 154(b) by 757 days.

(21) Appl. No.: 17/269,811

(22) PCT Filed: Aug. 22, 2019

(86) PCT No.: PCT/EP2019/072474
§ 371 (c)(1),
(2) Date: Feb. 19, 2021

(87) PCT Pub. No.: WO2020/039030
PCT Pub. Date: Feb. 27, 2020

(65) Prior Publication Data
US 2021/0198250 A1 Jul. 1, 2021

(30) Foreign Application Priority Data
Aug. 22, 2018 (EP) ..................... 18190155

(51) Int. Cl.
*C07D 417/12* (2006.01)

(52) U.S. Cl.
CPC ................. *C07D 417/12* (2013.01)

(58) Field of Classification Search
CPC .. C07D 417/12; C07D 277/62; C07D 277/64; A61P 25/28; A61P 3/10; A61P 9/10; A61P 35/00; A61K 31/506
See application file for complete search history.

(56) References Cited

U.S. PATENT DOCUMENTS

| | | | |
|---|---|---|---|
| 3,299,067 A | 1/1967 | Gilbert et al. | |
| 3,457,263 A | 7/1969 | Regnier et al. | |
| 3,485,757 A | 12/1969 | Shapiro | |
| 3,489,757 A | 1/1970 | Koppe et al. | |
| 4,600,025 A | 7/1986 | Grigg et al. | |
| 5,935,974 A | 8/1999 | Rae et al. | |
| 7,582,769 B2 | 9/2009 | Murray et al. | |
| 7,666,875 B2 | 2/2010 | Gallagher, Jr. et al. | |
| 8,008,326 B2 | 8/2011 | Borza et al. | |
| 8,952,166 B2 | 2/2015 | Ding et al. | |
| 9,120,781 B2 | 9/2015 | Li et al. | |
| 10,336,775 B2 | 7/2019 | Quattropani et al. | |
| 10,344,021 B2 | 7/2019 | Quattropani et al. | |
| 10,556,902 B2 | 2/2020 | Quattropani et al. | |
| 10,696,668 B2 | 6/2020 | Quattropani et al. | |
| 10,995,090 B2 | 5/2021 | Quattropani et al. | |
| 11,046,712 B2 | 6/2021 | Quattropani et al. | |
| 11,213,525 B2 | 1/2022 | Quattropani et al. | |
| 11,261,183 B2 * | 3/2022 | Quattropani | A61K 31/496 |
| 11,591,327 B2 | 2/2023 | Quattropani et al. | |
| 11,612,599 B2 | 3/2023 | Quattropani et al. | |
| 11,731,972 B2 | 8/2023 | Quattropani et al. | |
| 11,795,165 B2 | 10/2023 | Quattropani et al. | |
| 12,016,852 B2 | 6/2024 | Quattropani et al. | |
| 2004/0106645 A1 | 6/2004 | Blackburn et al. | |
| 2006/0287340 A1 | 12/2006 | Moriya et al. | |
| 2007/0027328 A1 | 2/2007 | Aronhime et al. | |
| 2008/0300276 A1 | 12/2008 | Borza et al. | |
| 2009/0012078 A1 | 1/2009 | Andrews et al. | |
| 2009/0163545 A1 | 6/2009 | Goldfarb | |
| 2010/0022517 A1 | 1/2010 | Richards et al. | |
| 2011/0053982 A1 | 3/2011 | Fay et al. | |
| 2011/0060012 A1 | 3/2011 | Meyers et al. | |
| 2011/0060019 A1 | 3/2011 | Murray et al. | |

(Continued)

FOREIGN PATENT DOCUMENTS

| CN | 1791594 A | 6/2006 |
|---|---|---|
| CN | 103435606 | 12/2013 |

(Continued)

OTHER PUBLICATIONS

Berge et al. Pharmaceutical Salts, Journal of Pharmaceutical Sciences, 66, p. 1-19. (Year: 1977).*
Bastin et al. Salt Selection and Optimisation Procedures for Pharmaceutical New Chemical Entities (Organic Process Research & Development, 4, p. 427-435). (Year: 2000).*
Smith, P.W. et al "New spiropiperidines as potent and selective non-peptide tachykinin NK₂ receptor antagonists", J. Med. Chem., vol. 38, pp. 3772-3779, 1995.
"Acute Leukemia", Merck Manual (Online Edition), Hematology and Oncology, 6 pages, pp. 1-6, 2013.
Damasio, "Alzheimer's Disease and related dementias", Cecil Textbook of Medicine, 20th Edition, vol. 2, Edited by Bennett and Plum, pp. 1992-1996, 1996.

(Continued)

*Primary Examiner* — Matthew P Coughlin
*Assistant Examiner* — Meghan C Heasley
(74) *Attorney, Agent, or Firm* — COOLEY LLP

(57) ABSTRACT

The invention relates to succinic acid addition salts or fumaric acid addition salts of piperazine derivatives of formula (I), as well as solid forms, such as polymorphic forms, thereof, which are useful as pharmaceutical ingredients and, in particular, as glycosidase inhibitors.

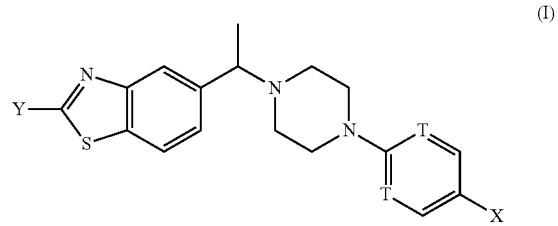

2 Claims, 12 Drawing Sheets

(56) References Cited

U.S. PATENT DOCUMENTS

| | | |
|---|---|---|
| 2012/0208808 A1 | 8/2012 | Buchstaller et al. |
| 2016/0031871 A1 | 2/2016 | Yu et al. |
| 2020/0002326 A1 | 1/2020 | Quattropani et al. |
| 2020/0385375 A1 | 12/2020 | Quattropani et al. |
| 2021/0077488 A1 | 3/2021 | Quattropani et al. |
| 2021/0186958 A1 | 6/2021 | Quattropani et al. |
| 2021/0206766 A1 | 7/2021 | Quattropani et al. |
| 2021/0213005 A1 | 7/2021 | Quattropani et al. |
| 2022/0143042 A1 | 5/2022 | Quattropani et al. |
| 2022/0177470 A1 | 6/2022 | Quattropani et al. |
| 2022/0380358 A1 | 12/2022 | Quattropani et al. |
| 2022/0411440 A1 | 12/2022 | Quattropani et al. |
| 2023/0120169 A1 | 4/2023 | Quattropani et al. |

FOREIGN PATENT DOCUMENTS

| | | | |
|---|---|---|---|
| EP | 2301936 | 3/2011 | |
| EP | 2687507 | 1/2014 | |
| FR | 1311316 | 12/1962 | |
| JP | 2010/270034 | 12/2010 | |
| WO | WO1993/021181 | 10/1993 | |
| WO | WO1997/043279 | 11/1997 | |
| WO | WO1998/046590 | 10/1998 | |
| WO | WO99/21850 | 5/1999 | |
| WO | WO02/094799 | 11/2002 | |
| WO | WO2003/092678 | 11/2003 | |
| WO | WO2004/002481 | 1/2004 | |
| WO | WO2004/005293 | 1/2004 | |
| WO | WO2004/022558 | 3/2004 | |
| WO | WO2004/094380 | 11/2004 | |
| WO | WO2005/110982 | 11/2005 | |
| WO | WO2006/092049 | 9/2006 | |
| WO | WO-2007008541 A2 | 1/2007 | |
| WO | WO2007/115077 | 10/2007 | |
| WO | WO2007/135398 | 11/2007 | |
| WO | WO2007/146122 | 12/2007 | |
| WO | WO2008/012623 | 1/2008 | |
| WO | WO2008/025170 | 3/2008 | |
| WO | WO2009/011904 | 1/2009 | |
| WO | WO2009/053373 | 4/2009 | |
| WO | WO2009/131926 | 10/2009 | |
| WO | WO2010/018868 | 2/2010 | |
| WO | WO2010/021381 | 2/2010 | |
| WO | WO2010/022517 | 3/2010 | |
| WO | WO2010/026989 | 3/2010 | |
| WO | WO2010/089127 | 8/2010 | |
| WO | WO2010/101949 | 9/2010 | |
| WO | WO2010/108115 | 9/2010 | |
| WO | WO2010/108268 | 9/2010 | |
| WO | WO2010/151318 | 12/2010 | |
| WO | WO2011/140640 | 11/2011 | |
| WO | WO2012/037298 | 3/2012 | |
| WO | WO2012/061927 | 5/2012 | |
| WO | WO2012/062157 | 5/2012 | |
| WO | WO2012/062759 | 5/2012 | |
| WO | WO2012/083435 | 6/2012 | |
| WO | WO2012/117219 | 9/2012 | |
| WO | WO2013/028715 | 2/2013 | |
| WO | WO2013/066729 | 5/2013 | |
| WO | WO2014/023723 | 2/2014 | |
| WO | WO2014/032187 | 3/2014 | |
| WO | WO2014/159234 | 10/2014 | |
| WO | WO2015/083028 | 6/2015 | |
| WO | WO2015/128333 | 9/2015 | |
| WO | WO2015/164508 | 10/2015 | |
| WO | WO2016/030443 | 3/2016 | |
| WO | WO2017/001660 | 1/2017 | |
| WO | WO2017/076900 | 5/2017 | |
| WO | WO2017/087858 | 5/2017 | |
| WO | WO2017/087863 | 5/2017 | |
| WO | WO2017/091818 | 6/2017 | |
| WO | WO2017/106254 | 6/2017 | |
| WO | WO2017/144633 | 8/2017 | |
| WO | WO2017/144635 | 8/2017 | |
| WO | WO2017/144637 | 8/2017 | |
| WO | WO2017/144639 | 8/2017 | |
| WO | WO-2017144639 A1 * | 8/2017 | ........... A61K 31/496 |
| WO | WO 2017/223243 | 12/2017 | |
| WO | WO2018/026371 | 2/2018 | |
| WO | WO2018/109198 | 6/2018 | |
| WO | WO2018/109202 | 6/2018 | |
| WO | WO2018/140299 | 8/2018 | |
| WO | WO2018/141984 | 8/2018 | |
| WO | WO2018/153507 | 8/2018 | |
| WO | WO2018/153508 | 8/2018 | |
| WO | WO2018/154133 | 8/2018 | |
| WO | WO-2018153508 A2 * | 8/2018 | ........... A61K 31/496 |
| WO | WO2018/217558 | 11/2018 | |
| WO | WO2020/039027 | 2/2020 | |
| WO | WO2020/039028 | 2/2020 | |
| WO | WO2020/039029 | 2/2020 | |
| WO | WO2020/169804 | 2/2020 | |

OTHER PUBLICATIONS

Gura, "Cancer Models: Systems for identifying new drugs are often faulty", Science, vol. 278, pp. 1041-1042, 1997 (5 pages).

Johnson et al., "Relationships between drug activity in NCI preclinical in vitro and in vivo models and early clinical trials", British Journal of Cancer, vol. 84, No. 10, pp. 1424-1431, 2001.

Layzer, "Degenerative diseases of the nervous system", Cecil Textbook of Medicine, 20th Edition, Section Five, vol. 2, Edited by Bennett and Plum, pp. 2050-2057, 1996.

Pearce et al. "Failure modes in anticancer drug discovery and development", Cancer Drug Design and Discovery Edited by Stephen Neidle, Chapter 18, pp. 424-435, 2008.

Simone "Oncology: Introduction", Cecil Textbook of Medicine, 20th Edition, vol. 1, Edited by Bennett and Plum, pp. 1004-1010, 1996.

Abdel-Magid, A. F. et al. "Reductive Amination of Aldehydes and Ketones with Sodium Triacetoxyborohydride. Studies on Direct and Indirect Reductive Amination Procedures" J. Org. Chem., (1996), 61, pp. 3849-3862.

Albertson, N. F. "Alkylation with Non-ketonic Mannich Bases. Aminothiazoles and Pyrrole" J. Am. Chem. Soc., 1948, 70(2), 669-670.

Andres, J. I. et al. "Synthesis, Evaluation, and Radiolabeling of New Potent Positive Allosteric Modulators of the Metabotropic Glutamate Receptor 2 as Potential Tracers for Positron Emission Tomography Imaging" J. Med. Chem., (2012), 55, pp. 8685-8699.

Ansari et al. "The Role of Insulin Resistance and Protein O-GlcNAcylation in Neurodegeneration", Frontiers in Neuroscience, 2019, vol. 13, Article 473, 9 pages.

Aitipamula, S. et al. "Polymorphs, Salts, and Cocrystals: What's in a Name?", Crystal Growth & Design, 12(5), 2012, p. 2147-2152.

Apsunde, T.D. et al. "Microwave-Assisted Iridium-Catalyzed Synthesis of Nicotine and Anabasine Derivatives", Synthesis, vol. 45, No. 15, 2013, pp. 2120-2124.

Aube, J. et al. "Intramolecular Schmidt reaction of alkyl azides", J. Am. Chem. Soc. 1991, vol. 113, No. 23, p. 8965-8966.

Augustine, J. K. et al. "Propylphosphonic anhydride (T3P®): an efficient reagent for the one-pot synthesis of 1,2,4-oxadiazoles, 1,3,4-oxadiazoles, and 1,3,4-thiadiazoles" Tetrahedron, (2009), 65, pp. 9989-9996.

Bastin, R. J. et al. "Salt Selection and Optimisation Procedures for Pharmaceutical New Chemical Entities", Organic Process Research & Development, 2000, 4, 427-435.

Berge, S. M. et al. "Pharmaceutical Salts", Journal of Pharmaceutical Sciences, 1977, 66(1), 1-19.

Biscoe, M. R. et al. "A New Class of Easily Activated Palladium Precatalysts for Facile C-N Cross-Coupling Reactions and Low Temperature Oxidative Addition of Aryl Chlorides", J. Am. Chem. Soc., 2008, 130, 6686-6687.

Bohnert, T. et al. "Plasma Protein Binding: From Discovery to Development", J. Pharmaceutical Sciences, 2013, 102, 2953-2994.

Bras, N. F. et al. "Glycosidase inhibitors: a patent review (2008-2013)" Expert Opinion on Therapeutic Patents, vol. 24, No. 8, 2014, pp. 857-874.

(56) References Cited

OTHER PUBLICATIONS

Bundgaard, H. "Design and Application of Prodrugs", from a Textbook of Drug Design and Development Chapter 5, Harwood Academic Publishers, 1991, 113-191.

Bundgaard, H. "Design of prodrugs: Bioreversible derivatives for various functional groups and chemical entities", Design of Prodrugs, (1985), 1 page.

Calcagno, A. M. "Comparison of Drug Transporter Levels in Normal Colon, Colon Cancer, and Caco-2 Cells: Impact on Drug Disposition and Discovery", Mol. Pharm., 2006, 3(1), 87-93.

CAS Registry (Online) Nos. 948053-91-6; 540512-02-5; 697229-62-2; 346662-52-0; 345992-64-5 (STN database summary sheets) Sep. 26, 2007.

"Chemical Encyclopedia", vol. 4, pp. 990-993, 1988. (Machine translation attached).

Chen, Y. et al. "Discovery of new acetylcholinesterase and butyrylcholinesterase inhibitors through structurebased virtual screening", RSC Advances, 2017, 7(6), 3429-3438.

Chen W. et al. "Redox-Neutral [alpha]-Arylation of Amines", Organic Letters, vol. 16, No. 3, 2014, pp. 730-732.

Chrovian, C. C. et al. "A Dipolar Cycloaddition Reaction to Access 6-Methyl-4,5,6,7-tetrahydro-1H-[1,2,3]triazolo[4,5-c]pyridines Enables the Discovery Synthesis and Preclinical Profiling of a P2X7 Antagonist Clinical Candidate", J. Med. Chem. 2018, 61(1), p. 207-223.

Collet, A. "Resolution of Racemates: Did you say 'Classical?'", Angewandte Chemie International Edition, 1998, 37(23), 3239-3241.

Dai, W. et al. "Highly Chemoselective and Enantioselective Catalytic Oxidation of Heteroaromatic Sulfides via High-Valent Manganese(IV)-Oxo Cation Radical Oxidizing Intermediates", ACS Catalysis, 2017, vol. 7, p. 4890-4895.

Dassanayaka, S. and Jones, S. "O-GlcNAc and the cardiovascular system", Pharmacology & Therapeutics, 2014, 142, 62-71.

Database registry (online) Chemical abstract service, Columbus, Ohio, US; Dec. 6, 2011, "Piperazine, 1-[1-(1,3-benzodioxol-5-yl)ethyl]-4-(5-bromo-6-methoxy-2-pyridinyl)-", Database accession No. 1349611-60-4.

Database Pubchem Compound (Online) NCBI; Jan. 24, 2012, XP002768130, Database accession No. CID 54914491.

Database PubChem Compound (Online) NCBI; May 28, 2009; XP002768131, Database accession No. CID 28798635.

Database PubChem Compound, NCBI; 9. Apr. 2016; XP002768133, Database accession No. CID 118902929.

Database Registry, Chemical Abstracts Service, 2016, CID120907609, 10 pages.

Database Registry, Chemical Abstracts Service, Jan. 11, 2017, XP002768132, Database accession No. 2055841-81-9.

Dorfmueller, H. C. et al. "Cell-Penetrant, Nanomolar O-GlcNAcase Inhibitors Selective against Lysosomal Hexosaminidases", Chem. Biol., 2010, 17, 1250-1255.

Dubois, B. et al. "Preclinical Alzheimer's disease: Definition, natural history, and diagnostic criteria", Alzheimers Dement., 2016, 12, 292-323.

Dubois, B. et al. "Advancing research diagnostic criteria for Alzheimer's disease: the IWG-2 criteria", Lancet Neurol., 2014, 13, 614-629.

Dyatkin, A. B. et al. "Determination of the Absolute Configuration of a Key Tricyclic Component of a Novel Vasopressin Receptor Antagonist by Use of Vibrational Circular Dichroism", Chirality, 2002, 14, 215-219.

Ellman, J. A. et al. "N-tert-Butanesulfinyl Imines: Versatile Intermediates for the Asymmetric Synthesis of Amines" Acc. Chem. Res. (2002), 35, pp. 984-995.

Fleury-Bregeot et al. "Suzuki-Miyaura Cross-Coupling of Potassium Alkoxyethyltri-fluoroborates: Access to Aryl/Heteroarylethyloxy Motifs", J. Org. Chem. 2012, vol. 77, No. 22, p. 10399-10408.

Fors, B. P. et al. "A Highly Active Catalyst for Pd-Catalyzed Amination Reactions: Cross-Coupling Reactions Using Aryl Mesylates and the Highly Selective Monoarylation of Primary Amines Using Aryl Chlorides", J. Am. Chem. Soc., 2008, 130, 13552-13554.

Frehel, D. et al. "New synthesis of 5,6,7,8-tetrahydro-4H-thieno[2,3-d]azepine", Journal of Heterocyclic Chemistry, 1985, vol. 22, p. 1011-1016.

Frings, M. et al. "Sulfoximines from a Medicinal Chemist's Perspective: Physicochemical and in vitro Parameters Relevant for Drug Discovery", European Journal of Medicinal Chemistry, 2017, 126, 225-245.

Goho, A. "Tricky Business", Science News, 2004, 166(8), 122-124.

Gong et al. "O-GlcNAcylation: A regulator of tau pathology and neurodegeneration", Alzheimer's & Dementia, 2016, vol. 12, p. 1078-1089.

Golub, T. R. et al. "Molecular Classification of Cancer: Class Discovery and Class Prediction by Gene Expression Monitoring", Science, 1999, 286, 531-537.

Gould, P. L. "Salt selection for basic drugs", International Journal of Pharmaceutics, 1986, 33, 201-217.

Graham, D. L. et al. "Increased O-GlcNAcylation reduces pathological tau without affecting its normal phosphorylation in a mouse model of tauopathy", Neuropharmacology, 2014, 79, 307-313.

Gujjar, R. et al. "Lead Optimization of Aryl and Aralkyl Amine-Based Triazolopyrimidine Inhibitors of Plasmodium falciparum Dihydroorotate Dehydrogenase with Antimalarial Activity in Mice", J. Med. Chem., 2011, 54 (11), 3935-3949.

Haleblian, J.; McCrone, W. "Pharmaceutical Applications of Polymorphism", J. Pharm. Sci., 1969, 58(8), 911-929.

Haleblian, J. "Characterization of Habits and Crystalline Modification of Solids and Their Pharmaceutical Applications", J. Pharm. Sci., 1975, 64(8), 1269-1288.

Hemming, K. "Product Class 6: 1,2,4-Oxadizoles" Science of Synthesis, (2004), 13(6), pp. 127-184.

Hulikal, V. "Deuterium Labeled Compounds in Drug Discovery Process", Abstract, Bioorganics ond Applied Materials Pvt Ltd. (2010), 1 page.

Jakopin, Z. et al. "Recent Advances in the Synthesis of 1,2,4- and 1,3,4-Oxadiazoles" Current Organic Chemistry, (2008), 12(10), pp. 850-898.

Kempson, J. "Name Reactions in Heterocyclic Chemistry II" John Wiley & Sons. Eds. Jie Jack Li and E. J. Corey, (2011), pp. 299-308.

Kim, E. J. et al. "Enzymatic characterization of O-GlcNAcase isoforms using a fluorogenic GlcNAc substrate", Carbohydrate Research, 2006, 341(8), p. 971-982.

Kim, E. J. "Chemical Arsenal for the Study of O-GlcNAc", Molecules, 2011, vol. 16, p. 1987-2022.

Kim et al. "Discovery of β-Arrestin Biased Ligands of 5-HT$_7$R", Journal of Medicinal Chemistry, 2018, vol. 61, p. 7218-7233.

Knapp, S. et al. "An Allosamizoline/ Glucosamine Hybrid NAGase Inhibitor", Synlett, 1997, 5, 435-436.

Lefebvre, T. "Recall sugars, forget Alzheimer's", Nature Chemical Biology, 2012, 8(4), 325-326.

Legros, J. et al. "Applications of Catalytic Asymmetric Sulfide Oxidations to the Syntheses of Biologically Active Sulfoxides", Adv. Synth. Catal., 2005, 347, 19-31.

Liu, X. et al. "Rational Use of Plasma Protein and Tissue Binding Data in Drug Design", J. Med. Chem. 2014, 57, 8238-8248.

Marwaha, A. et al. "Bioisosteric Transformations and Permutations in the Triazolopyrimidine Scaffold to Identify the Minimum Pharmacophore Required for Inhibitory Activity against Plasmodium falciparum Dihydroorotate Dehydrogenase", J. Med. Chem., 2012, 55(17), 7425-7436.

Mariappa, D. et al. "A mutant O-GlcNAcase as a probe to reveal global dynamics of the Drosophila O-GlcNAc developmental proteome", Biochem J., 2015, 470(2), 255-262.

Marotta, N. P. et al., "O-GlcNAc modification blocks the aggregation and toxicity of the Parkinson's disease associated protein α-synuclein", Nat. Chem, 2015, 7(11), 913-920.

Masuda, N. et al. "Studies of nonnucleoside HIV-1 reverse transcriptase inhibitors. Part 1: Design and synthesis of thiazolidenebenzenesulfonamides", Bioorg. Med. Chem., 2004, 12, 6171-6182.

Merchant, R. R. et al. "Regioselective Preparation of Saturated Spirocyclic and Ring-Expanded Fused Pyrazoles", J. Org. Chem. 2014, vol. 79, No. 18, p. 8800-8811.

(56) References Cited

OTHER PUBLICATIONS

Micksch, M. et al. "Synthesis of 1,2-Diaryl- and 1-Aryl-2-alkylimidazoles with Sterically Demanding Substituents", Eur J. Org. Chem. 2013, Issue 27, p. 6137-6145.
Miller III et al. "Design of e-pharmacophore models using compound fragments for the trans-sialidase of Trypanosoma cruzi: screening for novel inhibitor scaffolds", Journal of Molecular Graphics and Modelling, vol. 45, 2013, p. 84-97.
Mittur A. "Piribedil: Antiparkinsonian Properties and Potential Clinical Utility in Dopaminergic Disorders" Current Drug Therapy (2011), 6, pp. 17-34.
Moradi-Afrapoli, F. et al. "In vitro α-glucosidase inhibitory activity of phenolic constituents from aerial parts of Polygonum hyrcanicum", DARU Journal of Pharmaceutical Sciences, 2012, 20(1), 37, 6 pages.
Motiwala, H. F. et al. "Remodeling and Enhancing Schmidt Reaction Pathways in Hexafluoroisopropanol", J. Org. Chem. 2016, vol. 81, No. 8, p. 1593-1609.
Nandi, A. et al. "Global Identification of O-GlcNAc-Modified Proteins", Anal. Chem., 2006, 78, 452-458.
Nelson, P. T. et al. "Correlation of Alzheimer Disease Neuropathologic Changes With Cognitive Status: A Review of the Literature", J. Neuropathol. Exp. Neurol., 2012, 71(5), 362-381.
Nettekoven, M. et al. "Synthetic Access to 2-Amido-5-aryl-8-methoxy-triazolopyridine and 2-Amido-5-morpholino-8-methoxy-triazolopyridine Derivatives as Potential Inhibitors of the Adenosine Receptor Subtypes", Synthesis, 2003, 1649-1652.
Obach, R. S. "Prediction of human clearance of twenty-nine drugs from hepatic microsomal intrinsic clearance data: and examination of in vitro half-life approach and nonspecific binding to microsomes", Drug. Metab. Dispos., 1999, 27(11), 1350-1359.
Okamura, H. et al. "Rhodium-Catalyzed Imination of Sulfoxides and Sulfides: Efficient Preparation of N-Unsubstituted Sulfoximines and Sulfilimines", Organic Letters, 2004, 6, 1305-1307.
O'Mahony, G. E. et al. "Synthesis of enantioenriched sulfoxides" Arkivoc, 2011, 1-110.
Orain, D. et al. "Synthesis of Orthogonally Protected 2,6-Diazaspiro[3.5]nonane and 2,6-Diazaspiro[3.4]octane Analogues as Versatile Building Blocks in Medicinal Chemistry", Synlett, 2015, 26(13), 1815-1818.
Papillon, J. P. N. et al. "Discovery of N-[5-(6-Chloro-3-cyano-1-methyl-1H-indol-2-yl)-pyridin-3-ylmethyl]-ethanesulfonamide, a Cortisol-Sparing CYP11B2 Inhibitor that Lowers Aldosterone in Human Subjects", J. Med. Chem., 2015, 58(23), 9382-9394.
Park, M.-J. et al. "High Glucose-induced O-GlcNAcylated Carbohydrate Response Element-binding Protein (ChREBP) Mediates Mesangial Cell Lipogenesis and Fibrosis", J. Biol. Chem., 2014, 289, 13519-13530.
Reddy et al. "Synthesis of Chiral Benzimidazole-Pyrrolidine Derivatives and their Application in Organocatalytic Aldol and Michael Addition Reactions", Synthetic Communications, vol. 37, No. 24, 2007, pp. 4289-4299.
Rouhi, A. M. et al. "The Right Stuff: From Research and Development to the Clinic, Getting Drug Crystals Right is Full of Pitfalls." Chem. Eng. News. (2003):32-35.
Ryan et al. "The O-GlcNAc modification protects against protein misfolding and aggregation in neurodegenerative disease", ACS Chemical Neuroscience, 2019, 17 pages.
SantaCruz, K. et al. "Tau Suppression in a Neurodegenerative Mouse Model Improves Memory Function", Science, 2005, 309, 476-481.
Serajuddin, A. T. M. "Salt formation to improve drug solubility", Advanced Drug Delivery Reviews, 2007, 59(7), 603-616.
Shan, X. et al. "Reduced protein O-glycosylation in the nervous system of the mutant SOD1 transgenic mouse model of amyotrophic lateral sclerosis", Neuroscience Letters, 2012, 516, 296-301.
Shen, Q. et al. "Hydroxycoumarin Derivatives: Novel and Potent α-Glucosidase Inhibitors", J. Med. Chem., 2010, 53(23), 8252-8259.
Shirude, P. et al. "Lead Optimization of 1,4-Azaindoles as Antimycobacterial Agents", J. Med. Chem., 2014, 57(13), 5728-5737.
Sippy, K. B. et al. "Preparation and characterization of N-(3-pyridinyl) spirocyclic diamines as ligands for nicotinic acetylcholine receptors", Bioorganic & Med. Chemistry Letters, 2009, 19(6), 1682-1685.
Skedelj, V. et al. "Discovery of the first inhibitors of bacterial enzyme D-aspartate ligase from Enterococcus faecium ($Asl_{fm}$)", Eur. J. Med. Chem., 2013, 67, 208-220.
Silverman, "Prodrugs and Drug Delivery Systems", The Organic Chemistry of Drug Design and Drug Action, (1992), Chapter 8, p. 352-399.
Song, S. et al. "Efficient and Practical Oxidative Bromination and Iodination of Arenes and Heteroarenes with DMSO and Hydrogen Halide: A Mild Protocol for Late-Stage Functionalization", Org. Lett., 2015, 17(12), 2886-2889.
Sperling, R. A. et al. "Toward defining the preclinical stages of Alzheimer's disease: Recommendations from the National Institute on Aging-Alzheimer's Association workgroups on diagnostic guidelines for Alzheimer's disease", Alzheimers Dement., 2011, 7, 280-292.
Spillantini, M. G.; Goedert, M. "Tau pathology and neurodegeneration", Lancet Neurol., 2013, 12, 609-622.
Tamura, B. K. et al. "Weight Loss in Patients with Alzheimer's Disease" J. Nutrition for the Elderly (2008), 26(3-4), pp. 21-38.
Tan, H. et al. "Rational Screening Approach for Classical Chiral Resolution under Thermodynamic Equilibrium: A Case Study of Diphenyl-Substituted N-Methyl-Piperazine", Organic Process Research and Development, 2011, 15(1), 53-63.
Tanuwidjaja, J. et al. "One-Pot Asymmetric Synthesis of Either Diastereomer of tert-Butanesulfinyl-protected Amines from Ketones", J. Org. Chem. 2007, 72, 626-629.
The U. S. Pharmacopeia 38—National Formulary 35 Chapter 941, Characterization of crystalline and partially crystalline solids by X-ray powder diffraction (XRPD) Official May 1, 2015, 427-431.
Thiel, O. R. et al. "Practical Synthesis of a Vanilloid Receptor-1 Antagonist" J. Org. Chem., (2008), 73(9), pp. 3508-3515.
Trapannone, R. et al. "O-GlcNAc transferase inhibitors: current tools and future challenges", Biochemical Society Transactions, 2016, 44(1), 88-93.
Vasudevan, A. et al. "Identification of aminopiperidine benzamides as MCHr1 antagonists", Bioorganic & Medicinal Chemistry Letters, 2005, 15(14), 3412-3416.
Volpe, D. A. "Application of Method Suitability for Drug Permeability Classification", The AAPS Journal, 2010, 12(4), 670-678.
Wall, G. M. "Pharmaceutical Applications of Drug Crystal Studies", Pharm. Manuf., 1986, 3, 32-42.
Wang, Z. et al. "Enrichment and Site Mapping of O-Linked N-Acetylglucosamine by a Combination of Chemical/Enzymatic Tagging, Photochemical Cleavage, and Electron Transfer Dissociation Mass Spectrometry", Mol. Cell Proteomics, 2010, 9(1), 153-160.
Waterman, K. C. "Improved Protocol and Data Analysis for Accelerated Shelf-Life Estimation of Solid Dosage Forms", Pharm. Res., 2007, 24(4), 780-790.
Weinberg, K. et al. "Synthesis and differential functionalisation of pyrrolidine and piperidine based spirodiamine scaffolds", Tetrahedron, 2013, 69(23), 4694-4707.
Wermuth, C. G. et al. "Designing Prodrugs and Bioprecursors I: Carrier Prodrugs", The Practice of Medicinal Chemistry: Chapter 31, Academic Press, 1996, 671-696.
Wiessner et al. "A novel non-carbohydrate o-linked beta-n-acetylglucosaminidase inhibitor increases tau o-glcnacylation In vivo", Abstracts of the Annual Meeting of the Society for Neuroscience, Society for Neuroscience, 2013, 43, 2 pages.
Williams, D. R. et al. "Pathological tau burden and distribution distinguishes progressive supranuclear palsy-parkinsonism from Richardson's syndrome", Brain, 2007, 130, 1566-1576.
Xu, Daqian et al. "The synthesis of chiral tridentate ligands from L-proline and their application in the copper(II)-catalyzed enantioselective Henry reaction", Tetrahedron Asymmetry, vol. 28, No. 7, 2017, p. 954-963.

(56) References Cited

OTHER PUBLICATIONS

Hiroshi Yamanaka, Hiroshi Miyazaki and Naomi chi Murakami, Chemical Abstract, "Separation of optical isomers", Japan, Gakkai Shopping Santa, 1989, 21 pages.
Yoshida, M. et al. "Study of biodegradable copoly(L-lactic acid/glycolic acid) formulations with controlled release of Z-100 for application in radiation therapy", Int. J. Pharm., 1995, 115, 61-67.
Youngdale et al. "Synthesis and pharmacological activity of 3-(2-pyrrolidinyl)indoles", Journal of Medicinal Chemistry, vol. 7, Jul. 1, 1964, pp. 415-427.
Yu, Y. J. et al. "One-Pot Synthesis of Spirocyclic or Fused Pyrazoles from Cyclic Ketones: Calcium Carbide as the Carbon Source in Ring Expansion", Org. Chem. 2017, vol. 82, No. 18, p. 9479-9486.
Yuzwa, S. A. et al. "Mapping O-GlcNAc modification sites on tau and generation of a site-specific O-GlcNAc tau antibody", Amino Acids, 2011, 40, 857-868.
Yuzwa, S. A. et al. "A potent mechanism-inspired O-GlcNAcase inhibitor that blocks phosphorylation of tau in vivo", Nat. Chem. Biol., 2008, 4(8), 483-490.
Yuzwa et al. "O-GlcNAc and neurodegeneration: biochemical mechanisms and potential roles in Alzheimer's disease and beyond", Chem. Soc. Review, 2014, 20 pages.
Yuzwa, S. A. et al. "Increasing O-GlcNAc slows neurodegeneration and stabilizes tau against aggregation", Nat. Chem. Biol., 2012, 8(4), 393-399.
Zenzola, M. et al. "Transfer of Electrophilic NH Using Convenient Sources of Ammonia: Direct Synthesis of NH Sulfoximines from Sulfoxides", Angew. Chem. Int. Ed., 2016, 55, 7203-7207.
Zhang, Chen et al. "Nontraditional Reactions of Azomethine Ylides: Decarboxylative Three-Component Couplings of [alpha]-Amino Acids", Journal of the American Chemical Society, vol. 132, No. 6, 2010, pp. 1798-1799.
Addis et al., "Efficient conversion of astrocytes to functional midbrain dopaminergic neurons using a single polycistronic vector". PloS one. Dec. 9, 2011; 6(12): 8 pages.
Alenghat T. et al., "Histone deacetylase 3 coordinates commensal bacteria-dependent intestinal homeostasis", (2013) Nature 504:153-157.
Boxer AL et al., "Davunetide in patients with progressive supranuclear palsy: a randomised, double-blind, placebo-controlled phase 2/3 trial", Lancet Neurol. 2014; 13(7): 676-85.
Boxer et al., "Advances in progressive supranuclear palsy: new diagnostic criteria, biomarkers, and therapeutic approaches.", Lancet 16: 552-563, 2017.
Chen YJ et al., "Protective Effects of Glucosamine on Oxidative-Stress and Ischemia/Reperfusion-Induced Retinal Injury", (2015), Invest Ophthalmol. Vis Sci. 56(3): 1506-1516.
Co-pending U.S. Appl. No. 18/570,861, inventors Beher; Dirk et al., filed on Dec. 15, 2023.
Fleming et al., "Early and Progressive Sensorimotor Anomalies in Mice Overexpressing Wild-Type Human alpha-Synuclein", 2004, The Journal of Neuroscience, 24 (42): 9434-40.
Gilbert S. et al., "Enterocyte STAT5 promotes mucosal wound healing via suppression of myosin light chain kinase-mediated loss of barrier function and inflammation", (2012) EMBO Mol. Med.4: 109-124.
Han OW et al., "Direct Reprogramming of Fibroblasts into Neural Stem Cells by Defined Factors", (2012) Cell Stem Cell 10: 465-472.
Hinz et al., "Molecular Genetics of Neurodegenerative Dementias", Cold Spring Harbor Perspectives in Biology, 2017, 9:a023705 23 pages.
Höglinger et al., "Identification of common variants influencing risk of the tauopathy progressive supranuclear palsy", Nature Genetics 43 :699-705, 2011.
Höglinger GU et al., (2017) "Longitudinal magnetic resonance imaging in progressive supranuclear palsy: A new combined score for clinical trials", Movement Disorders, 32(6): 842-52.
Höglinger GU et al., (2017) "Clinical diagnosis of progressive supranuclear palsy: The movement disorder society criteria", Movement Disorders, 32: 853-64.
Kim J. et al., "Direct reprogramming of mouse fibroblasts to neural progenitors", (2011) Proc Natl Acad Sci USA 108(19) :7838-7843.
Kuhn J. et al. "Deep Brain Stimulation of the Nucleus Basalis of Meynert in Early Stage of Alzheimer's Dementia", (2015) Brain Stimulation 8: 838-839.
Levine PM. et al., (2019) "α-Synuclein O-GlcNAcylation alters aggregation and toxicity, revealing certain residues as potential inhibitors of Parkinson's disease", Proc. Natl. Acad. Sci. USA 116(5):1511-1519.
Lim MS. et al., "Generation of Dopamine Neurons from Rodent Fibroblasts through the Expandable Neural Precursor Cell Stage", (2015) J. Biol. Chem. 290: 17401-17414.
Lozano AM et al., (2016) "A Phase II Study of Fornix Deep Brain Stimulation in Mild Alzheimer's Disease", Journal of Alzheimer's Disease, 54 : 777-787.
Lujan E. et al., "Direct conversion of mouse fibroblasts to self-renewing, tripotent neural precursor cells", (2012) Proc Natl Acad Sci USA 109 : 2527-2532.
Matsui T. et al., "Neural Stem Cells Directly Differentiated from Partially Reprogrammed Fibroblasts Rapidly Acquire Gliogenic Competency", (2012) Stem Cells 30: 1109-1119.
Mayer, Paul "On the Staining of Mucus", (1896), Mitt. zool. Stn. Neape., 12, pp. 303-330.
Mirzadeh Z. et al., "The rationale for deep brain stimulation in Alzheimer's disease", (2016) J. Neural Transm (Vienna) 123: 775-783.
Opposition Arguments, Notice of Opposition, Indian Pharmaceutical Alliance, in Patent Application No. 202127010343 dated Nov. 3, 2021 filed by Asceneuron S.A. (Applicant), dated Feb. 6, 2024, 26 pages.
Paul S. et al., "Evaluation of a PET Radioligand to Image O-GlcNAcase in Brain and Periphery of Rhesus Monkey and Knock-Out Mouse", J. Nucl. Med. 2019, 60(1), 129-134.
Racine R.J., (1972) "Modification of Seizure Activity by Electrical Stimulation: I. After-Discharge Threshold", Electroencephalography and Clinical Neurophysiology 32(3), 269-279.
Rockenstein E, et al., "Differential Neuropathological Alterations in Transgenic Mice Expressing alpha-synuclein From the Platelet-derived Growth Factor and Thy-1 Promoters", Journal of Neuroscience Research 68: 568-578 (2002).
Sanchez et al., "Human and rodent temporal lobe epilepsy is characterized by changes in OGlcNAc homeostasis that can be reversed to dampen epileptiform activity", (2019) Neurobiology of Disease 124: 531-543.
Sankar T et al., "Deep Brain Stimulation Influences Brain Structure in Alzheimer's Disease", (2015) Brain Stimulation 8: 645-654.
Sheng C. et al., "Direct reprogramming of Sertoli cells into multipotent neural stem cells by defined factors" (2012) Cell Res 22: 208-218.
Stamelou M et al., (2016) "Power calculations and placebo effect for future clinical trials in progressive supranuclear palsy", Mov Disord. 31 (5): 742-7.
Tolosa et al., (2014) "A phase 2 trial of the GSK-3 inhibitor tideglusib in progressive supranuclear palsy", Movement Disorders 29(4): 470-478.
Vierbuchen et al., "Direct conversion of fibroblasts to functional neurons by defined factors", (2010) Nature 463: 1035-1041.
Wahlund et al., (2001) "A new rating scale for age-related white matter changes applicable to MRI and CT", Stroke, 32(6):1318-1322.
Zhang SZ. et al., "Modeling Neurological Disease by Rapid Conversion of Human Urine Cells into Functional Neurons", (2016) Stem Cells International, 2016: 2452985.
Zhao J. et al., "Neuronal Transcription Factors Induce Conversion of Human Glioma Cells to Neurons and Inhibit Tumorigenesis", (2012) PLoS ONE7:e41506.
Zhao M, et al., "Deficiency in intestinal epithelial O-GlcNAcylation predisposes to gut inflammation", (2018) EMBO Mol. Med. 10: 18 pages.
CAS Registry Entry: 890335-15-6 (STN data summary sheet). Entered STN: Jul. 3, 2006, 1 pg.

* cited by examiner

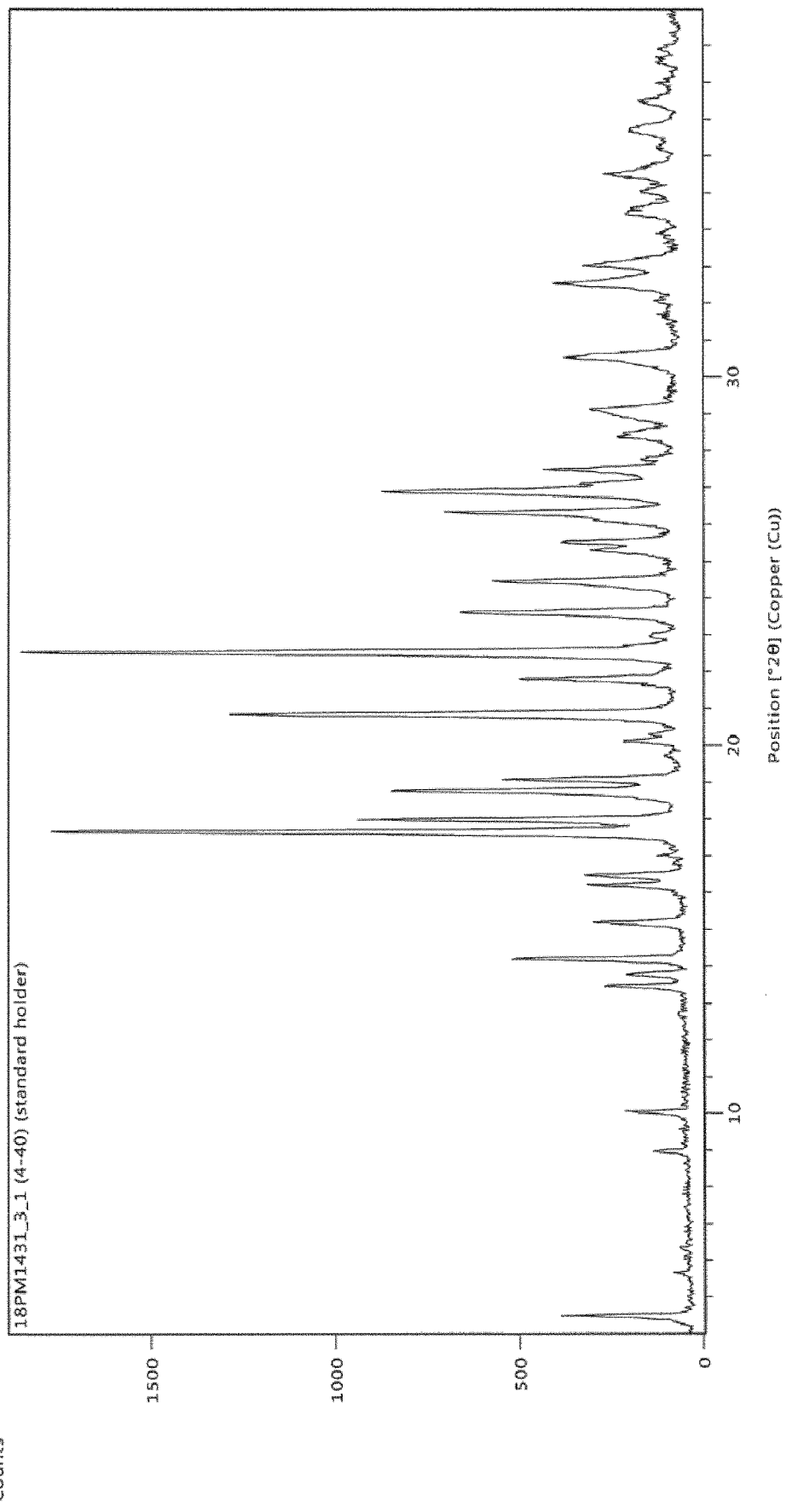
Figure 1: Characteristic X-ray powder diffraction pattern of crystalline Example 35 succinate salt, Form 1

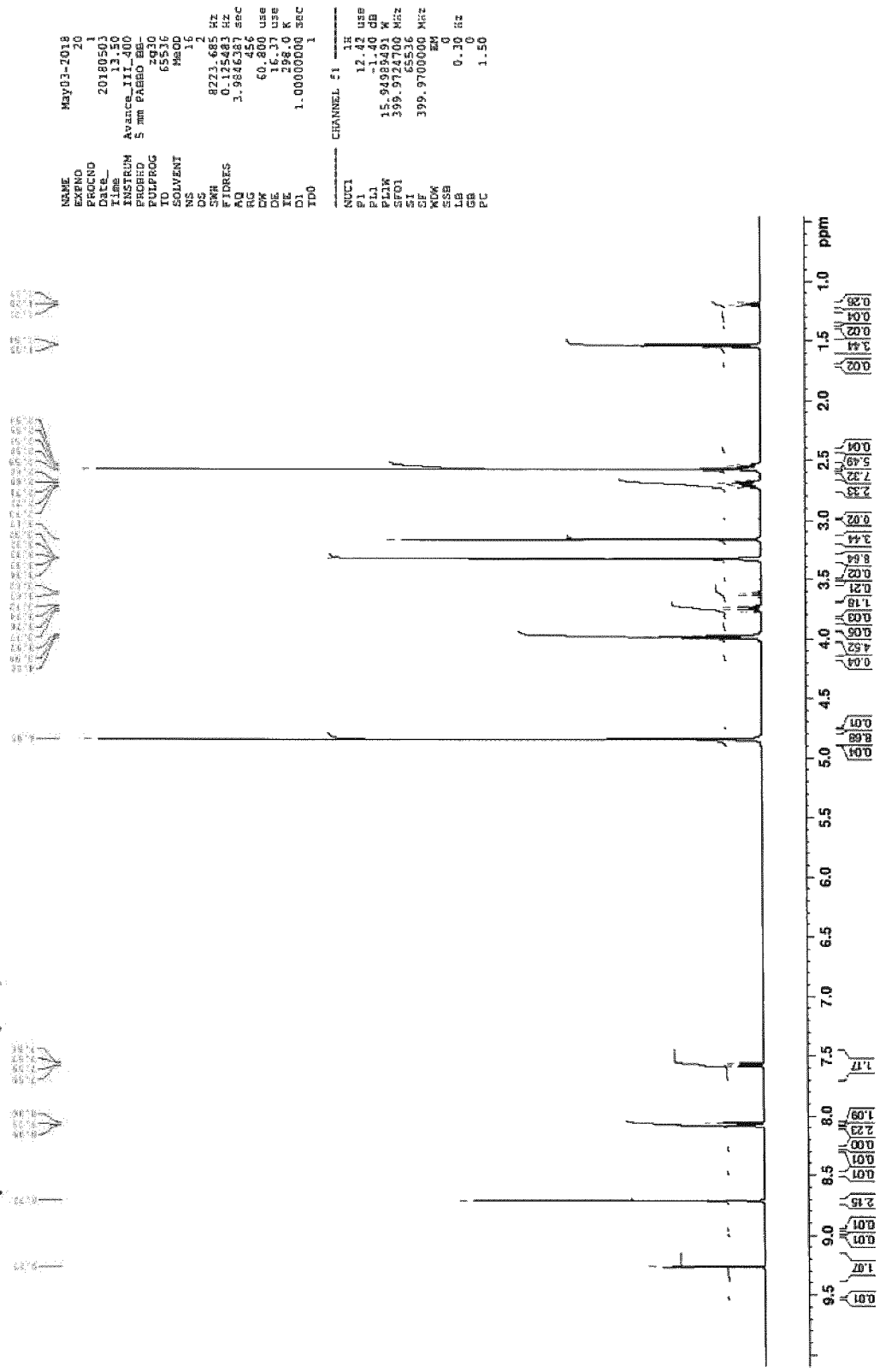
Figure 2: Characteristic ¹H NMR spectrum of crystalline Example 35 succinate salt, Form 1

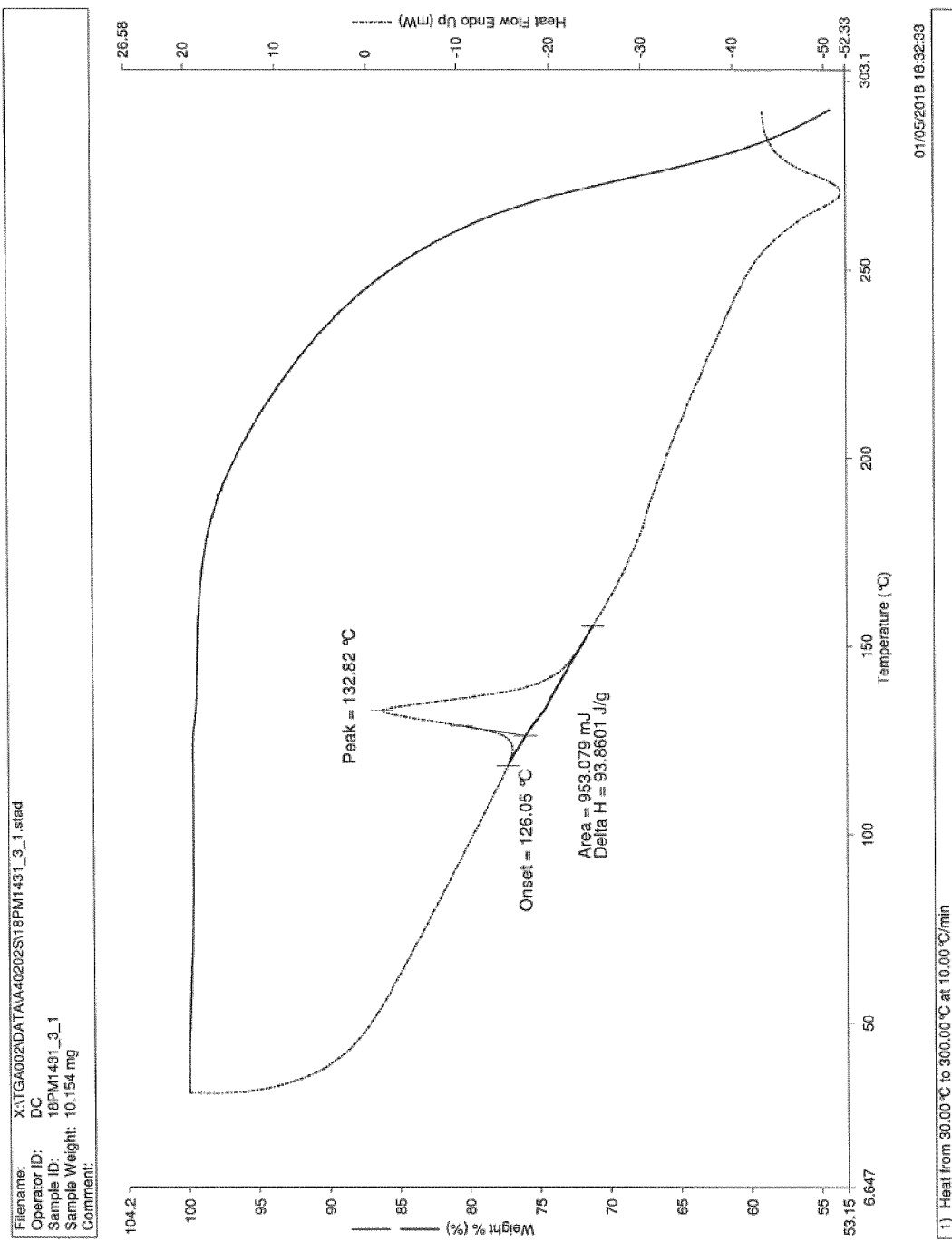
Figure 3: Characteristic STA thermogram of crystalline Example 35 succinate salt, Form 1

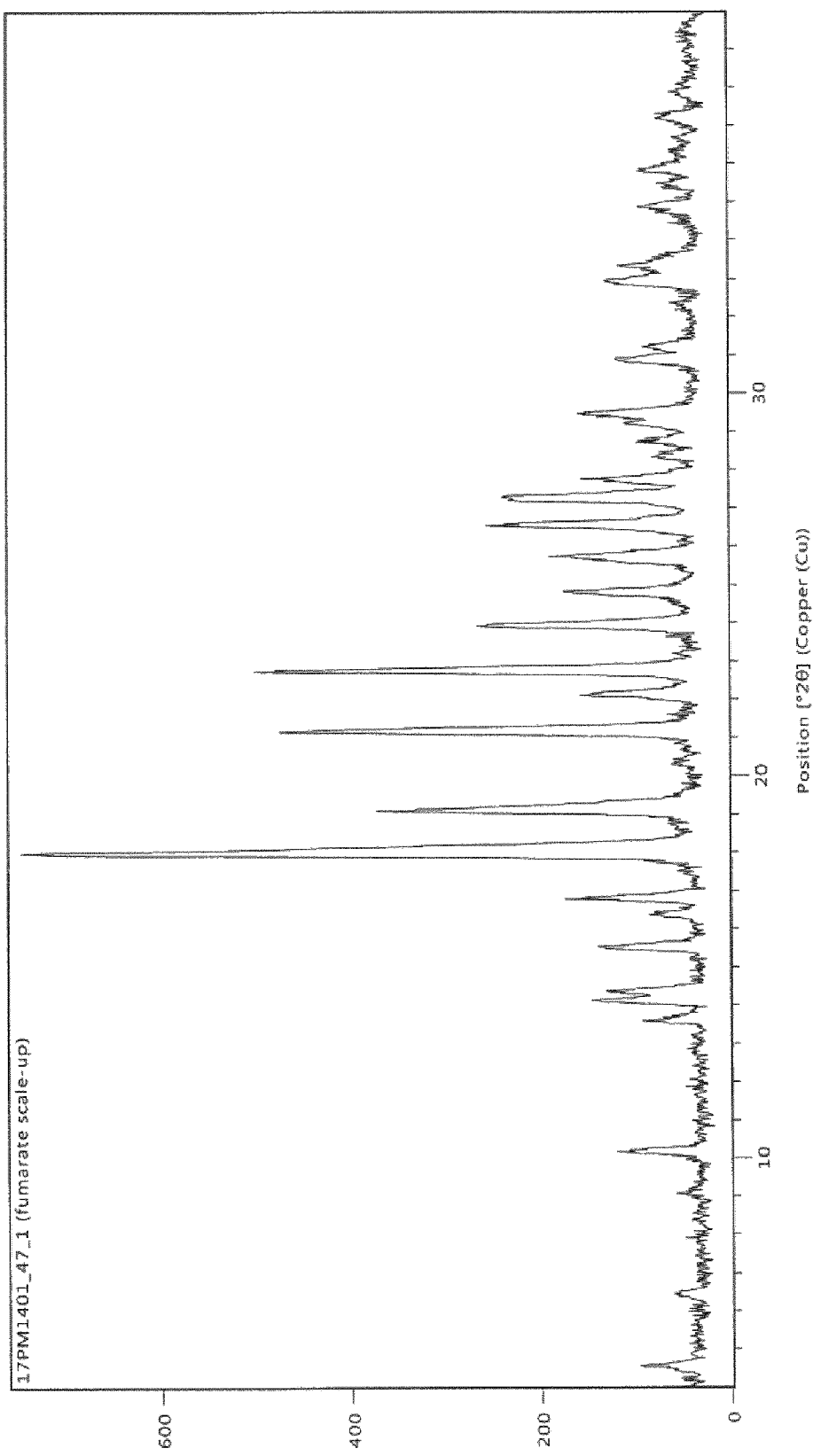
Figure 4: Characteristic X-ray powder diffraction pattern of crystalline Example 35 fumarate salt

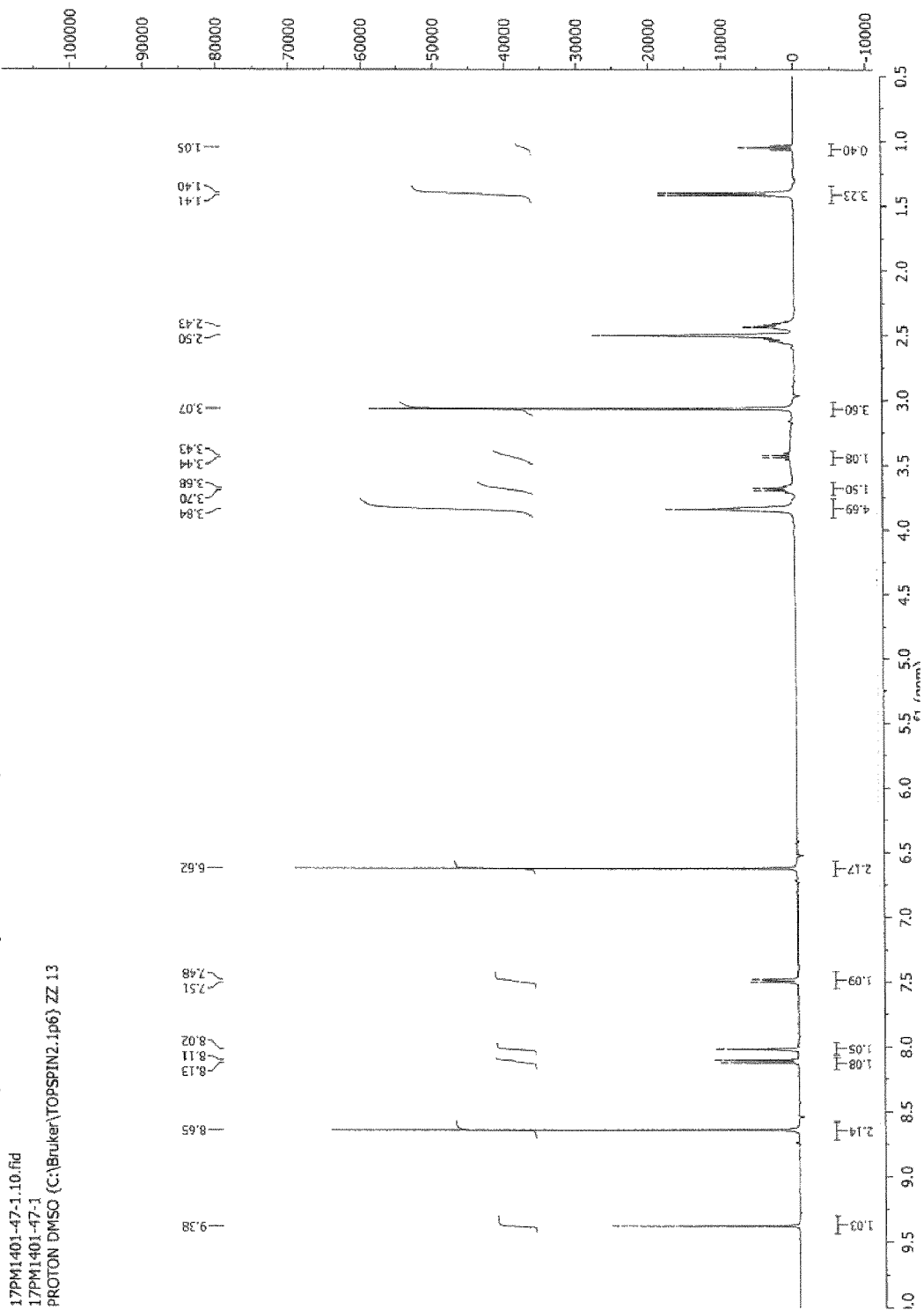
Figure 5: Characteristic $^1$H NMR spectrum of crystalline Example 35 fumarate salt

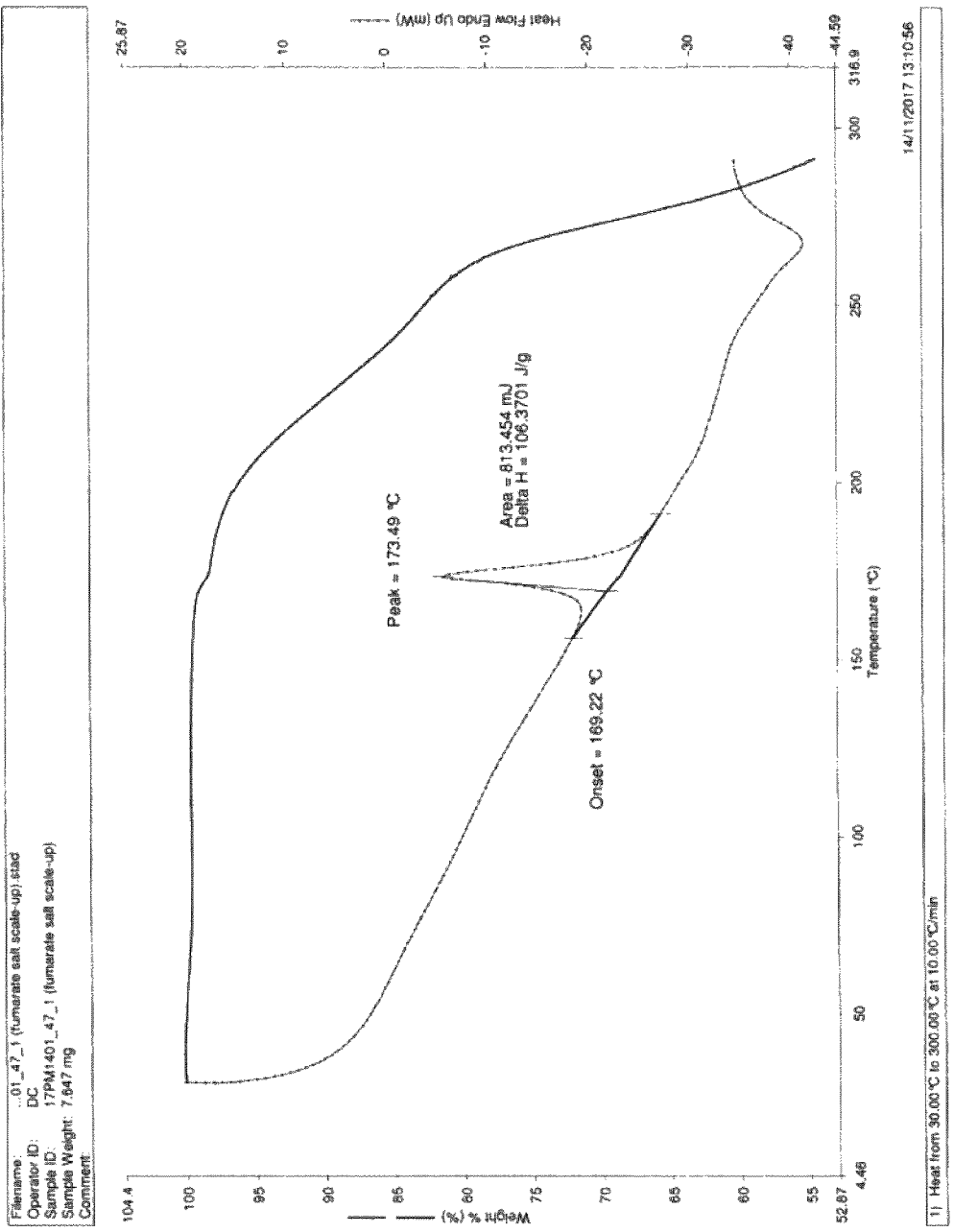
Figure 6: Characteristic STA thermogram of crystalline Example 35 fumarate salt

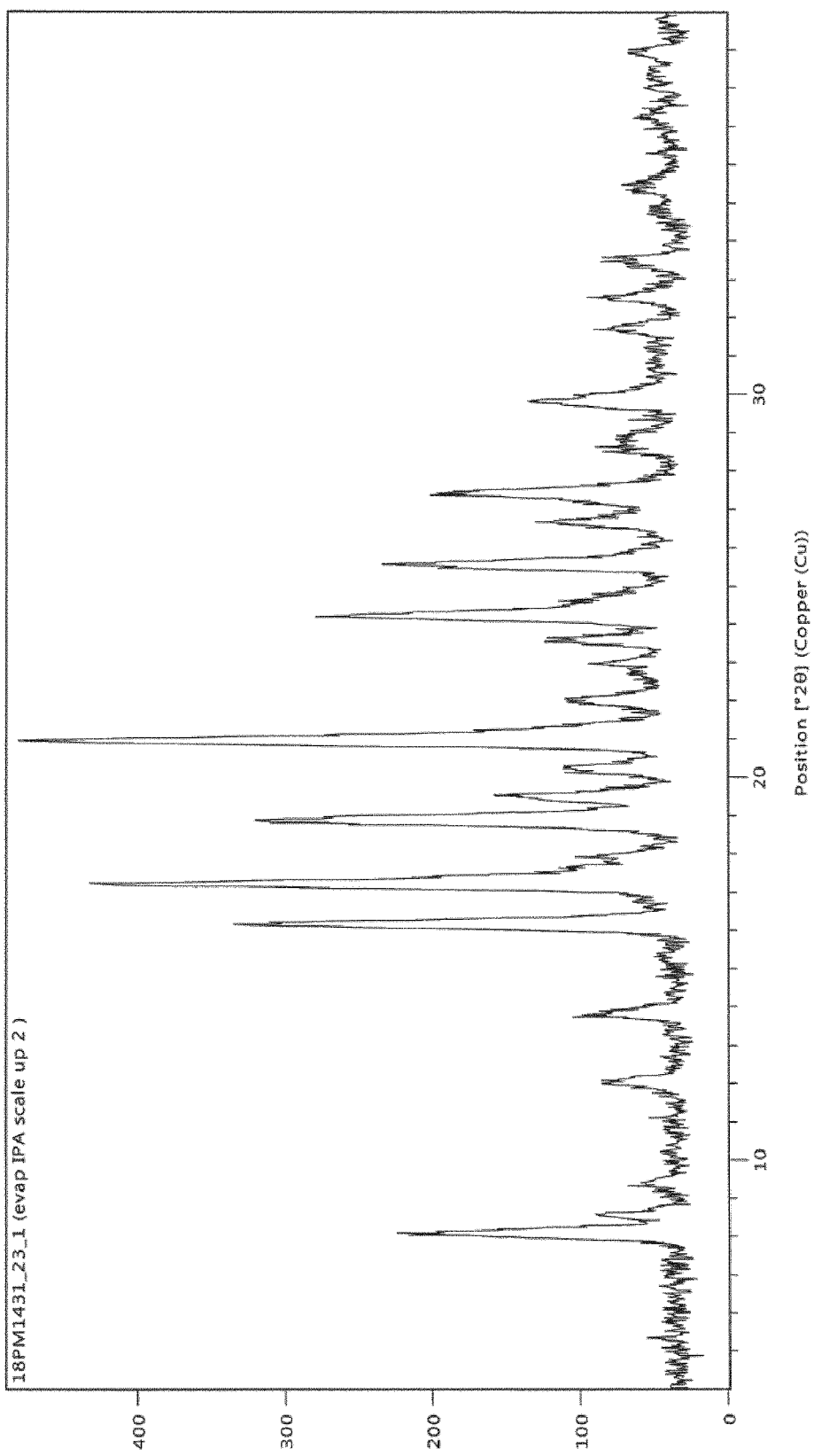
Figure 7: Characteristic X-ray powder diffraction pattern of crystalline Example 35 succinate salt, Form 2

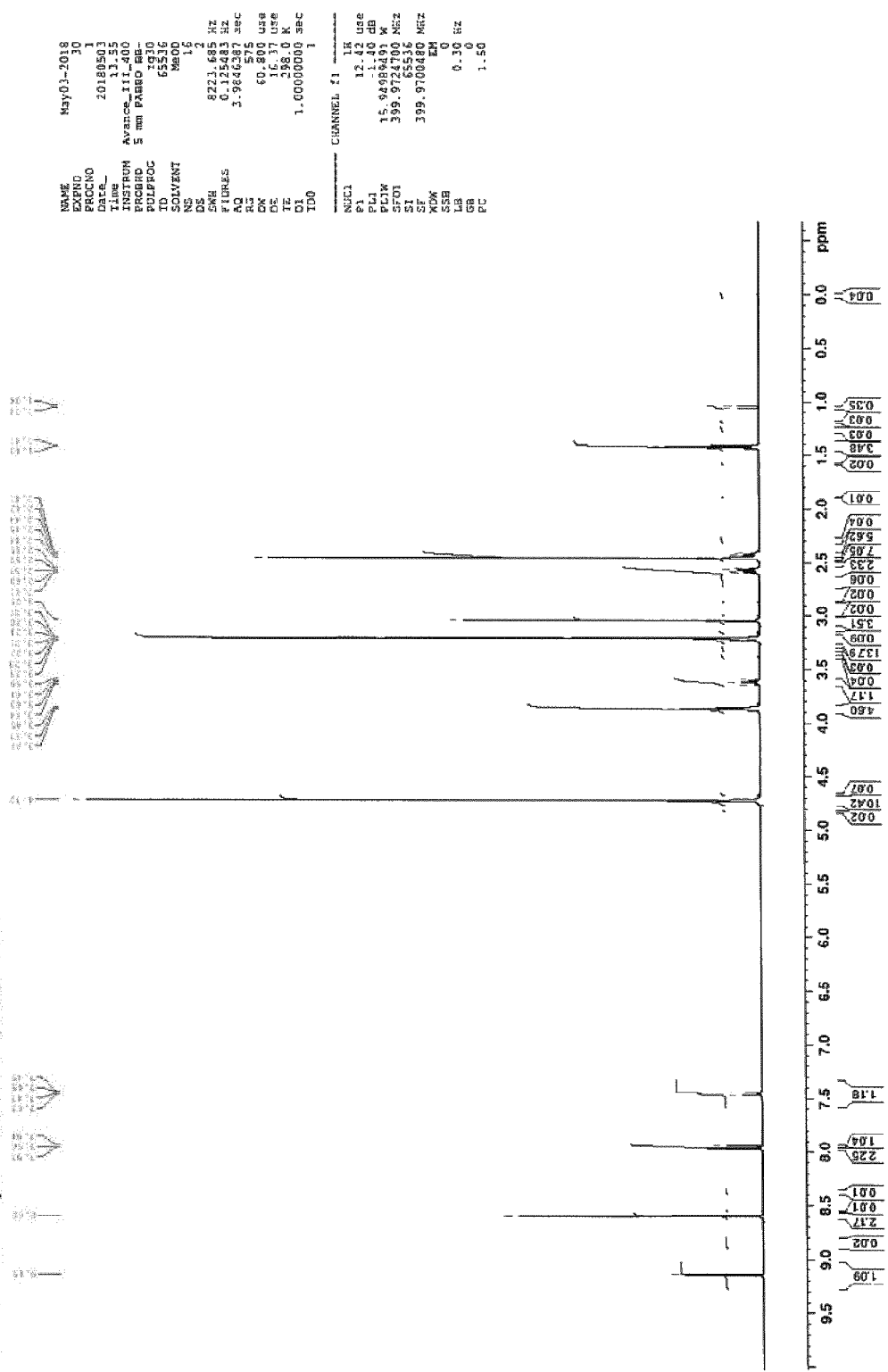
Figure 8: Characteristic $^1$H NMR spectrum of crystalline Example 35 succinate salt, Form 2

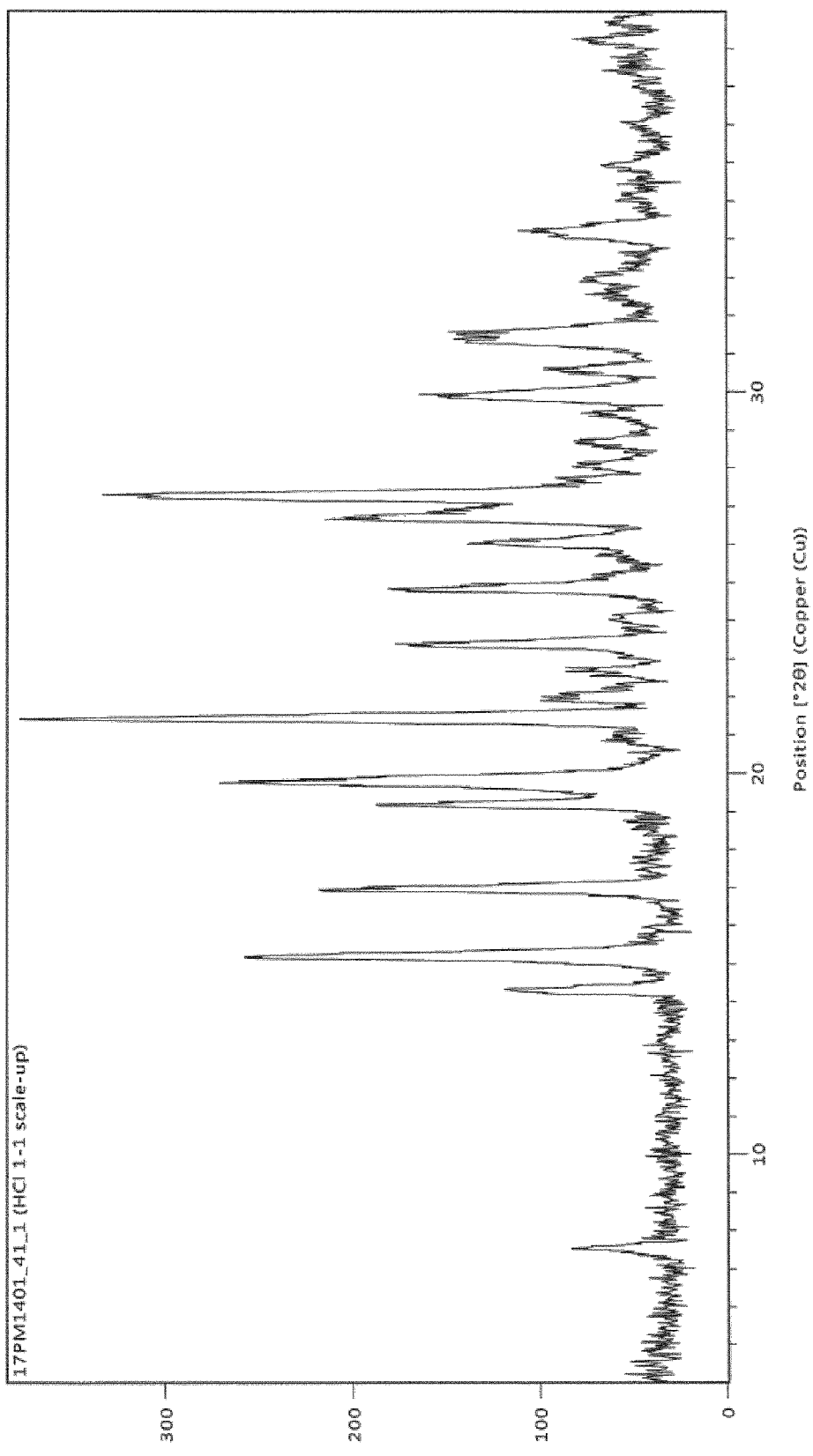
Figure 9: Characteristic X-ray powder diffraction pattern of crystalline Example 35 hydrochloride salt

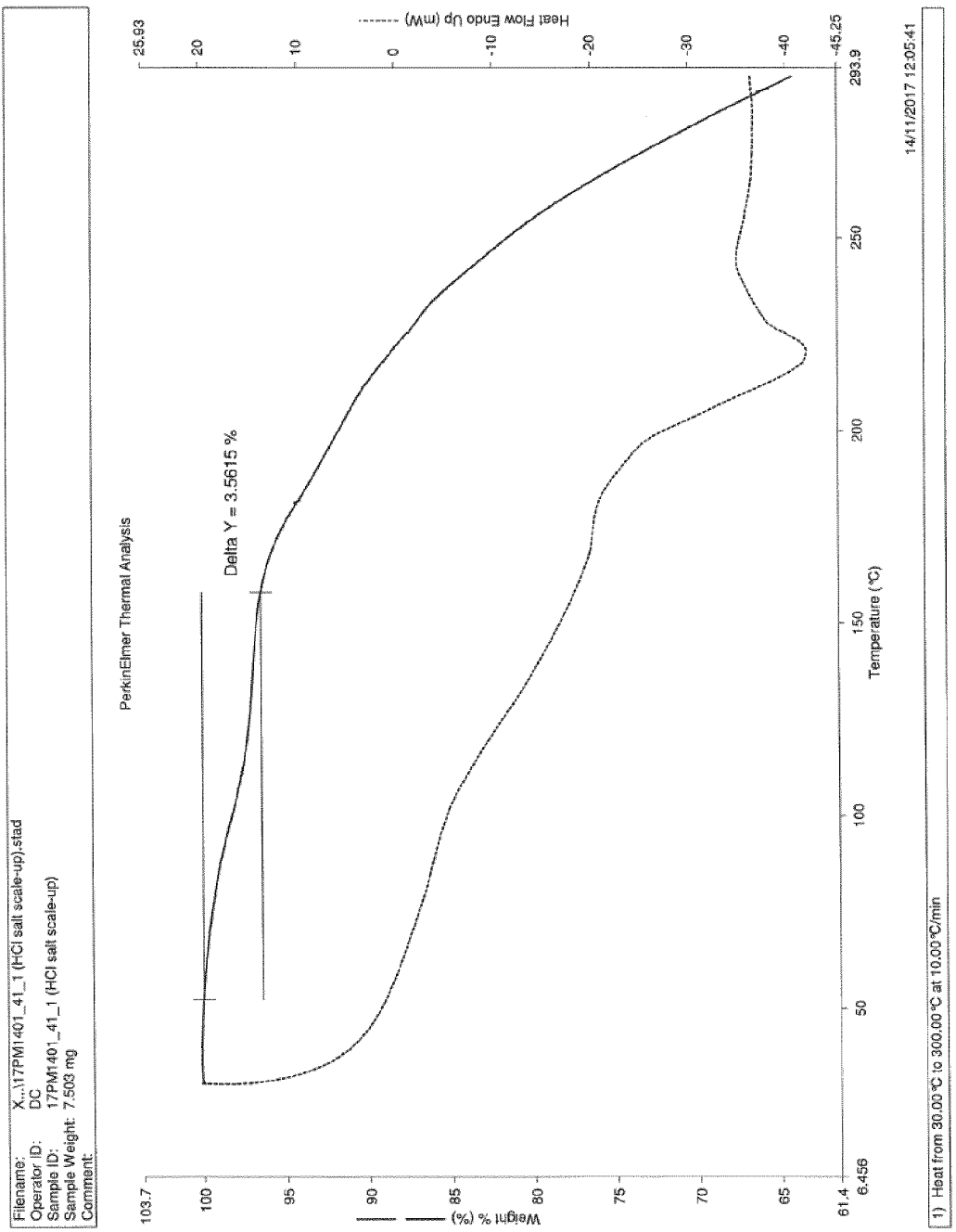
Figure 10: Characteristic STA thermogram of crystalline Example 35 hydrochloride salt

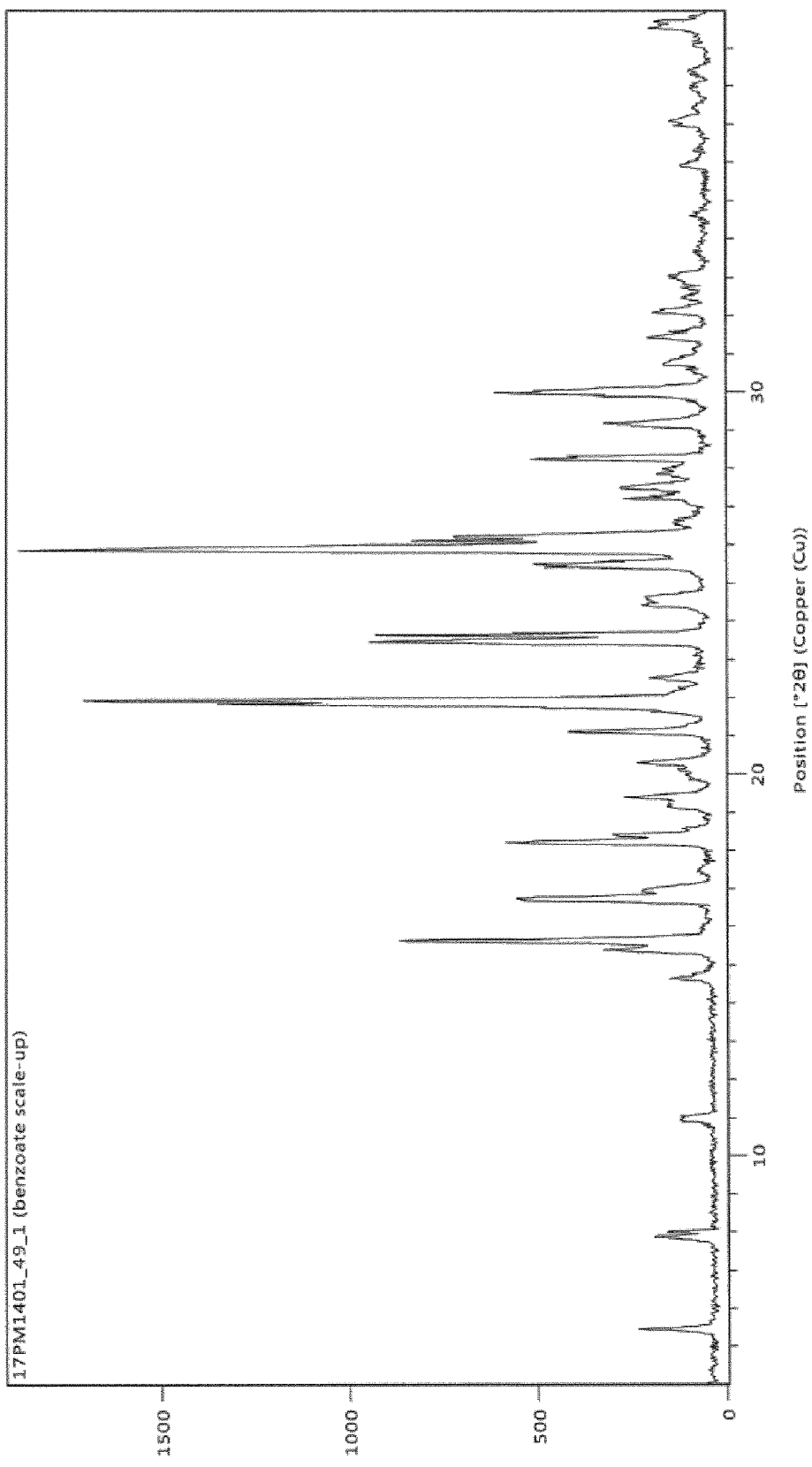
Figure 11: Characteristic X-ray powder diffraction pattern of crystalline Example 35 benzoate salt

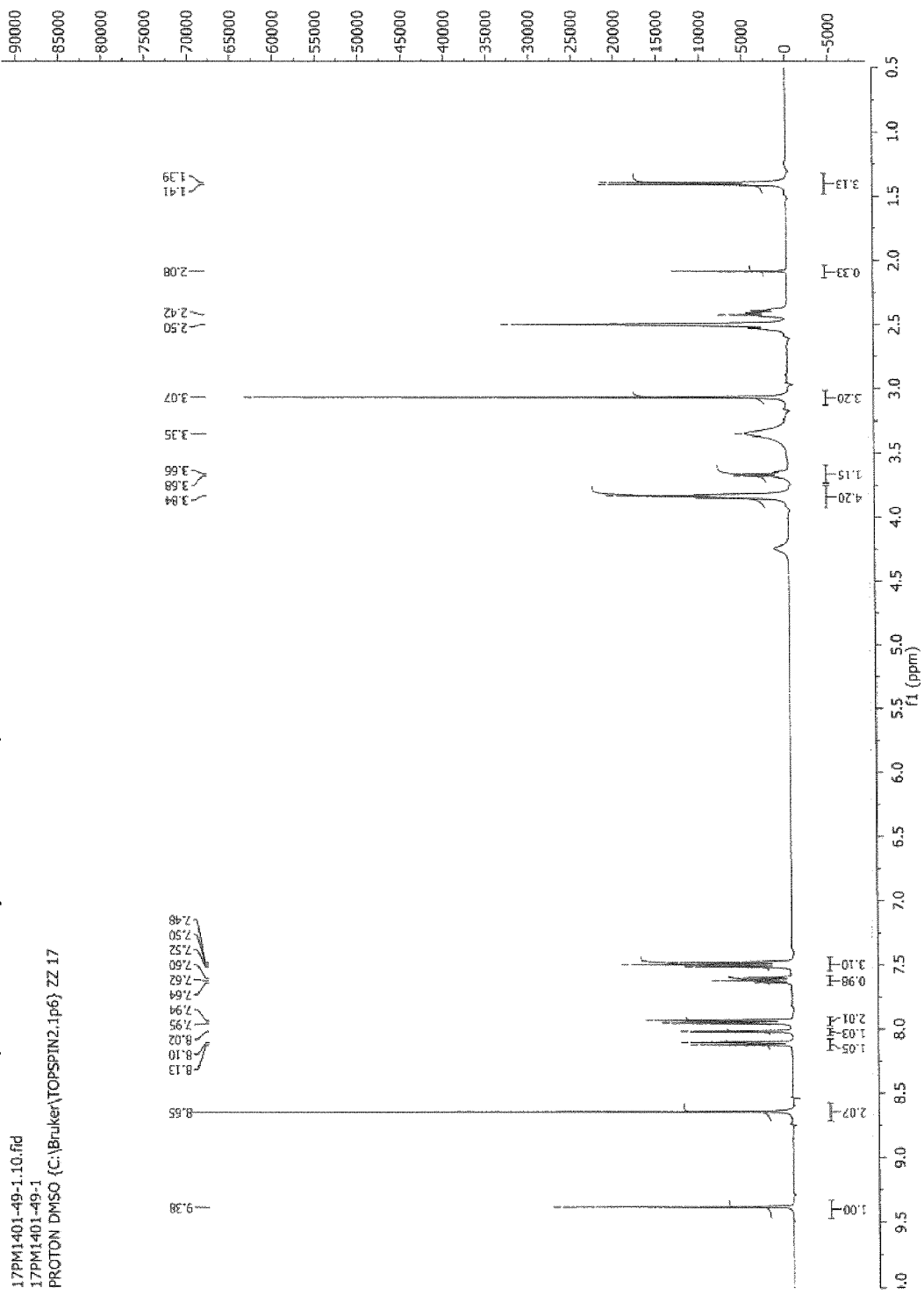
Figure 12: Characteristic ¹H NMR spectrum of crystalline Example 35 benzoate salt

SUCCINATE AND FUMARATE ACID ADDITION SALTS OF PIPERAZINE DERIVATIVES

RELATED APPLICATIONS

This application is a U.S. National Phase application, filed under 35 U.S.C. § 371(c), of International Application No. PCT/EP2019/072474, filed Aug. 22, 2019, which claims priority to, and the benefit of, European Application No. 18190155.4, filed Aug. 22, 2018, the contents of each of which are incorporated herewith in their entirety.

FIELD OF THE INVENTION

The invention relates to acid addition salts of succinic acid or fumaric acid with piperazine derivatives, as well as solid forms, such as polymorphic forms, thereof, which are useful as pharmaceutical ingredients and in particular as glycosidase inhibitors.

BACKGROUND OF THE INVENTION

Piperazine Derivatives of Formula I

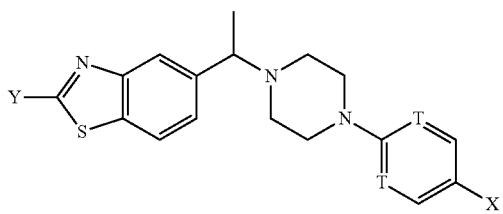

(I)

wherein X, Y and T are defined further below, are useful as pharmaceutical ingredients and show high activity as glycosidase inhibitors. Similar compounds are e.g. disclosed in PCT/EP2015/069598.

Although the compounds of formula I have very useful pharmaceutical activities as free bases, they are not ideal for pharmaceutical manufacturing and as such may not be suitable for certain dosage forms, especially oral dosage forms, due to their unfavorable dissolution behaviour and stability or reactivity and other properties in the solid state.

Thus, there is a need to provide improved solid forms comprising the compounds of formula I, which exhibit improved properties, can be easily manufactured into solid dosage forms or other pharmaceutical dosage forms, and show an improved dissolution behaviour and stability and/or are less reactive in the solid state.

SUMMARY OF THE INVENTION

It has now been found that compounds of formula I show improved solid state properties, after they have been transformed in acid addition salts of succinic acid or fumaric acid. In particular, the acid addition salts can be easily manufactured into solid dosage forms or other pharmaceutical dosage forms, and show an improved dissolution behavior and stability and/or are less reactive in the solid state. The acid addition salts of the present invention also exhibit low hygroscopicity.

It has also been found that certain polymorphic forms of the acid addition salts show even further improved properties, making them ideal for pharmaceutical manufacturing, in particular for solid oral dosage forms. Moreover, acid addition salts of the present invention that have a molar ratio of the compounds of formula I to the respective acid of 1 to 1 are especially stable, soluble and/or show other improved properties.

DETAILED DESCRIPTION OF THE INVENTION

The invention relates to the acid addition salt of succinic acid or fumaric acid with compounds of formula I

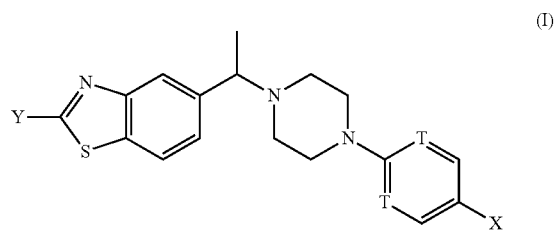

(I)

wherein
Y denotes H or $CH_3$,
T denotes N or CH,
X denotes one of the following sulfoximine groups: $S(O)(NR^{3'})CH_3$, $S(O)(NR^{3'})CH_2CH_3$, $S(O)(NR^{3'})CH_2CH_2OH$, $S(O)(NR^{3'})CH_2CH_2OCH_3$, $NS(O)(R^{3'})CH_3$, $NS(O)(R^{3'})CH_2CH_3$, $NS(O)(R^{3'})CH_2CH_2OH$ or $NS(O)(R^{3'})CH_2CH_2OCH_3$ and
$R^{3'}$ denotes H or a straight chain or branched alkyl group having 1 to 12 carbon atoms, wherein 1 to 3 $CH_2$-groups may be replaced by a group selected from $SO_2$, CO, O and wherein 1 to 5 hydrogen atoms may be replaced by F, Cl, Br or I.
as well as stereoisomers, solid forms, such as solvates and polymorphic forms thereof.

"Solid forms" according to the invention is preferably a term generally embracing any solid state of a compound and/or its salts and/or its solvates, preferably crystalline forms, including polymorphic forms, but also amorphous forms (see: Aitipamula, S. et al. *Cryst. Growth Des.*, 2012, 12 (5), pp 2147-2152).

Polymorphism describes the occurrence of different solid or crystalline forms of a single compound and it is a property of certain compounds and complexes. Thus, polymorphs or polymorphic forms are distinct solids sharing the same molecular formula, yet each polymorph or polymorphic form may have distinct physical properties. Therefore, a single compound may give rise to a variety of polymorphic forms where each form has different and distinct physical properties, such as different solubility profiles, different melting point temperatures and/or different x-ray diffraction peaks.

The occurrence of a polymorphic form may be determined by the crystallization conditions such as choice of solvent(s), rate of solvent addition, temperature, stirring rate, level of super-saturation, and level of impurities. Hence, different crystallization processes may give rise to different polymorphs. Polymorphs also have different stabilities and may spontaneously convert from one form to another.

The unpredictability of polymorphism, both as regards the uncertainty that any forms could be found, and the lack of any standard methods for preparing a new form has e.g. been discussed in A. Goho, "Tricky Business," Science News, Vol. 166(8), Aug. 21, 2004, and A. M. Rouhi, "The Right Stuff," Chemical and Engineering News, Feb. 24, 2003, pages 32-35.

Polymorphs can be distinguished from each other by a variety of analytical techniques. Polymorphs exhibit distinct spectroscopic properties and can be identified using infrared spectroscopy, raman spectroscopy, and $^{13}$C-NMR spectroscopy. Due to the fact that each crystal form diffracts X-rays in different ways, X-ray powder diffractometry (XRPD) can also be used for identification and differentiation of two polymorphic forms. Furthermore, thermal methods such as differential scanning calorimetry (DSC), simultaneous thermal analysis (STA) and thermogravimetric analysis (TGA) can provide information unique to a particular polymorph. The polymorphic forms of a compound can also be distinguished by other methods such as, infrared spectrometry. For a general review of polymorphs and the pharmaceutical applications of polymorphs, See G. M. Wall, Pharm Manuf. 3, 33 (1986); J. Haleblian and W. McCrone, J. Pharm. Sci., 58, 91 1 (1969); and J. Haleblian, J. Pharm. Sci., 64, 1269 (1975).

The physicochemical properties may vary strongly between individual polymorphic forms. For example, solubility and dissolution rate may vary between polymorphs, leading to potential differences in bioavailability. Furthermore, mechanical properties such as flowability and compactability, which affect the processing properties of a compound, may be different. Stability, vapor impermeability and shelf life of a compound or dosage forms thereof, may also depend on the chosen polymorph.

In view of the potential differences between polymorphic forms of the same active pharmaceutical ingredients, there are extensive requirements set out by the regulatory drug approval authorities to control polymorphism. In particular, it is usually either required that only the same reproduceable single polymorphic form is preset in a given drug product or that mixtures of polymorphic forms are consistently and reproduceably obtained, such that the drug product remains at all times identical in all respects (ICH Topic Q 6 A, Specifications: Test Procedures and Acceptance Criteria for New Drug Substances and New Drug Products: Chemical Substances. May 2000 CPMP/ICH/367/96)

Mixtures of polymorphic forms of a given drug are often unsuitable for pharmaceutical development, as they may be composed of or contain polymorphic forms that are unstable and influence the consistancy of drug product.

Therefore, significant resources are invested by the pharmaceutical industry to discover a single stable polymorphic form that is suitable for pharmaceutical development and the reproduceable process for the specific manufacture of that single stable polymorph.

The polymorphic forms, including solvates of the present invention provide materials having desirable processing properties, such as ease of handling, ease of processing, storage stability, and ease of purification, or as desirable intermediate crystal forms that facilitate conversion to other polymorphic forms with improved properties. Moreover, the invention provides and stable forms of drug substances, which preferably exhibit thermodynamic stability, enhanced solubility, rapid onset of action and an enhanced bioavailability. The preferred acid addition salts of the present invention are improved in at least one of the aforementioned properties.

In a preferred embodiment, the invention relates to acid addition salts of compounds of formula I1, I2 and I3:

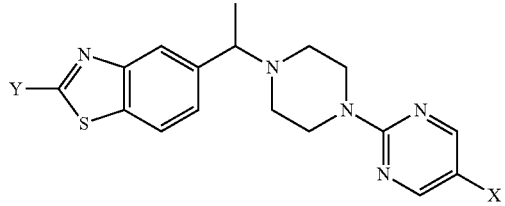

(I1)

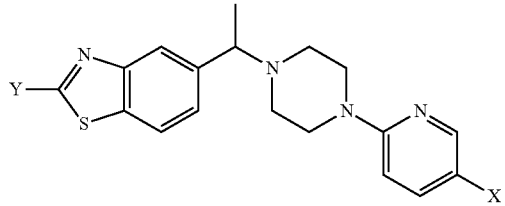

(I2)

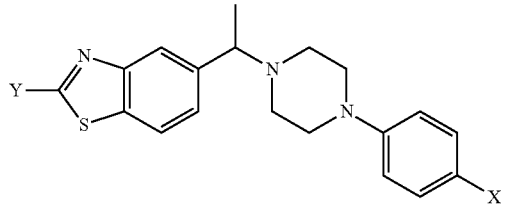

(I3)

wherein X and Y have the meaning given above and solid forms, such as solvates and polymorphic forms, thereof.

In a more preferred embodiment, the invention relates to the acid addition salts of compounds of formula I1a and I1b, I2a and I2b, and I3a and I3b

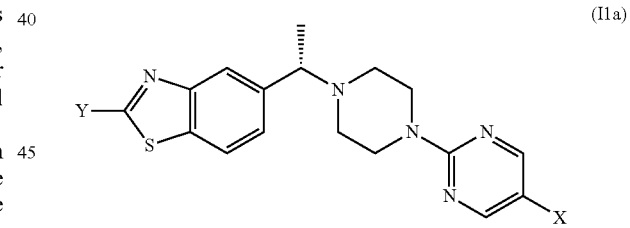

(I1a)

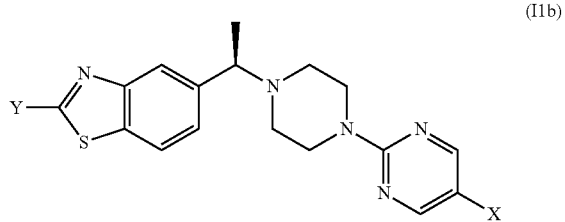

(I1b)

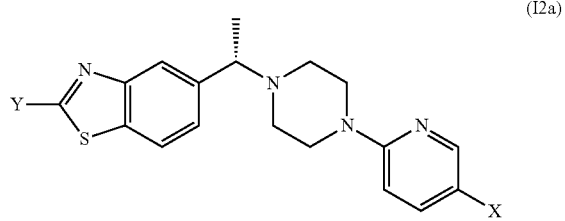

(I2a)

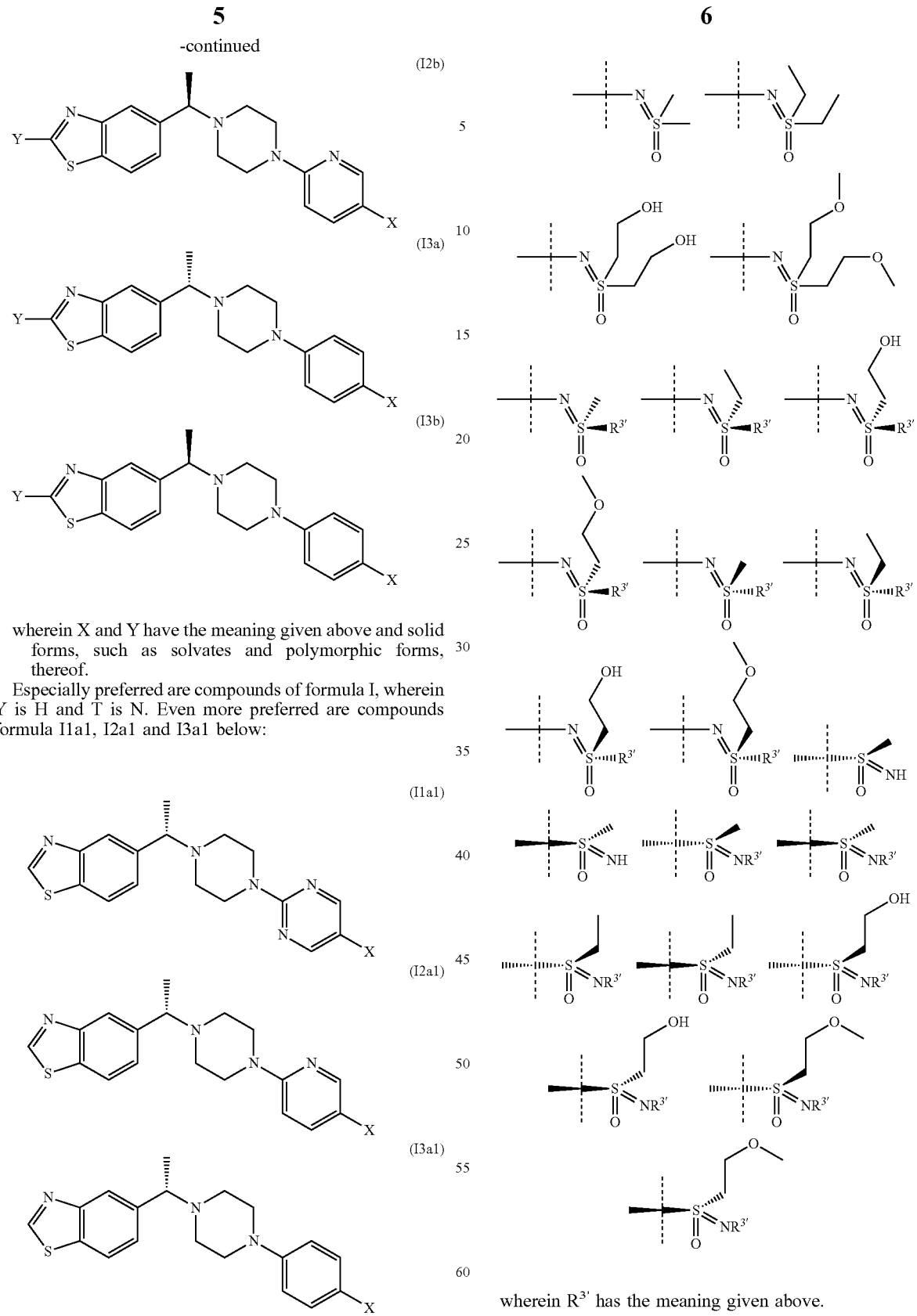

Very preferred are the acid addition salts of succinic acid or fumaric acid, as well as solid forms, such as polymorphic forms thereof, of a compound of formula Ia, Ib, Ic, Id, Ie, If, Ig, Ih, Ii, Ij, Ik, IL:

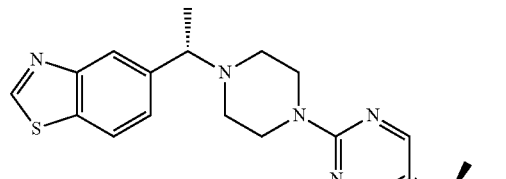
(Ia)

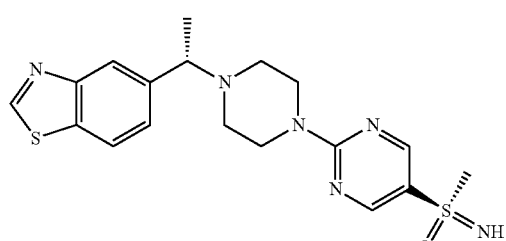
(Ib)

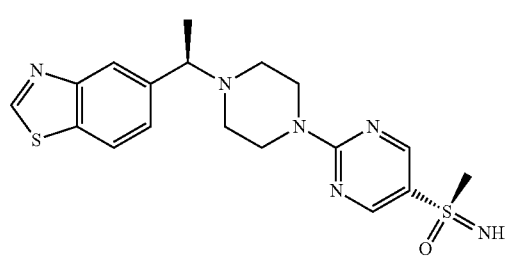
(Ic)

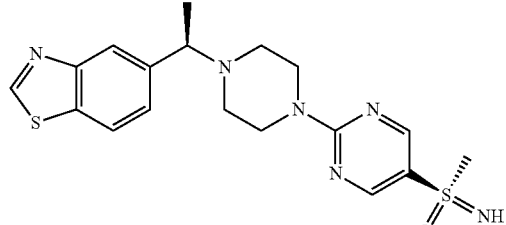
(Id)

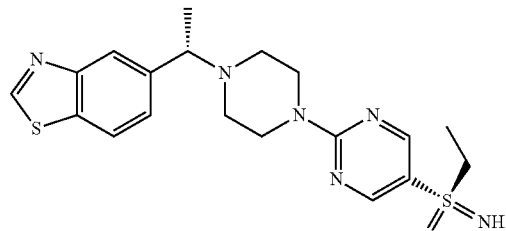
(Ie)

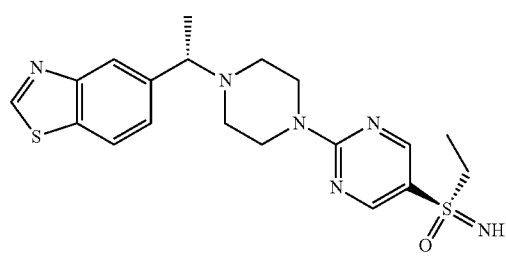
(If)

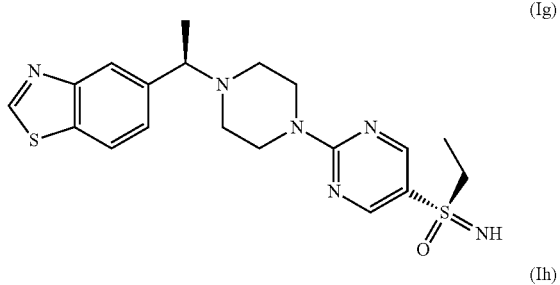
(Ig)

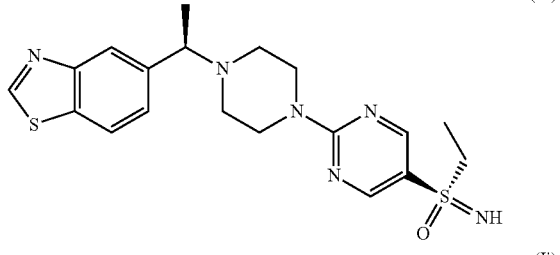
(Ih)

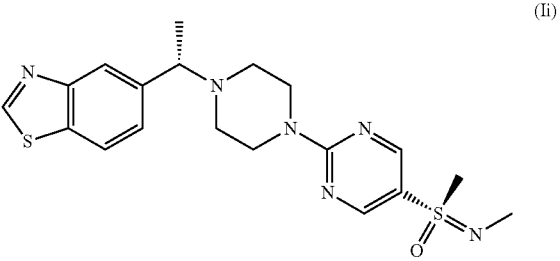
(Ii)

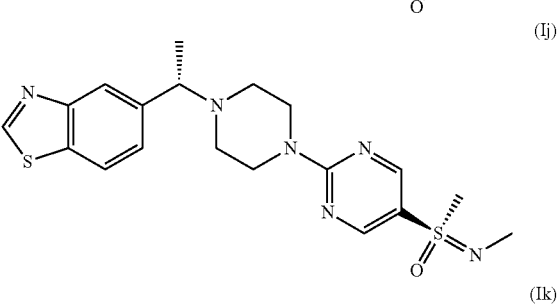
(Ij)

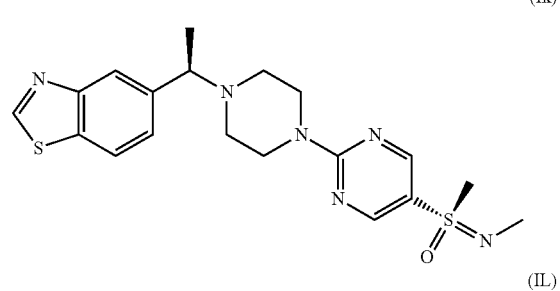
(Ik)

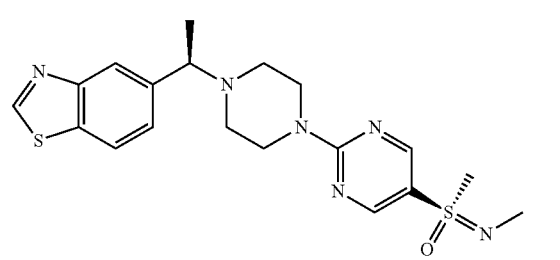
(IL)

Compound Ia and its solid forms are most preferred.

The compounds of formula I are preferably employed as as single diastereromer and/or enantiomer in an enantiomeric excess, as measured by methods well known by one skilled in the art, of 10% or more, preferably 50% or more, and more preferably more than 95%, 96%, 98% or 99%.

The nomenclature as used herein for defining compounds, especially the compounds according to the invention, is in general based on the rules of the IUPAC-organization for chemical compounds and especially organic compounds. The compounds of invention have been named according to the standards used in the program AutoNom 2000 or ACD Lab Version 12.01 or Instant JChem Version: 15.12.7.0.

Succinic acid and fumaric acid addition salts of the present invention can be obtained in different molar ratios. It has been found that the mono acid addition salts of the present invention, i.e. succinic acid or fumaric acid additions salts that have a molar ratio of the compounds of formula I to the respective acid of 1 to 1 are especially preferred and stable, soluble and/or show other improved properties.

A preferred method of preparation of the acid addition salts of compounds of formula I according to the invention comprises the following steps:
  a) suspending or dissolving the compound of formula I and the succinic acid or fumaric acid in a suitable solvent or solvent mixture;
  b) heating the mixture obtained in step a) to a temperature of between about 30° C. to about the boiling point of the selected solvent, preferably between about 50° C. and about 100° C. and most preferably to about 60° C., to about 70° C. or to about 80° C. and allowing the mixture to cool to room temperature;
  c) optionally repeating step b) several times;
  d) separating and drying the solid thus obtained.

Suitable solvents for the method of preparation of the acid addition salts of the present invention are preferably water or alcohols such as methanol (MeOH), ethanol (EtOH), 1-propanol, 2-propanol (IPA), 1-butanol, 2-butanol, 2-methyl-1-propanol, 2-methyl-2-propanol, 1-pentanol, 3-methyl-1-butanol, 2,2-dimethyl-1-propanol, cyclopentanol, 1-hexanol, cyclohexanol, 1-heptanol, 1-octanol, 1-nonanol, 1-decanol, 2-propen-1-ol, ketones, such as acetone, esters, such as ethyl acetate, acetonitrile, ethers such as tetrahydrofurane (THF), aromatic hydrocarbones, such as toluene and homogeneous mixtures of the above solvents, such as MeOH/water e.g. as 50/50 (v/v) mixture or IPA/water, e.g. as 90/10 (v/v) mixture or MeCN/water, e.g. as 95/5 (v/v) mixture.

Pharmaceutical formulations can be administered in the form of dosage units, which comprise a predetermined amount of active ingredient per dosage unit. The concentration of the prophylactically or therapeutically active ingredient in the formulation may vary from about 0.1 to 100 wt %. Preferably, the acid addition salts of the compounds of formula I or the pharmaceutically are administered in doses of approximately 0.5 to 1000 mg, more preferably between 1 and 700 mg, most preferably 5 and 100 mg per dose unit, calculated on the respective base. Generally, such a dose range is appropriate for total daily incorporation. In other terms, the daily dose is preferably between approximately 0.02 and 100 mg/kg of body weight.

Preferably the daily dose, i.e. the sum of all doses given to a patient during a given day, of a compound of formula I and preferably Ia is between about 20 and about 300 mg, more preferably between about 100 mg and 300 mg calculated on the respective base, such as about 200, 225 or 270 given once daily, or 50, 70 or 100 mg given twice daily, preferably orally adminstered. The acid addition salts of the present invention are preferably orally administered.

The following embodiments are related to the use of the acid addition salts of the invention:

1. Acid addition salts according to the invention for use in a treatment of a condition selected from neurodegenerative diseases, diabetes, cancer, cardiovascular diseases and stroke.
2. Acid addition salts according to embodiment 1 for use in a treatment of a condition, wherein the condition is selected from the group of one or more tauopathies and Alzheimer's disease, Dementia, Amyotrophic lateral sclerosis (ALS), Amyotrophic lateral sclerosis with cognitive impairment (ALSci), Argyrophilic grain disease, Behavioural variant frontomeporal dmenetia (BvFTD), Bluit disease, Chronic traumatic encephalopathy, Corticobasal degeneration (CBP), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Frontotemporal lobar degeneration (FTLD), Ganglioglioma, Gangliocytoma, Gerstmann-Straussler-Scheinker disease, Globular glia tauopathy, Guadeloupean parkinsonism, Hallevorden-Spatz disease (neurodegeneration with brain iron accumulation type 1), Lead encephalopathy, Lipofuscinosis, Meningioangiomatosis, Multiple system atrophy, Myotonic dystrophy, Niemann-Pick disease (type C), Pallido-ponto-nigral degeneration, Parkinsonism-dementia complex of Guam, Pick's disease (PiD), Parkinson's disease dementia, Postencephalitic parkinsonism (PEP), Primary progressive aphasia, Prion diseases (including Creutzfeldt-Jakob Disease (CJD), Progressive nonfluent aphasia, Variant Creutzfeldt-Jakob Disease (vCJD)(, Fatal Familial Insomnia, Kuru, Progressive supercortical gliosis, Progressive supranuclear palsy (PSP), Semantic dementia, Steele-Richardson-Olszewski syndrome, Subacute sclerosing panencephalitis, Tangle-only dementia, Tuberous sclerosis, Huntington's disease and Parkinson's disease, preferably one or more tauopathies and Alzheimer's disease.
3. A method for treating a tauopathy, wherein an acid addition salt according to the invention is administered to a mammal in need of such treatment.
4. A method for inhibiting a glycosidase, wherein a system expressing the glycosidase is contacted with an acid addition salt of hydrochloric acid, maleic acid or tartraic acid with acid addition salt according the invention under in-vitro conditions such that the glycosidase is inhibited.

Preparation of Compounds of Formula I

Preferred forms of the acid addition salts of the present invention demonstrate adequate properties for use as a drug. In particular, such preferred compounds show a high solid state stability, high stability in the presence of liver microsome, high oxidation stability and suitable permeability. Further preferred compounds of the present invention demonstrate their suitability as drugs by potent biological activity, such as the level of O-GlcNAcylation of total proteins measured in brain extracts. Relevant tests for determining such parameters are known by the person skilled in the art, e.g. solid state stability (Waterman K. C. (2007) *Pharm Res* 24(4); 780-790), stability in the presence of liver microsome (Obach R. S. (1999) *Drug Metab Dispos* 27(11); 1350-135) and the permeability (e.g. Caco-2 permeability assay, Calcagno A. M. (2006) *Mol Pharm* 3(1); 87-93). Compounds of the present invention that show a high potency in OGA inhibition assays and one or more of the above properties are especially suitable as a drug for the indications mentioned in the present specification.

The compounds according to formula (I) and the starting materials for its preparation, respectively, are produced by methods known per se, as described in the literature, i.e. under reaction conditions that are known and suitable for said reactions.

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The following abbreviations refer respectively to the definitions below:

Ac (acetyl), aq (aqueous), h (hour), g (gram), L (liter), mg (milligram), MHz (Megahertz), μM (micromolar), min (minute), mm (millimeter), mmol (millimole), mM (millimolar), m.p. (melting point), equiv (equivalent), mL (milliliter), μL (microliter), ACN (acetonitrile), AcOH (acetic acid), BINAP (2,2'-bis(disphenylphosphino)-1,1'-binaphthalene, BOC (tert-butoxy-carbonyl), CBZ (carbobenzoxy), CDC$_3$ (deuterated chloroform), CD$_3$OD (deuterated methanol), CH$_3$CN (acetonitrile), c-hex (cyclohexane), DCC (dicyclohexyl carbodiimide), DCM (dichloromethane), dppf (1,1'-bis(diphenylphosphino)ferrocene), DIC (diisopropyl carbodiimide), DIEA (diisopropylethyl-amine), DMF (dimethylformamide), DMSO (dimethylsulfoxide), DMSO-d$_6$ (deuterated dimethylsulfoxide), EDC (1-(3-dimethyl-amino-propyl)-3-ethylcarbodiimide), ESI (Electro-spray ionization), EtOAc (Ethyl acetate), Et$_2$O (diethyl ether), EtOH (ethanol), FMOC (fluorenylmethyloxycarbonyl), HATU (dimethylamino-([1,2,3]triazolo[4,5-b]pyridin-3-yloxy)-methylene]-dimethylammonium hexafluorophosphate), HPLC (High Performance Liquid Chromatography), i-PrOH (2-propanol), K$_2$CO$_3$ (potassium carbonate), LC (Liquid Chromatography), MD Autoprep (Mass directed Autoprep), MeOH (methanol), MgSO$_4$ (magnesium sulfate), MS (mass spectrometry), MTBE (Methyl tert-butyl ether), Mtr. (4-Methoxy-2,3,6-trimethylbenzensulfonyl), MW(microwave), NBS (N-bromo succinimide), NaHCO$_3$ (sodium bicarbonate), NaBH$_4$ (sodium borohydride), NMM (N-methyl morpholine), NMR (Nuclear Magnetic Resonance), POA (phenoxyacetate), Py (pyridine), PyBOP® (benzotriazole-1-yloxy-tris-pyrrolidino-phosphonium hexafluorophosphate), RT (room temperature), Rt (retention time), SFC (supercritical fluid chromatography), SPE (solid phase extraction), T3P (propylphosphonic anhydride), TBAF (tetra-n-butylammonium fluoride), TBTU (2-(1-H-benzotriazole-1-yl)-1,1,3,3-tetramethyluromium tetrafluoro borate), TEA (triethylamine), TFA (trifluoroacetic acid), THF (tetrahydrofurane), TLC (Thin Layer Chromatography), UV (Ultraviolet).

In general, the compounds according to Formula (I) and related formulae of this invention may be prepared from readily available starting materials. If such starting materials are not commercially available, they may be prepared by standard synthetic techniques. In general, the synthesis pathways for any individual compound of Formula (I) and related formulae will depend on the specific substituents of each molecule, such factors being appreciated by those having ordinary skill in the art. The following general methods and procedures described hereinafter in the examples may be employed to prepare compounds of Formula (I) and related formulae. Reaction conditions depicted in the following schemes, such as temperatures, solvents, or co-reagents, are given as examples only and are not restrictive. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by a person skilled in the art, using routine optimisation procedures. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

A "leaving group" LG denotes a chemical moiety which can be removed or replaced by another chemical group. Throughout the specification, the term leaving group preferably denotes Cl, Br, I or a reactively modified OH group, such as, for example, an activated ester, an imidazolide or alkylsulfonyloxy having 1 to 6 carbon atoms (preferably methylsulfonyloxy or trifluoromethylsulfonyloxy) or arylsulfonyloxy having 6 to 10 carbon atoms (preferably phenyl- or p-tolylsulfonyloxy). When a leaving group LG is attached to an aromatic or heteroaromatic ring, LG can denote in addition SO$_2$-alkyl or F. Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart). Activated esters are advantageously formed in situ, for example through addition of HOBt, N-hydroxysuccinimide or HATU.

Compound of formula (I) can be separated its corresponding other enantiomer by chiral chromatography or by chiral resolution, re-crystallization with use of an optically active acid.

Preferred chiral acids used for the chiral resolution of compounds of formula I are selected from but not limited to. These acids are preferably employed, as the desired diastereomeric salts are crystallizing. Preferably, between about 0.5 and about 2 equivalents of chiral acid are used for the selective crystallization. Solvents and solvent mixtures that are preferably used for the chiral resolution with chiral acids, are H$_2$O, MeCN (Acetonitril), about 2 to about 50% H$_2$O in EtOH (Ethanol), EtOH, 2 to 50% H$_2$O in MeOH (methanol), MeOH, 2 to 50% H$_2$O in IPA (isopropyl alcohol), IPA, 2 to 50% MeOH in MEK (methyl ethyl ketone, 2-butanone), MEK, 2 to 50% MeOH in iPrOAc (isopropyl acetate), iPrOAc, dioxane. All percentages for solvent mixtures are given in volume percent, if not indicated otherwise.

Preferably, methods known by one skilled in the art are used in the preparation. Further methods of preparation are as described below in the examples. Depending on the nature of Y, T and X, different synthetic strategies may be selected for the synthesis of compounds of Formula (I). In the process illustrated in the following schemes, Y, T and X are as above-defined in the description unless otherwise mentioned.

Compounds of Formula (I), wherein Y, T and X are defined as above, can be prepared from alternative compounds of Formula (I), using suitable interconversion procedures such as those described hereinafter in the examples, or conventional interconversion procedures well known by one skilled in the art.

Compound of formula (I) can be separated into compounds of formula (IA) and (IB) by chiral chromatography or by chiral resolution, re-crystallization with use of an optically active acid, using methods known by one skilled in the art and as described below in the examples (Scheme 1).

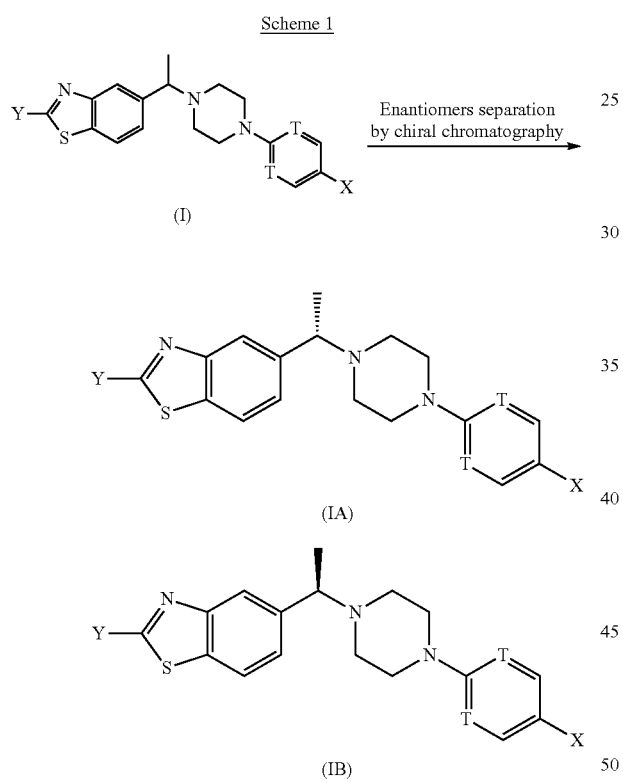

Compounds of formula (I), wherein Y, T and X are defined as above, can be prepared by the addition of an amine of formula (II) to a heterocycle of formula (III), where LG is a leaving group as defined above. This addition can be performed under thermic conditions, heating both compounds at a temperature between 50° C. and 200° C., using regular heating or microwave irradiation, in the presence of a base, such as but not limited to TEA, DIEA, $K_2CO_3$ or $Cs_2CO_3$, in a polar solvent, e.g. DMF, DMA or NMP. Alternatively, this addition can be catalysed by a metal complex, such as but not limited to $PdCl_2$, $Pd(OAc)_2$, $Pd_2(dba)_3$ in the presence of a ligand, e.g. BINAP, o-$Tol_3P$, X-Phos, and a base, e.g. NaOtBu, $Cs_2CO_3$ or $K_2CO_3$, in a suitable solvent or solvent mixture, for example dioxane, Toluene/MeOH, at a temperature between RT to 150° C., preferably at RT, for a few hours, e.g. one hour to 24 h (Scheme 2). Amine of formula (II) is obtained after deprotection of compound (IVa). PG is a suitable protecting group, which is compatible with the chemistry described below, such as but not limited to BOC. It can be removed under acidic conditions, such as but not limited to HCl in MeOH or dioxane or TFA in DCM, yielding isolation of amine (II).

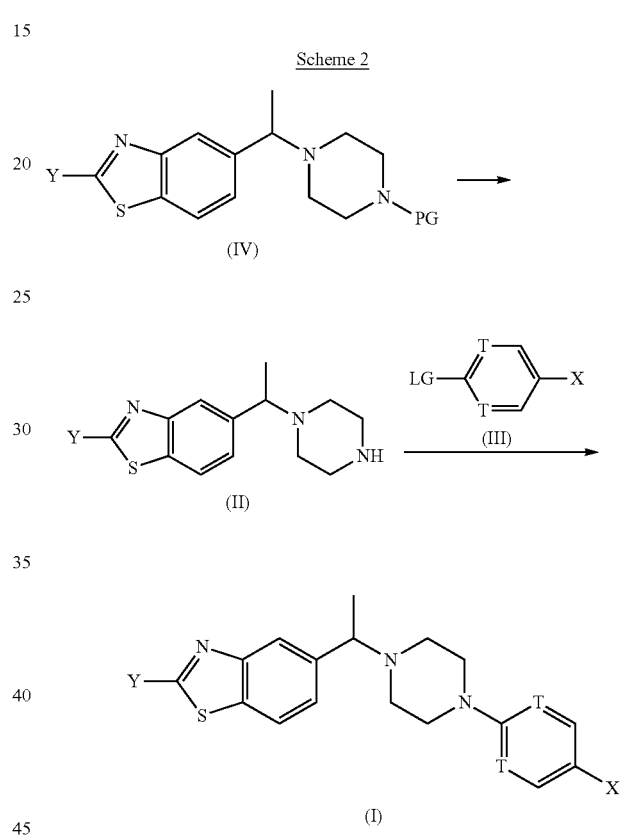

Compound of formula (IV), wherein PG is a protecting group, can be prepared from the corresponding ketone (IX) by reductive amination with amine (VI), using conditions known to the one skilled in the art, such as but not limited to the use of $NaBH(OAc)_3$ as reducing agent, in the presence of one equivalent of AcOH in DCE. Alternatively, reductive amination can be performed in two steps, with first imine formation, that can be catalysed by $Ti(OiPr)_4$, followed by reduction with suitable reducing agent, such as but not limited to $NaBH_4$ in MeOH (Abdel-Magid, A. F. at al. *J. Org. Chem.* 1996, 61, 3849-3862). Alternatively, ketone (IX) can be reduced into the corresponding alcohol (VIII) using usual reductive agents such as $NaBH_4$ in an alcoholic solvent, such as MeOH. Alcohol functionality can be then transformed into a suitable leaving group, such as but not limited to Cl or OMs, using conditions known to a person skilled in the art. The addition of amine (VI) to intermediate (VII) would yield the formation of compound (IV).

Scheme 3

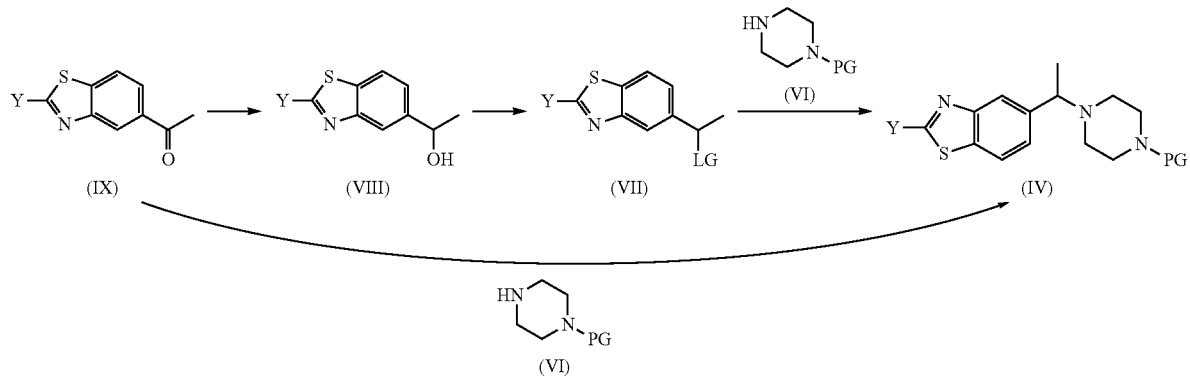

Alternatively, compound of formula (X), wherein PG is a suitable protecting group, such as but not limited to BOC, can be prepared from the addition of amine (XI) to an heterocycle of formula (III), where LG is a leaving group as defined above. This addition can be performed under thermic conditions or can be catalysed by a metal complex, using conditions known by a person skilled in the art and as described below in the examples (Scheme 4).

PG is a suitable protecting group, which is compatible with the chemistry described above, such as but not limited to BOC. It can be removed under acidic conditions, such as but not limited to HCl in MeOH or dioxane or TFA in DCM, yielding isolation of amine (XIV). It can be further transformed into compound of formula (I) by reductive alkylation with ketone of formula (IX), following conditions well known by a person skilled in the art, as described in the examples (Abdel-Magid, A. F. at al. *J. Org. Chem.* 1996, 61, 3849-3862). Alternatively, amine (XIV) addition to compound (VII), prepared as described above and in the examples, would yield the formation of compound of formula (I).

Scheme 4

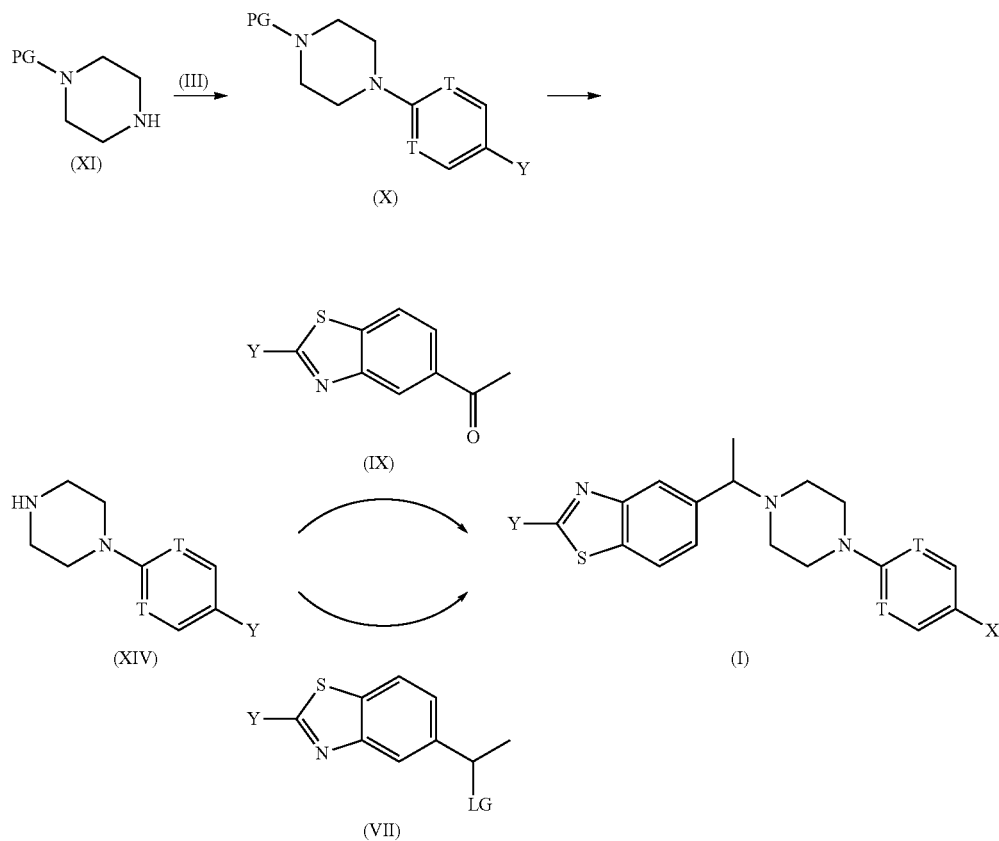

Amine of formula (II) can be separated into amines of formula (IIa) and (IIb) by chiral chromatography or chiral resolution by re-crystallization with an optically active acid, using methods known by one skilled in the art and as described below in the examples (Scheme 5).

Scheme 5

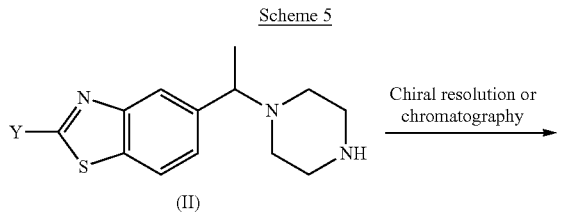

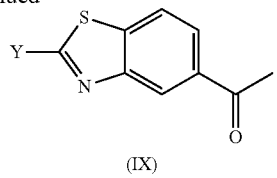

The sulfoximine group as indicated in the definition of X can be introduced or generated at any stage of the synthesis of compounds of formula (I), as described below in the examples.

General synthetic routes for the preparation of sulfoximines are described in Scheme 7, wherein $G^1$ and $G^2$ together denote the rest of the compound of formula I:

Scheme 7

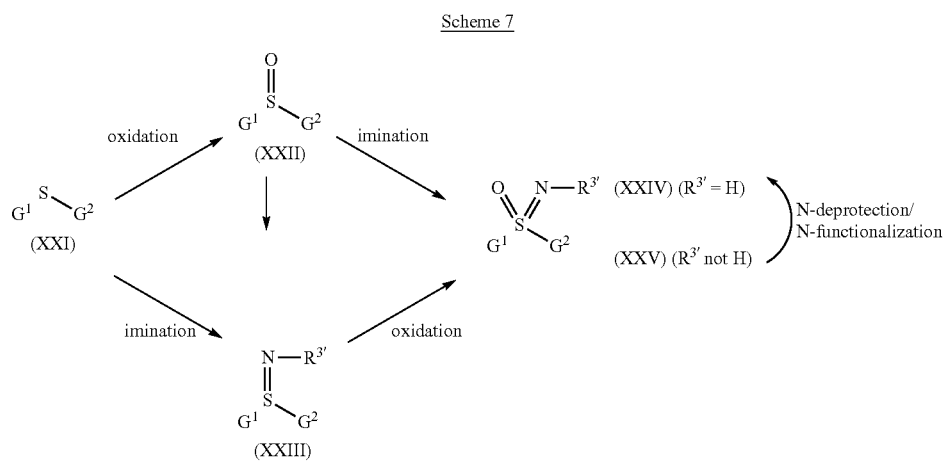

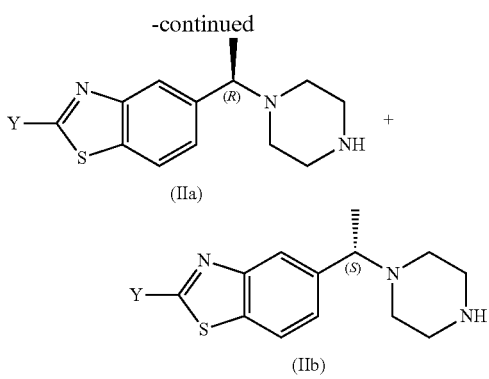

In another process, ketone of formula (IX) can be obtained by Stille cross coupling reaction between aryl halide (XX) and tributyl(1-ethoxyvinyl)tin in the presence of a catalyst, such as but not limited to $Pd(PPh_3)_2Cl_2$ in toluene at temperatures ranging from RT to 110° C. (Scheme 6).

Scheme 6

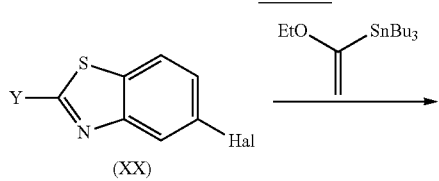

Typical synthesis of sulfoximines starts with the oxidation of a sulfide (XXI) followed by the imination of the resulting sulfoxide (XXII). Rhodium-catalyzed imination usually result in N-protected sulfoximines (XXV) ($R^{3'}$=protecting group) which can be then deprotected, yielding free NH-sulfoximines (XXIV) ($R^{3'}$=H). Metal-catalyzed imination of sulfoxides (XXII) or sulfide (XXI) can also be achieved with alternative metals, such as but not limited to copper, iron, manganese or ruthenium complexes. Iminations of sulfoxide (XXII) using in situ generated hydrazoic acid, activated reagents such as O-mesitylenesulfonylhydroxylamine (MSH) or O-(2,4-dinitrophenyl)-hydroxylamine (DPH) or ammonium carbamate in the presence of diacetoxyiodobenzene [PhI(OAc)₂], lead directly to the free sulfoximine (XXIV) ($R^{3'}$=H). N-Functionalized sulfoximine XXV ($R^{3'}$ ≈H) can be prepared from the free NH-sulfoximines (XXIV) ($R^{3'}$=H) by methods such as Cu-catalyzed arylations, nucleophilic substitutions or reductive alkylation. Alternatively, sulfoximines (XXV) ($R^{3'}$≈H) can also be obtained by oxidation of sulfilimines (XXIII), which are accessible by imination of sulfides (XXI) or transformation of sulfoxides (XXII) (Frings, M. et al. *Eur. J. Med. Chem.* 2017, 126, 225-245 and cited references).

Sulfoximines (XXIV) or (XXV) can be separated into compounds of formula (XXIVa) and (XXIVb) or (XXVa) and (XXVb) by chiral chromatography or by chiral resolution, re-crystallization with use of an optically active acid, using methods known by one skilled in the art and as described below in the examples (Scheme 8).

Alternatively, sulfoxide (XXII) can be separated into compounds of formula (XXIIa) and (XXIIb) by chiral chromatography or by chiral resolution, using methods known by one skilled in the art and as described below in the examples (Scheme 8).

Scheme 9

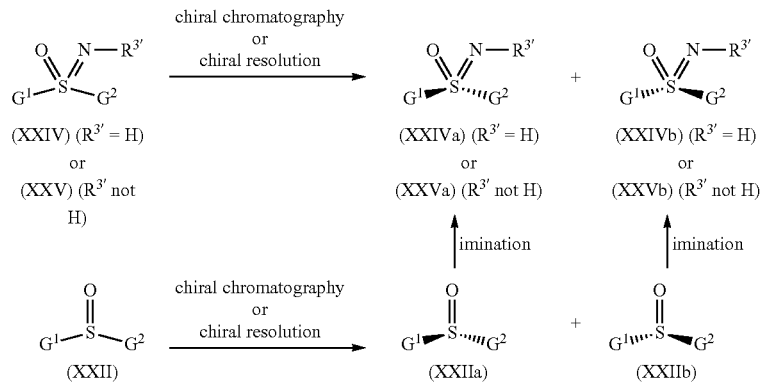

Chiral sulfoxide of formula (XXIIa) and (XXIIb) can be transformed into chiral sulfoximine of formula (XXIVa) and (XXIVb) respectively or (XXVa) and (XXVb) respectively. Stereospecific transformation with retention of configuration can be achieved by rhodium-catalyzed imination and subsequent deprotection (H. Okamura et al. *Organic Letters* 2004, 6, 1305-1307) or imination with ammonium carbamate and PhI(OAc)$_2$ in MeOH, affording directly (XXIVa) and (XXIVb) (M. Zenzola et al. *Angew. Chem. Int. Ed.* 2016, 55, 7203-7207).

The main routes to chiral sulfoxides are depicted in Scheme 9. The resolution of a racemic mixture (route i) is one possible method used to produce chiral sulfoxides, by either a chemical approach or an enzymatic reaction. Transformation of a diastereochemically pure sul nate is an alternative route affording sulfoxides with high enantiomeric excess (ee) values (route ii). The enantioselective oxidation of prochiral sul des (XXI) by enzymatic or non-enzymatic methods represents a relatively direct way (route iii) to prepare enantioenriched sulfoxides. Another preparative method (route iv) is to modify the structure of some chiral sulfoxides without any loss of stereochemistry at the sulfur atom (Organosulfur chemistry in asymmetric synthesis, Takeshi Toru; 2008).

Scheme 9

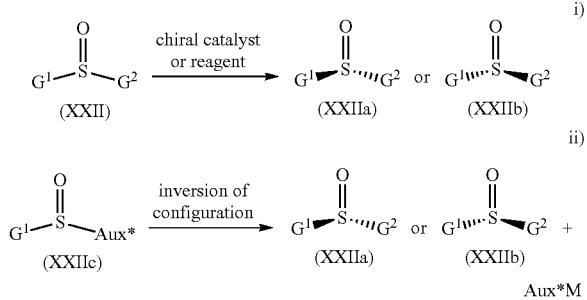

Aux* = chrial nucleofuge
G$^2$M = organometallics

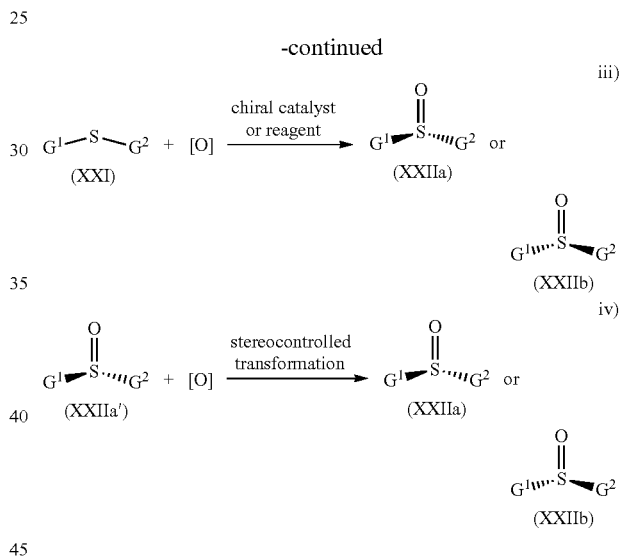

One approach for enantioselective oxidation of prochiral sul des (XXI) into chiral sulfoxide of formula (XXIIa) or (XXIIb) is using chiral transition metal complexes in combination with an oxidant (route ii). Typically, it is involving a metal such as but not limited to Ti(i-PrO)$_4$, in stoechiometric or catalytic amount, a chiral ligand selected from diethyl tartrate, madelic acid, binaphthol, dibromo-binaphthol, hydrobenzoin, or any other ligand known by a persone skilled in the art, an oxidant, such as but not limited to cumene hydroperoxide, tert-butyl hydroperoxide, H$_2$O$_2$, with the optional addition of water or a tertiary amine, such as i-Pr$_2$NEt, N-methylmorpholine or 1,4-dimethyl-piperazine (G. E. O'Mahony et al. *Arkivoc* 2011 (i) 1-110; J. Legros et al. *Adv. Synth. Catal.* 2005, 347, 19-31). Alternative metals, such as but not limited to Mn, V, Fe or W in the presence of a chiral ligand can also be used (G. E. O'Mahony et al. *Arkivoc* 2011 (i) 1-110; J. Legros et al. *Adv. Synth. Catal.* 2005, 347, 19-31). Chemoselective and enantioselective catalytic oxidation of heteroaromatic sulphides can be achieved in various degrees of selectivities with a manganese complex bearing a chiral ligand, such as porphyrin-like ligands, in the presence of a carboxylic acid, such as adamantine carboxylic acid and an oxidant such as but not limited to $H_2O_2$(Dai, W. et al. ACS catal. 2017, 7, 4890-4895). Further purification may be applied to achieve suitable enantiomeric purities.

Alternatively, kinetic resolution of sulfoxide of formula (XXII) into sulfone (XXVI) can be achieved under similar conditions and according to well-known methods, leaving one enantioenriched sulfoxide unchanged (G. E. O'Mahony et al. Arkivoc 2011 (i) 1-110).

When a reaction is preferably performed under basic conditions, a suitable base might be selected from metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia), alkaline metal carbonates (e.g., sodium bicarbonate) and several organic bases (e.g., N,N-diisopropylethylamine, piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid, acetic acid or trifluoroacetic acid (TFA); nitro compounds, such as nitromethane or nitrobenzene; esters, such as ethyl acetate, or mixtures of the said solvents. Particular preference is given to TFA, DMF, dichloromethane, THF, $H_2O$, methanol, tert. butanol, tert. amylalcohol, triethylamine or dioxane.

Depending on the conditions used, the reaction time is between a few minutes and 14 days, the reaction temperature is between about −80° C. and 140° C., normally between −50° C. and 120° C., preferably between −20° C. and 100° C.

BRIEF DESCRIPTION OF THE DRAWINGS

The present invention is further illustrated by reference to the accompanying figures:

FIG. 1: Characteristic X-ray powder diffraction pattern of crystalline Example 35 succinate salt, Form 1

FIG. 2: Characteristic 1H NMR spectrum of crystalline Example 35 succinate salt, Form 1

FIG. 3: Characteristic STA thermogram of crystalline Example 35 succinate salt, Form 1

FIG. 4: Characteristic X-ray powder diffraction pattern of crystalline Example 35 fumarate salt FIG. 5: Characteristic 1H NMR spectrum of crystalline Example 35 fumarate salt FIG. 6: Characteristic STA thermogram of crystalline Example 35 fumarate salt FIG. 7: Characteristic X-ray powder diffraction pattern of crystalline Example 35 succinate salt, Form 2

FIG. 8: Characteristic 1H NMR spectrum of crystalline Example 35 succinate salt, Form 2

FIG. 9: Characteristic X-ray powder diffraction pattern of crystalline Example 35 hydrochloride salt FIG. 10: Characteristic STA thermogram of crystalline Example 35 hydrochloride salt FIG. 11: Characteristic X-ray powder diffraction pattern of crystalline Example 35 benzoate salt FIG. 12: Characteristic 1H NMR spectrum of crystalline Example 35 benzoate salt

EXPERIMENTAL PART

Preparation of Compounds

The compounds according to Formula (I) can be prepared from readily available starting materials by several synthetic approaches, using both solution-phase and solid-phase chemistry protocols or mixed solution and solid phase protocols. Examples of synthetic pathways are described below in the examples. All reported yields are non-optimized yields. Unless otherwise stated, compounds of Formula (I) and related formulae obtained as a racemic mixture can be separated to provide an enantiomerically enriched mixture or a pure enantiomer.

The commercially available starting materials used in the following experimental description were purchased from Aldrich, Sigma, ACROS, ABCR, Combi-Blocks, Matrix, Apollo scientific, Alfa Aesar, etc. unless otherwise reported.

The HPLC, MS and NMR data provided in the examples described below are obtained as followed:

$^1$H NMR analyses were carried out using BRUKER NMR, model AV-II and AV-III 400 MHz FT-NMR. Residual signal of deuterated solvent was used as internal reference. Chemical shifts (δ) are reported in ppm in relative to the residual solvent signal (δ=2.50 for $^1$H NMR in DMSO-$d_6$, and 7.26 in $CDCl_3$). s (singlet), d (doublet), t (triplet), q (quadruplet), br (broad), quint (quintuplet).

LCMS Analysis Condition:
Instrument name: Agilent Technologies 1290 infinity 11.
Method A: Method: A-0.1% TFA in $H_2O$, B-0.1% TFA in ACN; flow rate: 2.0 mL/min; column: XBridge C8 (50×4.6 mm, 3.5 μm), +ve mode
Method B: Method: A-10 mM $NH_4HCO_3$ in $H_2O$, B-ACN; flow rate: 1.0 mL/min; column: XBridge C8 (50×4.6 mm, 3.5 μm), +ve mode
Method C: Method: A-0.1% HCOOH in $H_2O$, B-ACN; flow rate: 1.5 ml/min; column: ZORBAX Eclipse XDB-C18 (50×4.6 mm, 3.5 μm), +ve mode HPLC analysis condition:
Instrument name: Agilent 1200 Series instruments as followed using % with UV detection (maxplot).
Method A: Method: A-0.1% TFA in $H_2O$, B-0.1% TFA in ACN; flow rate: 2.0 mL/min; column: XBridge C8 (50×4.6 mm, 3.5 μm).
Method B: Method: A-10 mM $NH_4HCO_3$ in $H_2O$, B-ACN; flow rate: 1.0 mL/min; column: XBridge C8 (50×4.6 mm, 3.5 μm).

Chiral HPLC Analysis Condition:
Instrument name: Agilent 1260 infiinity II
Method A: Mobile Phase: 0.1% DEA in n-Hexane: EtOH: 60:40; flow rate: 1.0 mL/min; column: Chiralcell OD-H (250×4.6 mm, 5 μm).

Chiral SFC Analysis Condition:
Instrument name: THAR-SFC 80 and THAR-SFC 200 (analytical)
Ratio between $CO_2$ and co-solvent is ranging between 60:40 and 80:20

Method A: Mobile Phase: 20 mM ammonia in IPA, flow rate: 4 mL/min; column: Chiralpak ADH (250×4.6 mm, 5 μm).

Method B: Mobile Phase: 20 mM ammonia in methanol, flow rate: 10 mL/min; column: YMC Cellulose C (250×4.6 mm, 5 μm).

Method C: Mobile Phase: 20 mM ammonia in IPA, flow rate: 4 mL/min; column: Lux A1 (250×4.6 mm, 5 μm).

Method D: Mobile Phase: 20 mM ammonia in MeOH, flow rate: 4 mL/min; column: Chiralpak ADH (250×4.6 mm, 5 μm).

Method E: Mobile Phase: IPA, flow rate: 3 mL/min; column: Lux A1 (250×4.6 mm, 5 μm).

Prep-HPLC Analysis Condition:

Method A: A-0.1% TFA in $H_2O$, B-MeOH or CAN; column: Sunfire C8 (19×250 mm, 5 μm) or Sunfire C18 (30×250 mm, 10 μm).

Method B: A-10 mM $NH_4HCO_3$ in $H_2O$, B-MeOH or ACN, Column: Sunfire C8 (19×250 mm, 5 μm) or Sunfire C18 (30×250 mm, 10 μm).

Chiral Preparative SFC Analysis Condition:

Instrument name: THAR-SFC 80, THAR-SFC 200 and PIC SFC 10-150

Ratio between $CO_2$ and co-solvent is ranging between 60:40 and 80:20

Method A: Mobile Phase: 20 mM ammonia in IPA; flow rate: 3 mL/min; column: Chiralpak ADH (250×30 mm, 5 μm).

Method B: Mobile Phase: 20 mM ammonia in methanol; flow rate: 5 mL/min; column: YMC Cellulose C (250×30 mm, 5 μm).

Method C: Mobile Phase: 20 mM ammonia in IPA; flow rate: 5 mL/min; column: Lux A1 (250×30 mm, 5 μm).

Method D: Mobile Phase: 20 mM ammonia in MeOH; flow rate: 4 mL/min; column: Chiralpak ADH (250×30 mm, 5 μm).

Method E: Mobile Phase: IPA, flow rate: 100 mL/min; column: Phenomenex Lux Amylose-1 (250×30 mm, 5 μm).

General flash chromatography conditions used for the purification of intermediates or compounds of Formula I: silica gel 230-400 mesh; gradients used as eluent: 10 to 80% EtOAc in petroleum ether or 1 to 15% MeOH in DCM.

The microwave chemistry was performed on a single mode microwave reactor Initiator™ Sixty from Biotage.

Specific Optical Rotation

Instrument name: Autopol VI, by Rudolph Research Analytical, Hackettstown, NJ, USA.

Synthesis

Intermediate 1: 5-(1-chloroethyl)benzo[d]thiazole

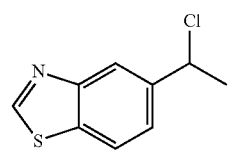

Step 1: 1-(benzo[d]thiazol-5-yl)ethan-1-one

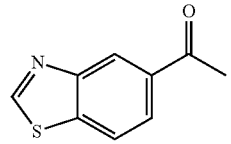

To a degased solution of 5-bromo benzothiazole (Combi-Blocks, 750 g, 3.51 mol) in dry toluene (6 L), 1-ethoxyvinyl tributyltin (1.42 L, 4.21 mol) followed by $Pd(PPh_3)_2Cl_2$ (105.6 g, 150.7 mmol) were added at RT and the resulting mixture was heated at 90° C. for 16 h. After completion of the reaction (monitored by TLC), the reaction mixture was cooled to RT, filtered through celite and washed with EtOAc (1 L). The filtrate was evaporated under vacuum and 5N HCl solution (2.5 L) was added to the crude mixture. The resulting light brown coloured solution was stirred at RT for 1.5 h, neutralized with the slow addition of a saturated $NaHCO_3$ (12 L) solution over 1 h at 0° C. and was extracted with EtOAc (2×5 L). The combined organic layer was washed with brine solution (2.5 L), dried over anhydrous $Na_2SO_4$ and evaporated under vacuum. The resulting crude material was dissolved in DCM (750 mL), hexane (3 L) was added to it and the resulting solid was filtered and the solids were washed with MTBE (4 L). The combined filtrate was concentrated under vacuum and the residue was dissolved in EtOAc (2.5 L). Charcoal (35 g) was added to the resulting solution. The organic layer was stirred for 6 h at RT and filtered and solids were washed with EtOAc (1 L). The organic layer was concentrated to afford the title compound. Yield: 79% (475 g, light brown solid). $^1H$ NMR (400 MHz, DMSO-$d_6$): δ 9.53 (s, 1H), 8.69 (s, 1H), 8.32 (d, J=8.4 Hz, 1H), 8.04 (dd, J=8.4, 1.3 Hz, 1H), 2.71 (s, 3H). LCMS: (Method C) 178.0 (M+H), Rt. 1.4 min, 98.5% (Max). HPLC: (Method A) Rt 2.6 min, 97.2% (Max).

Step 2: 1-(benzo[d]thiazol-5-yl)ethan-1-ol

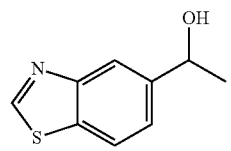

To a stirred solution of 1-(benzo[d]thiazol-5-yl)ethan-1-one (475 g, 2.68 mol)) in MeOH (4.75 L), $NaBH_4$ (152.28 g, 4.03 mol) was added portion wise at 0° C. and the reaction mixture was stirred at RT for 1 h. Completion of the reaction was monitored by TLC. The reaction mixture was then quenched with ice water (400 mL) at 0° C. and concentrated under vacuum. To the resulting crude mixture, water (2.5 L) was added and the aqueous layer was extracted with EtOAc (2×2.5 L). The combined organic layer was washed with brine (2 L), dried over anhydrous $Na_2SO_4$ and concentrated under vacuum. The resulting crude solid was triturated with hexane: diethyl ether (8:2) and decanted to afford the title compound. Yield: 93% crude (440 g, pale brown gummy solid). $^1H$ NMR (400 MHz, DMSO-$d_6$): δ 9.37 (s, 1H), 8.09 (d, J=8.4 Hz, 1H), 8.04 (s, 1H), 7.50 (d, J=1.2 Hz, 1H), 5.32 (d, J=4.0 Hz, 1H), 4.93-4.89 (m, 1H), 1.40 (d, J=6.4 Hz, 3H).

LCMS: (Method C) 180.1 (M+H), Rt. 1.2 min, 98.7% (Max). HPLC: (Method A) Rt. 2.2 min, 99.5% (Max).

Step 3: 5-(1-chloroethyl)benzo[d]thiazole

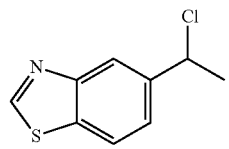

To a stirred solution of 1-(benzo[d]thiazol-5-yl)ethan-1-ol (440 g, 2.46 mol)) in DCM (4.4 L), thionyl chloride (534 mL, 7.37 mol) was added drop wise over 30 min at 0° C. and the reaction mixture was stirred for 1 h at 0-10° C. Completion of the reaction was monitored by TLC. The reaction mixture was then evaporated under vacuum. The resulting crude material was co-distilled with dry DCM (3×400 mL), dried under vacuum to afford title compound which was used in the next step without further purification. Yield: 100% crude (488 g, yellow solid). $^1$H NMR (400 MHz, DMSO-$d_6$): δ 10.79 (s, 1H), 8.52 (s, 1H), 8.16 (d, J=8.4 Hz, 1H), 7.86 (d, J=8.4 Hz, 1H), 5.30-5.24 (m, 1H), 1.91 (d, J=6.8 Hz, 3H). LCMS: (Method C) 198.1 (M+H), Rt. 2.0 min, 50.1% (Max). HPLC: (Method A) Rt. 3.9 min, 66.8% (Max).

Intermediate 2: 5-(1-chloroethyl)-2-methylbenzo[d]thiazole

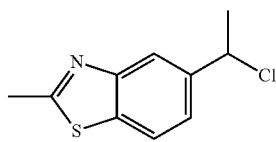

Step 1: 1-(2-methylbenzo[d]thiazol-5-yl)ethan-1-one

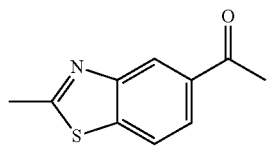

To a degased solution of 5-bromo-2-methylbenzo[d]thiazole (10 g, 43.85 mmol, Combi block) in dry toluene (40 mL), Pd(PPh$_3$)$_2$Cl$_2$ (3.07 g, 4.3 mmol) followed by 1-ethoxyvinyl tributyltin (16.2 mL, 48.2 mmol) were added and the reaction mixture was heated at 90° C. for 16 h. Completion of the reaction was monitored by TLC, the reaction mixture was then cooled to 0° C. and filtered through celite. The resulting filtrate was evaporated under vacuum, and then 6N HCl solution (80 mL) was added to the crude material. The reaction mixture was stirred at RT for 1 h, then neutralized by using NaHCO$_3$ and the aqueous layer was extracted with EtOAc (2×80 mL). The combined organic layer was dried over anhydrous Na$_2$SO$_4$ and evaporated under vacuum. The resulting crude material was purified by flash column chromatography (Biotage Isolera, eluent: 60-80% EtOAc in hexane). Yield: 72% (6 g, yellow solid). $^1$H NMR (400 MHz, DMSO-$d_6$): δ 8.48 (s, 1H), 8.18 (d, J=11.2 Hz, 1H), 7.95 (d, J=11.2 Hz, 1H), 2.85 (s, 3H), 2.67 (s, 3H). LCMS: (Method A) 192.3 (M+H), Rt. 2.9 min, 96.8% (Max).

Step 2: 1-(2-methylbenzo[d]thiazol-5-yl)ethan-1-ol

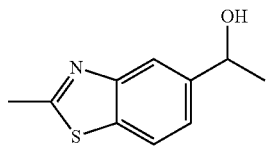

To a stirred solution of 1-(2-methylbenzo[d]thiazol-5-yl)ethan-1-one (6 g, 31.31 mmol) in MeOH (30 mL), NaBH$_4$ (2.37 g, 62.74 mmol) was added portion wise at 0° C. and the reaction mixture was stirred at RT for 1 h. Completion of the reaction was monitored by TLC, the reaction mixture was then quenched with ice and evaporated under vacuum. To the resulting reaction mixture, water (10 mL) was added and extracted with EtOAc (2×60 mL). The combined organic layer was dried over anhydrous Na$_2$SO$_4$ and evaporated under vacuum. The resulting crude material was purified by flash chromatography (Biotage Isolera, eluent: 70-90% EtOAc in hexane). Yield: 87% (5.3 g, brown solid). $^1$H NMR (400 MHz, DMSO-$d_6$): δ 7.94 (d, J=8.4 Hz, 1H), 7.86 (s, 1H), 7.38 (dd, J=8.2, 1.2 Hz, 1H), 5.28 (d, J=4.4 Hz, 1H), 4.90-4.80 (m, 1H), 2.79 (s, 3H), 1.38 (d, J=6.4 Hz, 3H). LCMS: (Method A) 194.2 (M+H), Rt. 2.5 min, 98.9% (Max).

Step 3: 5-(1-chloroethyl)-2-methylbenzo[d]thiazole

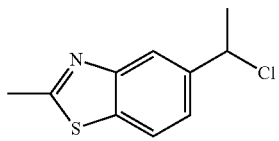

To a stirred solution of 1-(2-methylbenzo[d]thiazol-5-yl)ethan-1-ol (5.3 g, 27.4 mmol) in dry DCM (50 mL), thionyl chloride (4 mL, 54.8 mmol) was added drop wise at 0° C. and stirred at 25° C. for 1 h. Completion of the reaction was monitored by TLC, the reaction mixture was then concentrated under vacuum and co-distilled with toluene (10 mL). The resulting crude material was dried under high vacuum to afford the title compound which was used in the next step without further purification. Yield: 5.5 g (crude), brown oil. $^1$H NMR (400 MHz, DMSO-$d_6$): δ 8.05-8.01 (m, 2H), 7.53 (dd, J=8.4, 2.0 Hz, 1H), 5.51 (q, J=6.8 Hz, 1H), 2.81 (s, 3H), 1.86 (d, J=6.8 Hz, 3H). LCMS: (Method A) 212.2 (M+H), Rt. 4.26 min, 36.1% (Max).

Intermediate 6: 5-(1-(piperazin-1-yl)ethyl)benzo[d]thiazole

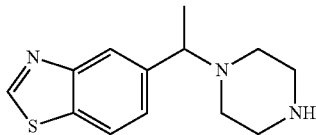 [SMILES: CC(c1ccc2scnc2c1)N1CCNCC1]

Step 1: tert-butyl 4-(1-(benzo[d]thiazol-5-yl)ethyl)piperazine-1-carboxylate

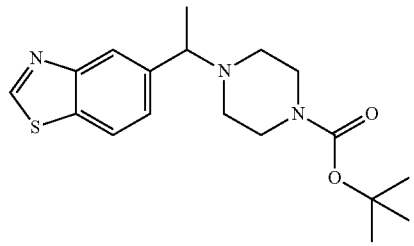 [SMILES: CC(c1ccc2scnc2c1)N1CCN(C(=O)OC(C)(C)C)CC1]

To a stirred solution of tert-butyl piperazine-1-carboxylate (522 g, 2.97 mol) and TEA (2.5 L, 17.34 mol) in DMF (2 L), Intermediate 1 (488 g, 2.48 mol) in DMF (3 L) was added dropwise at RT under $N_2$ atm and the reaction mixture was heated to 60° C. for 24 h. Completion of the reaction was monitored by TLC. The reaction mixture was then cooled to RT. To the resulting mixture, water (10 L) was added and the aqueous layer was extracted with EtOAc (6×2 L). The combined organic layer was washed with brine (2.5 L), dried over anhydrous $Na_2SO_4$ and concentrated under vacuum. The resulting crude material was purified by flash chromatography (silica gel: 60-120 mesh, eluent: 40% EtOAc in pet-ether) to afford the title compound. Yield: 81% (700 g, pale brown gummy solid). $^1$H NMR (400 MHz, DMSO-$d_6$): δ 9.39 (s, 1H), 8.11 (d, J=8.4 Hz, 1H), 7.99 (s, 1H), 7.47 (d, J=8.4 Hz, 1H), 3.45 (q, J=6.8 Hz, 1H), 3.34-3.29 (m, 4H), 2.37-2.27 (m, 4H), 1.41-1.18 (m, 12H). LCMS: (Method A) 348.1 (M+H), Rt. 1.6 min, 85.6% (Max). HPLC: (Method A) Rt. 2.89 min, 81.5% (Max).

Step 5: 5-(1-(piperazin-1-yl)ethyl)benzo[d]thiazole

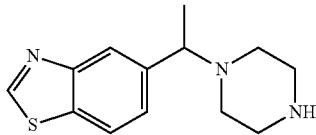 [SMILES: CC(c1ccc2scnc2c1)N1CCNCC1]

To a stirred solution of tert-butyl 4-(1-(benzo[d]thiazol-5-yl)ethyl)piperazine-1-carboxylate (700 g, 2.02 mol) in 1,4-dioxane (3 L), HCl solution in dioxane (3.50 L, 4M) was added dropwise at 0° C. and the resulting solution was stirred at RT for 6 h. After completion of the reaction (monitored by TLC), the reaction mixture was concentrated under vacuum and the resulting crude material was triturated with EtOAc (2×1 L). The hydrochloride salt was dissolved in water (2.5 L) and aqueous layer was washed with EtOAc (3×2 L) and DCM (3×2 L). The resulting aqueous layer was basified with 6N NaOH (pH~12) and extracted with EtOAc (3×2 L). The combined organic layer was washed with brine (500 mL), water (500 mL), dried over anhydrous $Na_2SO_4$ and concentrated under vacuum to afford the title compound. Yield: 70% (350 g, pale brown gummy solid). $^1$H NMR (400 MHz, DMSO-$d_6$): δ 9.38 (s, 1H), 8.10 (d, J=8.4 Hz, 1H), 7.98 (s, 1H), 7.46 (dd, J=8.4, 1.2 Hz, 1H), 3.33 (m, 1H), 3.58 (q, J=6.8 Hz, 1H), 2.71-2.68 (m, 4H), 2.37-2.27 (m, 4H), 1.19 (d, J=6.8 Hz, 3H). LCMS: (Method A) 248.1 (M+H), Rt. 0.88 min, 97.3% (Max). HPLC: (Method A) Rt. 1.6 min, 99.1% (Max).

Intermediate 7: (S)-5-(1-(piperazin-1-yl)ethyl)benzo[d]thiazole or (R)-5-(1-(piperazin-1-yl)ethyl)benzo[d]thiazole

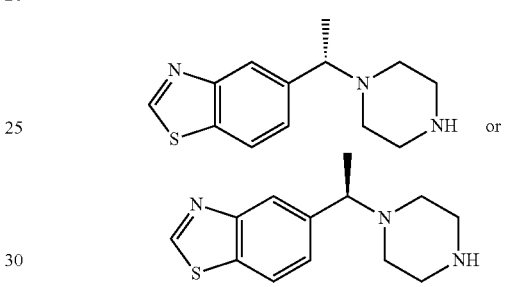

To a stirred mixture of intermediate 6 (100 g, 405.0 mmol) in EtOH (2 L, 20V), D-di-p-anisoyltartaric acid (42.31 g, 101.2 mmol) was added at RT and heated at 90° C. for 20 min. (Note: Salt formation was observed slowly after 3 to 5 min after addition of D-di-p-anisoyltartaric acid). Then the reaction mixture was stirred at RT overnight. The resulting mixture was filtered and the filtration cake was washed with EtOH (2×250 mL, 5V), diethyl ether (250 mL) and dried under high vacuum. To increase the ee, the salt (66 g, 79% ee) was further refluxed in EtOH (1 L, 10V) for 24 h and stirred at RT overnight. The obtained salt was filtered, washed with EtOH (200 mL, 2V), diethyl ether (200 mL) and dried under high vacuum. The same procedure was repeated to achieve the ee of 96.1% (21.2 g). This step was repeated on 300 g scale to obtain the salt (113.2 g).

The above obtained salts (134.4 g) were dissolved in water (300 mL), basified to pH~14 with 6N NaOH solution (350 mL) and the aqueous layer was extracted with EtOAc (2×1 L). The combined EtOAc layer was washed with brine solution (2×1 L), water (300 mL), dried over anhydrous $Na_2SO_4$ and concentrated under vacuum to obatin the title compound (enantiomer ratio 97.41:2.58%). Yield: 85% (63.0 g, pale brown gummy solid). $^1$H NMR (400 MHz, DMSO-d6): δ 9.38 (s, 1H), 8.09 (d, J=8.4 Hz, 1H), 7.97 (s, 1H), 7.45 (d, J=8.0 Hz, 1H), 3.55 (q, J=6.8 Hz, 1H), 2.67-2.66 (m, 4H), 2.34-2.25 (m, 4H), 1.34 (d, J=6.8 Hz, 3H). LCMS: (Method A) 248.2 (M+H), Rt. 1.5 min, 98.5% (Max). HPLC: (Method A) Rt. 1.6 min, 98.7% (Max). Chiral HPLC: (Method A) Rt. 11.1 min, 97.4% (Max).

Chiral resolution agent D-di-p-anisoyltartaric acid can be exchanged for D-di-p-toluyltartaric acid or (R)-(+)-chlocyphos to obtain the identical products.

Intermediate 6, dihydrochloride salt (15.57 g, 48.60 mmol) was mixed with sodium acetate trihydrate (26.45 g, 194.4 mmol, 400 mol %), R-(+)-chlocyphos (8.11 g, 29.32 mmol, 99% ee, 60.3 mol %), water (120 mL) and ethanol (16 mL). The mixture, becoming a thick suspension on stirring, was warmed up, resulting in a clear solution when it reached reflux temperature. The solution was allowed to cool with stirring and some seed crystals (small spatula, ca. 10-20 mg) were added about every 5-10 minutes, until crystallization started (between 5 and 10 times). Crystallization of the salt started at ca. 45° C. The suspension was stirred at 20° C. overnight, then filtered, the solid was washed with water/ethanol 10/1 (55 mL) and water (20 mL). It was dried for 2 d at 20° C. (11.12 g, 21.22 mmol, 44%). The ee was 97.5%.

This salt was heated under gentle reflux with water (90 mL) and ethanol (10 mL). Further ethanol (2 mL) was added, and the solution was allowed to cool to 20° C. and stirred for 6 h. The resulting solid was filtrated and washing with water (50 mL). After driing at 20° C. for 3 d, Chlorcyphos salt was isolated (9.50 g, 18.13 mmol, 37%). The ee was 100%.

The above obtained chlocyphos-salt with 100% ee (8.50 g, 16.22 mmol) was stirred for 1.5 h in a mixture of toluene (100 mL), water (50 mL), and sodium hydroxide (4.04 g, 101 mmol). Sodium chloride (20 g) was added and the mixture was stirred for 15 min, then filtered. The filtrate layers were separated. The solid isolated on the filter and in the aqueous layer were stirred with toluene (125 mL). It was filtered and the filtrate layers were separated again. The combined toluene layers were dried and evaporated at 60° C. to yield the desired free amine as a solidifying oil (3.60 g, 14.55 mmol, 90%, pure by NMR), and with 99.6% ee.

Intermediate 8: 2-methyl-5-(1-(piperazin-1-yl)ethyl) benzo[d]thiazole

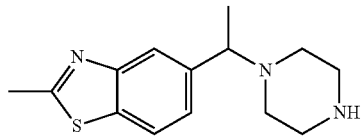 [SMILES: Cc1nc2cc(C(C)N3CCNCC3)ccc2s1]

Step 4: 2-methyl-5-(1-(piperazin-1-yl)ethyl)benzo[d]thiazole

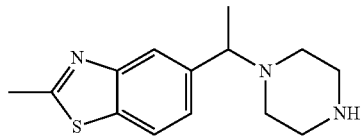 [SMILES: Cc1nc2cc(C(C)N3CCNCC3)ccc2s1]

To a stirred solution of piperazine (13.6 g, 15.9 mmol) in dry DCM (80 mL), Intermediate 2 (4.2 g, 19.8 mmol) was added dropwise over a period of 20 min and the reaction mixture was stirred at RT overnight. After completion of the reaction (monitored by TLC), water (50 mL) was added to the resulting mixture and stirred for 10 min. The organic layer was separated, washed with brine (50 mL), dried over anhydrous Na$_2$SO$_4$ and concentrated under vacuum. The resulting crude material was purified by flash chromatography (Biotage Isolera, eluent: 18-20% methanol in DCM) to afford the title compound. Yield: 16% (870 mg, pale brown gummy solid). $^1$H NMR (400 MHz, DMSO-d$_6$): δ 8.32 (s, 1H), 7.95 (d, J=8.6 Hz, 1H), 7.80 (s, 1H), 7.34 (d, J=8.8 Hz, 1H), 3.52-3.48 (m, 1H), 2.78 (s, 3H), 2.70 (t, J=6.0 Hz, 4H), 2.44-2.24 (m, 4H), 1.33 (d, J=8.8 Hz, 3H). LCMS: (Method A) 262.2 (M+H), Rt. 1.8 min, 97.3% (Max).

Intermediate 9: 2-Chloro-5-(methylsulfinyl)pyrimidine

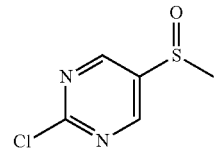

Step 1: 2-chloro-5-(methylthio)pyrimidine

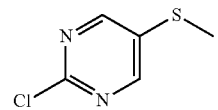

To a stirred solution of 5-bromo-2-chloropyrimidine (5 g, 25.8 mmol) and 1,2-dimethyldisulfane (2.92 g, 31.02 mmol) in THF (15 mL), n-BuLi (16.0 mL, 25.8 mmol, 1.6 M in hexane) was added at –78° C. and stirred for 1 h under the same temperature. Afer completion of the reaction (monitored by TLC), the reaction was then quenched with the addition of sat·NH$_4$Cl (15 mL) and the aqueous layer was extracted with EtOAc (50 mL). The organic layer was washed with water (10 mL), brine (10 mL) and dried over anhydrous Na$_2$SO$_4$. The resulting crude material was purified by flash chromatography (silica gel: 60-120 mesh, eluent: 15% EtOAc in pet ether) to afford the title compound. Yield: 13% (0.6 g, white solid). $^1$H NMR (400 MHz, CDCl$_3$): δ 8.50 (s, 2H), 2.56 (s, 3H). LCMS: (Method A) 161.1 (M+H), Rt. 2.1 min, 95.2% (Max). HPLC: (Method A) Rt. 2.4 min, 98.5% (Max).

Step 2: 2-chloro-5-(methylsulfinyl)pyrimidine

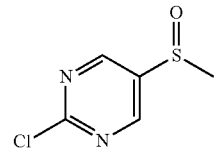

To a stirred solution of 2-chloro-5-(methylthio)pyrimidine (0.6 g, 2.49 mmol) in DCM (2 mL, 10 V), m-CPBA (0.644 g, 3.23 mmol) was added portion wise at 0° C. for 30 min. Completion of the reaction was monitored by TLC, the reaction mixture was then quenched with 10% NaHCO$_3$ solution and extracted with DCM (2×100 mL). The combined organic layer was washed with brine (30 mL), dried over anhydrous Na$_2$SO$_4$ and concentrated under vacuum. The resulting crude material was purified by flash chromatography (Biotage Isolera, eluent: 10-12% EtOAc in pet ether) to afford the title compound. Yield: 33% (330 mg, off white solid). $^1$H NMR (400 MHz, DMSO-d$_6$): δ 8.88 (s, 2H), 2.92 (s, 3H). LCMS: (Method A) 177.1 (M+H), Rt. 0.8 min, 99.1% (Max). HPLC: (Method A) Rt. 1.9 min, 99.6% (Max).

Intermediate 10: N-((2-chloropyrimidin-5-yl)(methyl)(oxo)-λ⁶-sulfanylidene)-2,2,2-trifluoroacetamide

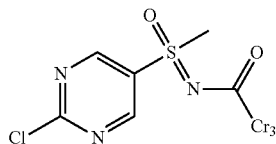

To a stirred solution of Intermediate 9 (0.9 g, 5.09 mmol) in DCM (18.0 mL, 20 V), trifluoroacetamide (1.15 g, 10.19 mmol), MgO (0.8 g, 20.38 mmol), $Rh_2(OAc)_4$ (0.12 g, 0.25 mmol) and $PhI(OAc)_2$ (2.46 g, 7.64 mmol) were added and the reaction mixture was stirred at RT overnight. Completion of the reaction was monitored by TLC, the reaction mixture was then filtered through celite and the filtrate was concentrated under vacuum. The resulting crude material was purified by flash chromatography (Biotage Isolera, eluent: 16-18% EtOAc in pet ether) to afford the title compound. Yield: 74% (1.1 g, white solid). LCMS: (Method A) 288.0 (M+H), Rt. 3.8 min, 71.1% (Max).

Intermediate 11 and Intermediate 12: N-((2-chloropyrimidin-5-yl)-(R)-(methyl)(oxo)-λ⁶-sulfanylidene)-2,2,2-trifluoroacetamide and N-((2-chloropyrimidin-5-yl)-(S)-(methyl)(oxo)-λ⁶-sulfanylidene)-2,2,2-trifluoroacetamide

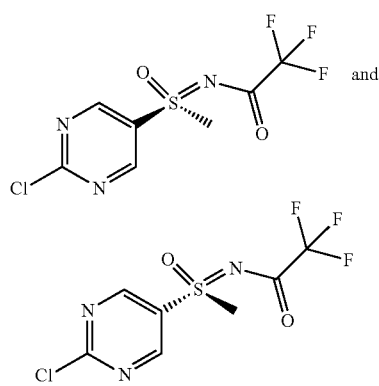

Step 1: 2-chloro-5-(methylsulfinyl)pyrimidine

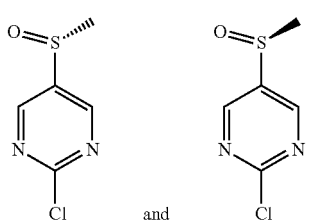

The intermediate 9 (502 g, 2.84 mol) was separated by SFC analysis (Pic SFC 10-150; $CO_2$: IPA (70:30); column: Lux A1 (250×30); flow rate: 100 mL/min; wave length: 210 nm; cycle time: 5 min; back pressure: 100 bar, Method E). The first eluting peak (250.0 L of IPA) was concentrated at 40° C. Yield: 40% (201.0 g, white solid). ¹H NMR (400 MHz, DMSO-$d_6$): δ 9.05 (s, 2H), 2.98 (s, 3H). LCMS: (Method A) 177.0 (M+H), Rt. 0.7 min, 99.9% (Max). HPLC: (Method B) Rt. 2.04 min, 99.8% (Max). Chiral SFC: (Method E) Rt 2.1 min, 100% (Max).

The second eluting peak (250.0 L of IPA) was concentrated at 40° C. Yield: 36% (180.0 g, white solid). ¹H NMR (400 MHz, DMSO-$d_6$): δ 9.04 (s, 2H), 2.98 (s, 3H). LCMS: (Method A) 177.0 (M+H), Rt. 0.8 min, 99.8% (Max). HPLC: (Method A) Rt. 1.02 min, 98.8% (Max). Chiral SFC: (Method E) Rt 4.6 min, 99.7%.

Step 2: N-((2-chloropyrimidin-5-yl)-(S)-(methyl)(oxo)-λ⁶-sulfanylidene)-2,2,2-trifluoroacetamide and N-((2-chloropyrimidin-5-yl)-(R)-(methyl)(oxo)-λ⁶-sulfanylidene)-2,2,2-trifluoroacetamide To the stirred solution of the first eluting compound isolated in step 1 (0.5 g, 2.8 mmol) in DCM (5 mL), trifluoroacetamide (0.64 g, 5.66 mmol), MgO (0.45 g, 11.3 mmol), $Rh_2(OAc)_4$ (0.062 g, 0.14 mmol) and $PhI(OAc)_2$ (1.36 g, 4.20 mmol) were added and the reaction mixture was stirred at RT overnight. Completion of the reaction was monitored by TLC. The reaction mixture was then filtered through celite, washed with DCM. The organic layer was concentrated under vacuum and the resulting crude material was purified by flash chromatography (Biotage Isolera, eluent: 25-28% EtOAc in pet ether) to afford Intermediate 11. Yield: 86% (0.69 g, white solid). ¹H NMR (400 MHz, DMSO-$d_6$): δ 9.39 (s, 2H), 3.98 (s, 3H). LCMS: (Method A) 191.9 (M-$COCF_3$+H), Rt. 3.8 min, 73.8%.

To a stirred solution of the second eluting compound isolated in step 1 (2.0 g, 0.01 mmol) in DCM (20 mL, 10 V), trifluoroacetamide (2.56 g, 0.226 mol), MgO (1.825 g, 0.045 mol), $Rh_2(OAC)_4$ (250 mg, 0.56 mol) and $PhI(OAC)_2$ (5.49 g, 0.016 mol) were added and stirred overnight at RT. Completion of the reaction was monitored by TLC, then the reaction mixture was filtered through celite. The filtrate was concentrated under vacuum, the resuting crude material was purified by flash chromatography (Biotage Isolera, eluent: 15-25% EtOAc in pet ether) to afford Intermediate 12. Yield: 62% (2.0 g, white solid). ¹H NMR (400 MHz, DMSO-$d_6$): δ 9.39 (s, 2H), 4.04 (s, 3H). LCMS: (Method A) 288.0 (M+H), Rt. 1.9 min, 92.8% (Max). HPLC: (Method A) Rt. 3.8 min, 96.1% (Max).

Intermediate 13: N-((2-chloropyrimidin-5-yl)(ethyl)(oxo)-λ⁶-sulfanylidene)-2,2,2-trifluoroacetamide

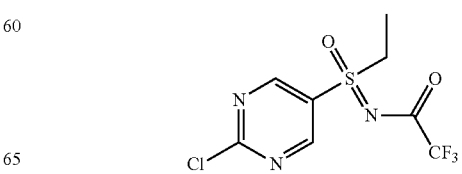

Step 1: 2-chloro-5-(ethylthio)pyrimidine

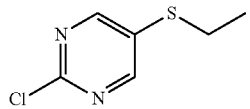

To a stirred solution of t-butyl nitrite (5.99 g, 58.13 mmol) and 1,2-diethyldisulfane (9.4 g, 77.51 mmol) in DCM (200 mL), 2-chloropyrimidin-5-amine (5 g, 38.75 mmol) was added portion wise at RT for 30 min and reaction mixture was stirred at RT overnight. After completion of the reaction (monitored by TLC), the reaction mixture was concentrated to obtain the crude material which was purified by flash chromatography (silica gel: 60-120 mesh, eluent: 5% EtOAc in pet ether) to afford the title compound. Yield: 24% (1.6 g, white solid). $^1$H NMR (400 MHz, DMSO-$d_6$): δ 8.74 (s, 2H), 3.12-3.08 (m, 2H), 1.26-1.22 (m, 3H).

Step 2: 2-chloro-5-(ethylsulfinyl)pyrimidine

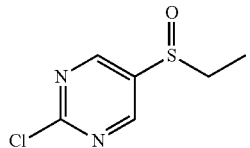

To a stirred solution of 2-chloro-5-(ethylthio)pyrimidine (1.6 g, 9.16 mmol) in DCM (32.0 mL, 20 V) cooled to 0° C., m-CPBA (2.05 g, 11.90 mmol) was added portion wise and the resulting mixture was stirred at 0° C. for 30 min. Completion of the reaction was monitored by TLC, the reaction mixture was then quenched with 10% NaHCO$_3$ solution and extracted with DCM (2×100 mL). The combined organic layer was washed with brine (30 mL), dried over anhydrous Na$_2$SO$_4$ and concentrated under vacuum. The resulting crude material was purified by flash chromatography (Biotage Isolera, eluent: 10-12% EtOAc in pet ether) to afford the title compound. Yield: 58% (1.0 g, off white solid). $^1$H NMR (400 MHz, DMSO-$d_6$): δ 8.99 (s, 2H), 3.31 (q, J=8.6 Hz, 2H), 1.11 (t, J=8.6 Hz, 3H). LCMS: (Method A) 191.2 (M+H), Rt. 1.3 min, 98.7% (Max).

Step 3: N-((2-chloropyrimidin-5-yl)(ethyl)(oxo)-λ$^6$-sulfanylidene)-2, 2,2-trifluoroacetamide

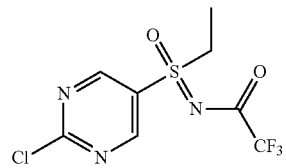 [SMILES: CCS(=O)(=NC(=O)C(F)(F)F)c1cnc(Cl)nc1]

To a stirred solution of 2-chloro-5-(ethylsulfinyl)pyrimidine (0.95 g, 5.00 mmol) in DCM (18.0 mL, 20 V), trifluoroacetamide (1.13 g, 10.0 mmol), MgO (0.8 g, 20.0 mmol), Rh$_2$(OAc)$_4$ (0.11 g, 0.25 mmol) and PhI(OAc)$_2$ (2.41 g, 7.5 mmol) were added and the reaction mixture was stirred at RT overnight. Completion of the reaction was monitored by TLC, the reaction mixture was then filtered through celite and the filtrate was concentrated under vacuum. The resulting crude material was purified by flash chromatography (Biotage Isolera, eluent: 16-18% EtOAc in pet ether) to afford the title compound. Yield: 63% (1.1 g, white solid).

Intermediate 14: N-((2-chloropyrimidin-5-yl)(oxo)(propyl)-λ$^6$-sulfanylidene)-2,2,2-trifluoroacetamide

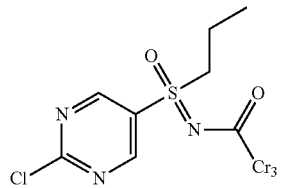

Step-1: 2-chloro-5-(propylthio)pyrimidine

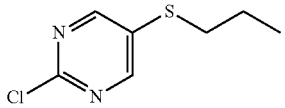

To a stirred solution of t-butyl nitrite (6.9 ml, 57.91 mmol) and 1,2-dipropyl disulfane (12 mL, 77.2 mmol) in DCE (200 mL), 2-chloropyrimidin-5-amine (5.0 g, 38.61 mmol, Angene) was added portion wise at RT for 30 min and the reaction mixture was stirred at RT overnight. Completion of reaction was monitored by TLC, then the reaction mixture was concentrated under reduced pressure. The resulting crude material was purified by flash chromatography (Biotage Isolera, eluent: 20% EtOAc in Pet-Ether) to afford the title compound. Yield: 25% (2.0 g, pale yellow solid). $^1$H NMR (400 MHz, DMSO-$d_6$): δ 8.72 (s, 2H), 2.68 (t, J=9.2 Hz, 2H), 1.81-1.54 (m, 2H), 1.14-0.90 (m, 3H). LCMS: (Method A) 189 (M+H), Rt. 3.7 min, 94.5 (Max).

Step-2: 2-chloro-5-(propylsulfinyl)pyrimidine

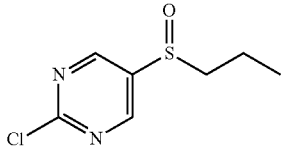

To a stirred solution of 2-chloro-5-(propylthio)pyrimidine (2.3 g, 12.7 mmol) in DCM (23 mL, 10 V), m-CPBA (Spectrochem, 1.89 g, 10.97 mmol) was added portion wise at 0° C. and stirred for 60 min at 0° C. Completion of the reaction was monitored by TLC, then the reaction mixture was quenched with 10% NaHCO$_3$ solution and extracted with DCM (2×50 mL). The combined DCM layer was washed with brine (20 mL), dried over anhydrous Na$_2$SO$_4$ and concentrated under vacuum. The resulting crude material was purified by flash chromatography (Biotage Isolera, eluent: 60-70% EtOAc in pet ether) to afford the title compound. Yield: 43% (0.9 g, pale yellow solid). ¹H NMR (400 MHz, DMSO-d₆): δ 9.01 (s, 2H), 3.19-3.00 (m, 2H), 1.75-1.53 (m, 2H), 0.97 (t, J=6.0 Hz, 3H).

Step-3: N-((2-chloropyrimidin-5-yl)(oxo)(propyl)-λ⁶-sulfanylidene)-2, 2,2-trifluoroacetamide

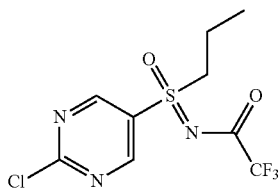 [SMILES: CCCS(=O)(=NC(=O)C(F)(F)F)c1cnc(Cl)nc1]

To a stirred solution of 2-chloro-5-(propylsulfinyl)pyrimidine (0.9 g, 4.07 mmol) in DCM (20 mL, 10 V), trifluoroacetamide (0.92 g, 8.10 mmol), MgO (1.56 g, 16.30 mmol), Rh₂(OAc)₄ (90.11 mg, 0.20 mmol) and PhI(OAc)₂ (1.97 g, 6.11 mmol) were added at RT and the reaction mixture was stirred at RT overnight. Completion of the reaction was monitored by TLC, then the reaction mixture was filtered through celite and concentrated under vacuum. The resulting crude material was purified by flash chromatography (Biotage Isolera, eluent: 16-18% EtOAc in pet ether) to afford the title compound. Yield: 78% (1.0 g, off white solid). ¹H NMR (400 MHz, DMSO-d₆): δ 9.36 (s, 2H), 3.19-3.00 (m, 2H), 1.75-1.53 (m, 2H), 0.97 (t, J=6.0 Hz, 3H).

Intermediate 15: N-((6-chloropyridin-3-yl)(methyl)(oxo)-λ⁶-sulfanylidene)-2,2,2-trifluoroacetamide

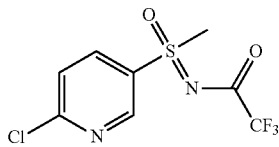 [SMILES: CS(=O)(=NC(=O)C(F)(F)F)c1ccc(Cl)nc1]

Step 1: 2-chloro-5-(methylthio)pyridine

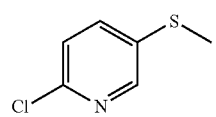

To a stirred solution of t-butyl nitrite (6.01 g, 58.33 mmol) and dimethyl disulfane (7.32 mL, 77.78 mmol) in DCE (50 mL), 6-chloropyridin-3-amine (5.0 g, 38.89 mmol) was added portion wise at RT for 30 min and stirred at RT overnight. Completion of the reaction was monitored by TLC, then the reaction mixture was poured into water and the aqueous layer was extracted with EtOAc (2×50 mL). The combined organic layer was dried over anhydrous Na₂SO₄ and concentrated under vacuum. The resulting crude material was purified by flash chromatography (Biotage Isolera, eluent: 50% EtOAc in pet-ether) to afford title compound. Yield: 73% (4.5 g, colourless liquid). ¹H NMR (400 MHz, DMSO-d₆): δ 8.30 (d, J=2.8 Hz, 1H), 7.79-7.76 (m, 1H), 7.46-7.44 (m, 1H), 2.54 (s, 3H). LCMS: (Method A) 160.2 (M+H), Rt. 2.3 min, 95.4% (Max).

Step 2: 2-chloro-5-(methylsulfinyl)pyridine

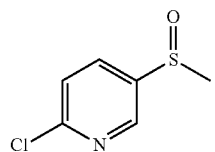

To a stirred solution of 2-chloro-5-(methylthio)pyridine (4.5 g, 28.19 mmol) in DCM (45 mL, 10 V) cooled to 0° C., m-CPBA (6.32 g, 36.64 mmol) was added portion wise and stirred at 0° C. for 60 min. Completion of the reaction was monitored by TLC, then the reaction mixture was quenched with 10% NaHCO₃ solution and extracted with DCM (2×100 mL). The combined organic layer was washed with brine (30 mL), dried over anhydrous Na₂SO₄ and concentrated under vacuum. The resulting crude material was purified by flash chromatography (Biotage Isolera, eluent: 60-70% EtOAc in pet ether) to afford the title compound. Yield: 72% (3.5 g, pale yellow solid). ¹H NMR (400 MHz, DMSO-d₆): δ 8.69 (d, J=3.2 Hz, 1H), 8.20-8.16 (m, 1H), 7.76 (s, 1H), 2.89 (s, 3H). LCMS: (Method A) 176.2 (M+H), Rt. 1.4 min, 96.3% (Max).

Step 3: N-((6-chloropyridin-3-yl)(methyl)(oxo)-λ⁶-sulfanylidene)-2,2,2-trifluoroacetamide

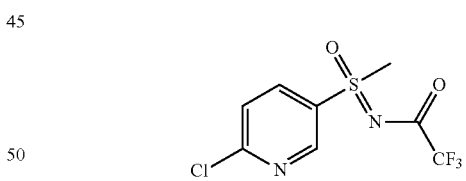

To a stirred solution of 2-chloro-5-(methylsulfinyl)pyridine (2.0 g, 11.42 mmol) in DCM (20 mL, 10 V), trifluoroacetamide (2.58 g, 22.85 mmol), MgO (1.84 g, 45.68 mmol), Rh₂(OAc)₄ (252 mg, 0.57 mmol) and PhI(OAC)₂ (5.52 g, 17.13 mmol) were added and the reaction mixture was stirred at RT overnight. After completion of the reaction (monitored by TLC), the reaction mixture was filtered through celite and the filtrate was concentrated under vacuum. The resulting crude material was purified by flash chromatography (Biotage Isolera, eluent: 16-18% EtOAc in pet ether) to afford the title compound. Yield: 86% (2.8 g, off white solid). ¹H NMR (400 MHz, DMSO-d₆): δ 9.03 (s, 1H), 8.48-8.46 (m, 1H), 7.96-7.93 (m, 1H), 3.91 (s, 3H). LCMS: (Method B) 190.9 (M-CF₃CO), Rt. 2.6 min, 96.4% (Max).

Intermediate 18: 1-(4-(methylthio)phenyl)piperazine hydrochloride

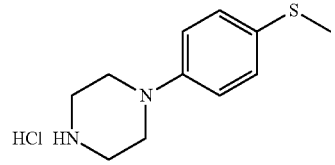

Step 1: tert-butyl 4-(4-(methylthio)phenyl)piperazine-1-carboxylate

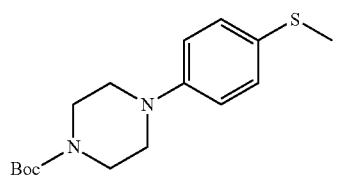 [SMILES: CSc1ccc(N2CCN(C(=O)OC(C)(C)C)CC2)cc1]

To a degassed stirred solution of (4-bromophenyl)(methyl)sulfane (5.0 g, 24.6 mmol), 1-Boc piperazine (4.6 g, 24.6 mmol), Davephos (2.63 g, 6.66 mmol, Combi-blocks) and KO$^t$Bu (4.7 g, 49.0 mmol) in 1,4 dioxane (10 mL), Pd(dba)$_3$ (0.45 g, 0.4 mmol) was added at RT. The reaction mixture was heated under microwave irradiation at 120° C. for 15 min. Completion of the reaction was monitored by TLC, the reaction mixture was then evaporated at 50° C. under reduced pressure. To the resulting crude mixture, water (10 mL) was added and the aqueous layer was extracted with EtOAc (2×50 mL). The combined organic layer was dried over anhydrous Na$_2$SO$_4$ and concentrated under vacuum. The resulting crude material was purified by flash chromatography (Biotage Isolera, eluent: 50% EtOAc in pet-ether) to afford the tittle compound. Yield: 88% (6.0 g, off white solid). $^1$H NMR (400 MHz, DMSO-d$_6$): δ 7.25-7.23 (m, 2H), 6.96-6.93 (m, 2H), 3.58-3.57 (m, 4H), 3.12-3.09 (m, 4H), 2.42 (s, 3H), 1.50 (s, 9H). LCMS: (Method A) 309.2 (M+H), Rt. 4.3 min, 98.7% (Max).

Step-2: 1-(4-(methylthio)phenyl)piperazine hydrochloride

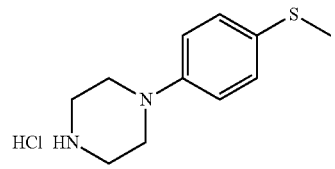

To a stirred solution of tert-butyl 4-(4-(methylthio)phenyl)piperazine-1-carboxylate (6.0 g, 19.41 mmol) in 1,4 dioxane (20 mL), HCl solution in dioxane (4M, 20 mL) was added at 0° C. and the reaction mixture was stirred for 4 h at RT. Completion of the reaction was monitored by TLC, then the reaction mixture was evaporated under reduced pressure to afford the tittle compound. Yield: 89% (4.8 g, off white solid). $^1$H NMR (400 MHz, DMSO-d$_6$): δ 7.5 (m, 2H), 7.22-7.16 (m, 2H), 7.06-6.93 (m, 2H), 3.02-2.99 (m, 4H), 2.51-2.38 (m, 4H), 2.38 (s, 3H).

Example 22: (2-(4-(1-(benzo[d]thiazol-5-yl)ethyl)piperazin-1-yl)pyrimidin-5-yl)(imino)(methyl)-λ$^6$-sulfanone

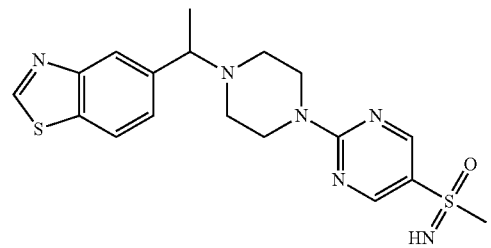 [SMILES: CC(c1ccc2scnc2c1)N1CCN(c2ncc(S(C)(=N)=O)cn2)CC1]

To a stirred solution of Intermediate 6 (0.12 g, 0.51 mmol) in DMF (1.2 mL, 10 V), TEA (0.23 mL, 1.68 mmol) and intermediate 10 (0.16 g, 5.60 mmol) were added and the reaction mixture was stirred at RT overnight. Completion of the reaction was monitored by TLC, then the reaction mixture was concentrated under vacuum. The resulting crude material was purified by flash chromatography (Biotage Isolera, eluent: 40% EtOAc in pet ether) to obtain the pure intermediate N-((2-(4-(1-(benzo[d]thiazol-5-yl)ethyl)piperazin-1-yl)pyrimidin-5-yl)(methyl)(oxo)-λ$^6$-sulfanylidene)-2,2,2-trifluoroacetamide. Yield: 87% (0.21 g, off-white solid).

To this intermediate, methanol (2.2 mL, 20 V) and K$_2$CO$_3$ (0.21 g, 1.68 mmol) were added and the resulting mixture was stirred for 20 min. After 20 min, the reaction mixture was filtered through celite and concentrated under vacuum. To the resulting mixture, water (50 mL) was added and the aqueous layer was extracted with DCM (2×100 mL). The combined organic layer was dried over anhydrous Na$_2$SO$_4$ and concentrated under vacuum. The resulting crude material was purified by flash chromatography (Biotage Isolera, gradient: 1-2% methanol in EtOAc) to afford the title compound. Yield: 15% (30 mg, white solid). $^1$H NMR (400 MHz, DMSO-d$_6$): δ 9.38 (s, 1H), 8.65 (s, 2H), 8.11 (d, J=8.4 Hz, 1H), 8.02 (d, J=1.2 Hz, 1H), 7.50 (dd, J=8.2, 1.2 Hz, 1H), 4.22 (s, 1H), 3.85-3.83 (m, 4H), 3.68 (d, J=6.4 Hz, 1H), 3.06 (d, J=0.8 Hz, 3H), 2.52-2.32 (m, 4H), 1.41 (d, J=6.8 Hz, 3H). LCMS: (Method A) 403.3 (M+H), Rt. 1.8 min, 97.5% (Max). HPLC: (Method A) Rt. 1.9 min, 95.9% (Max).

Example 23: (2-(4-(1-(benzo[d]thiazol-5-yl)ethyl)piperazin-1-yl)pyrimidin-5-yl)(ethyl)(imino)-λ$^6$-sulfanone

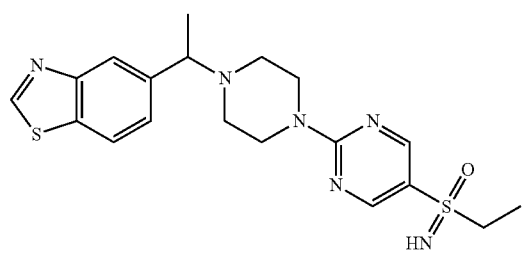 [SMILES: CCS(=N)(=O)c1cnc(N2CCN(C(C)c3ccc4scnc4c3)CC2)nc1]

To a stirred solution of intermediate 6 (0.25 g, 1.01 mmol) in DMF (2.50 mL, 10 V), TEA (0.4 mL, 3.03 mmol) and intermediate 13 (0.30 g, 1.01 mmol) were added and the reaction mixture was stirred at RT overnight. Completion of the reaction was monitored by TLC, then the reaction mixture was concentrated under vacuum. The resulting crude material was purified by flash chromatography (Biotage Isolera, eluent: 40% EtOAc in pet ether) to obtain the pure intermediate N-((2-(4-(1-(benzo[d]thiazol-5-yl)ethyl)piperazin-1-yl)pyrimidin-5-yl)(ethyl)(oxo)-$\lambda^6$-sulfanylidene)-2,2,2-trifluoroacetamide. Yield: 88% (0.45 g, off-white solid).

To this intermediate, methanol (2.5 mL, 20 V) and $K_2CO_3$ (0.40 g, 3.23 mmol) were added and the resulting mixture was stirred for 20 min. After 20 min, the reaction mixture was filtered through celite and concentrated under vacuum. To the resulting mixture, water (50 mL) was added and the aqueous layer was extracted with DCM (2×100 mL). The combined organic layer was dried over anhydrous $Na_2SO_4$ and concentrated under vacuum. The resulting crude material was purified by flash chromatography (Biotage Isolera, gradient: 1-2% methanol in EtOAc) to afford the title compound. Yield: 18% (60 mg, white solid). $^1$H NMR (400 MHz, DMSO-$d_6$): δ 9.38 (s, 1H), 8.58 (s, 2H), 8.12 (d, J=8.4 Hz, 1H), 8.02 (s, 1H), 7.51-7.49 (m, 1H), 4.22 (s, 1H), 3.85-3.83 (m, 4H), 3.67 (d, J=6.8 Hz, 1H), 3.12 (t, J=7.6 Hz, 2H), 2.49-2.39 (m, 4H), 1.40 (d, J=6.40 Hz, 3H), 1.07 (t, J=7.20 Hz, 3H). LCMS: (Method A) 417.3 (M+H), Rt. 2.2 min, 99.6% (Max). HPLC: (Method A) Rt. 2.0 min, 97.1% (Max).

Example 24: (2-(4-(1-(benzo[d]thiazol-5-yl)ethyl)piperazin-1-yl)pyrimidin-5-yl)(imino)(propyl)-$\lambda^6$-sulfanone

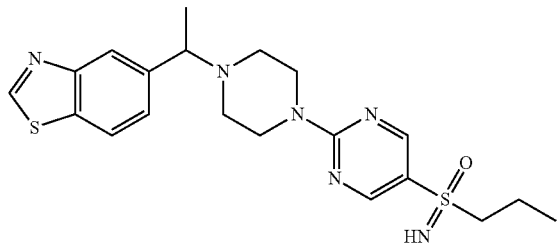 [SMILES: CCCS(=N)(=O)c1cnc(N2CCN(C(C)c3ccc4scnc4c3)CC2)nc1]

To a stirred solution of intermediate 6 (235 mg, 9.50 mmol) in DMF (2.5 mL, 10 V), TEA (0.5 mL, 3.8 mmol) and intermediate 14 (235 mg, 0.95 mmol) were added at RT and the reaction mixture was stirred overnight at RT. Completion of the reaction was monitored by TLC, then the reaction mixture was evaporated at 50° C. under vacuum. To the resulting mixture, water (2 mL) was added and the aqueous layer was extracted with EtOAc (2×50 mL). The combined organic layer was dried over anhydrous $Na_2SO_4$ and concentrated under vacuum. The resulting crude material was purified by flash chromatography (silica gel: 230-400 mesh, eluent: 50% EtOAc in pet-ether) to obtain the pure intermediate N-((2-(4-(1-(benzo[d]thiazol-5-yl)ethyl)piperazin-1-yl)pyrimidin-5-yl)(oxo)(propyl)-$\lambda^6$-sulfanylidene)-2,2,2-trifluoroacetamide. Yield: 28% (140 mg, off white solid).

To this intermediate methanol (7 mL, 20 V) and $K_2CO_3$ (414 mg, 4.53 mmol) were added and stirred at RT for 20 min. After 20 min, the reaction mixture was filtered through celite and concentrated under vacuum. To the resulting mixture, water (20 mL) was added and the aqueous layer was extracted with DCM (2×100 mL). The combined organic layer was dried over anhydrous $Na_2SO_4$ and concentrated under vacuum. The resulting crude material was purified by flash chromatography (Biotage Isolera, gradient: 1-2% methanol in DCM) to afford the title compound. Yield: 21% (35 mg, off white solid). $^1$H NMR (400 MHz, DMSO-$d_6$): δ 9.39 (s, 1H), 8.59 (s, 2H), 8.13 (d, J=8.0 Hz, 1H), 8.03 (s, 1H), 7.51 (d, J=8.4 Hz, 1H), 4.22 (s, 1H), 3.85-3.83 (m, 4H), 3.68 (d, J=6.0 Hz, 1H), 3.17-3.08 (m, 2H), 2.53-2.44 (m, 4H), 1.57-1.51 (m, 2H), 1.41 (d, J=6.40 Hz, 3H), 0.88 (t, J=7.20 Hz, 3H). LCMS: (Method A) 431.3 (M+H), Rt. 2.4 min, 97.2% (Max). HPLC: (Method A) Rt. 2.2 min, 97.6% (Max).

Example 25: (2-(4-(1-(benzo[d]thiazol-5-yl)ethyl)piperazin-1-yl)pyrimidin-5-yl)(methyl)(methylimino)-$\lambda^6$-sulfanone

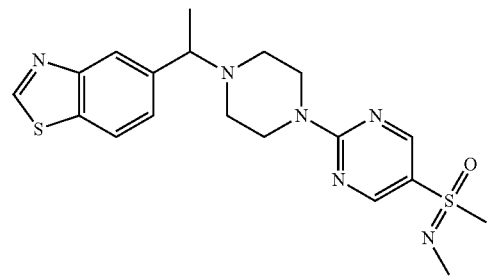 [SMILES: CN=S(C)(=O)c1cnc(N2CCN(C(C)c3ccc4scnc4c3)CC2)nc1]

To a stirred solution of example 22 (0.1 g, 0.25 mmol) in THF (1.0 mL, 10V), NaH (60%) (18 mg, 0.37 mmol) was added at 0° C. and stirred for 15 min. Then MeI (0.04 mL, 0.62 mmol) was added to the reaction mixture in a sealed tube and heated overnight at 90° C. Completion of the reaction was monitored by TLC, then the reaction mixture was concentrated under vacuum. The resulting crude material was purified by flash chromatography (Biotage Isolera, gradient: 5-6% MeOH in DCM) and further purified by Prep. HPLC (Method B) to afford the title compound. Yield: 23% (23 mg, off white solid). $^1$H NMR (400 MHz, DMSO-$d_6$): δ 9.38 (s, 1H), 8.55 (s, 2H), 8.11 (d, J=8.4 Hz, 1H), 8.02 (d, J=1.2 Hz, 1H), 7.50 (dd, J=8.2, 1.2 Hz, 1H), 3.86-3.70 (m, 4H), 3.69-3.65 (m, 1H), 3.10 (s, 3H), 2.56-2.51 (m, 2H), 2.50-2.32 (m, 5H), 1.41 (d, J=6.8 Hz, 3H). LCMS: (Method A) 416.8 (M+H), Rt. 1.94 min, 98.9% (Max). HPLC: (Method A) Rt. 1.9 min, 99.7% (Max).

Example 26: (6-(4-(1-(benzo[d]thiazol-5-yl)ethyl)piperazin-1-yl)pyridin-3-yl)(imino)(methyl)-$\lambda^6$-sulfanone

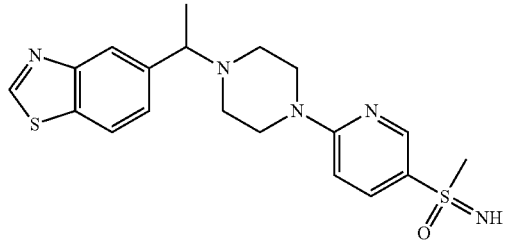 [SMILES: CC(c1ccc2scnc2c1)N1CCN(c2ccc(S(C)(=N)=O)cn2)CC1]

To a stirred solution of intermediate 6 (350 mg, 1.41 mmol) in DMF (3.5 mL), TEA (0.6 mL, 4.25 mmol) and intermediate 15 (446 mg, 1.56 mmol) were added at RT and the reaction mixture was stirred overnight. Completion of the reaction was monitored by TLC, then the reaction mixture was evaporated at 50° C. under vacuum. To the resulting mixture, water (10 mL) was added and the aqueous layer was extracted with EtOAc (2×50 mL). The combined organic layer was dried over anhydrous $Na_2SO_4$ and concentrated under vacuum. The resulting crude material was purified by flash chromatography (silica gel: 230-400 mesh, eluent: 50% EtOAc in pet-ether) to obtain the pure intermediate N-((6-(4-(1-(benzo[d]thiazol-5-yl)ethyl)piperazin-1-yl)pyridin-3-yl)(methyl)(oxo)-$\lambda^6$-sulfanylidene)-2,2,2-trifluoroacetamide. Yield: 41% (252 mg, off white solid).

To this intermediate, methanol (7 mL, 20 V) and $K_2CO_3$ (414 mg, 4.53 mmol) were added and the resulting mixture was stirred at RT for 20 min. After 20 min, the reaction mixture was filtered through celite and concentrated under vacuum. To the resulting mixture, water (50 mL) was added and the aqueous layer was extracted with DCM (2×100 mL). The combined organic layer was dried over anhydrous $Na_2SO_4$ and concentrated under vacuum. The resulting crude material was purified by flash chromatography (Biotage Isolera, gradient: 1-2% methanol in DCM) to afford the title compound. Yield: 30% (168.89 mg, off white solid). $^1$H NMR (400 MHz, DMSO-$d_6$): δ 9.38 (s, 1H), 8.48 (d, J=2.4 Hz, 1H), 8.12 (d, J=8.4 Hz, 1H), 8.02 (d, J=1.2 Hz, 1H), 7.85 (dd, J=9.2, 2.4 Hz, 1H), 7.49 (dd, J=6.8, 1.6 Hz, 1H), 6.87 (d, J=9.2 Hz, 1H), 4.02 (s, 1H), 3.67-3.62 (m, 5H), 3.00 (s, 3H), 2.67-2.33 (m, 4H), 1.41 (d, J=6.40 Hz, 3H). LCMS: (Method A) 402.0 (M+H), Rt. 1.8 min, 97.7% (Max). HPLC: (Method A) Rt. 1.8 min, 97.6% (Max).

Example 27: (2-(4-(1-(benzo[d]thiazol-5-yl)ethyl)piperazin-1-yl)pyrimidin-5-yl)(ethylimino)(methyl)-$\lambda^6$-sulfanone

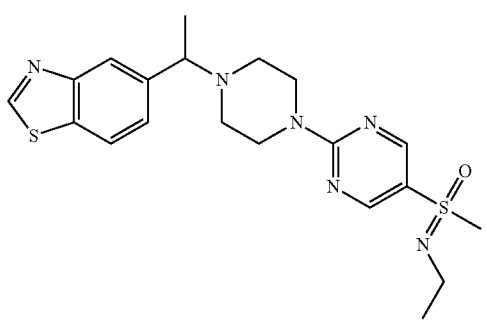 [SMILES: CCN=S(C)(=O)c1cnc(N2CCN(C(C)c3ccc4scnc4c3)CC2)nc1]

To a stirred solution of example 22 (0.12 g, 0.51 mmol) in DMF (1.2 mL, 10 V), NaH (60%) (0.23 mg, 1.68 mmol) was added at 0° C. and stirred for 15 min. Then ethyl bromide (0.16 g, 5.6 mmol) was added to the reaction mixture and it was stirred overnight at RT. Completion of the reaction was monitored by TLC, then the reaction mixture was concentrated under vacuum. The resulting crude material was purified by prep HPLC (Method B). Yield: 15% (30 mg, white solid). $^1$H NMR (400 MHz, DMSO-$d_6$): δ 9.38 (s, 1H), 8.65 (s, 2H), 8.11 (d, J=8.4 Hz, 1H), 8.02 (d, J=1.2 Hz, 1H), 7.50 (dd, J=8.2, 1.2 Hz, 1H), 3.85-3.83 (m, 4H), 3.68 (q, J=6.4 Hz, 1H), 3.33-3.30 (m, 2H), 3.06 (s, 3H), 2.44-2.33 (m, 4H), 1.41 (d, J=6.80 Hz, 3H) 1.08 (t, J=6.4 Hz, 3H). LCMS: (Method A) 431.3 (M+H), Rt. 2.1 min, 99.7% (Max). HPLC: (Method A) Rt. 1.9 min, 95.9% (Max).

Example 28: (2-(4-(1-(benzo[d]thiazol-5-yl)ethyl)piperazin-1-yl)pyrimidin-5-yl)(isopropylimino)(methyl)-$\lambda^6$-sulfanone

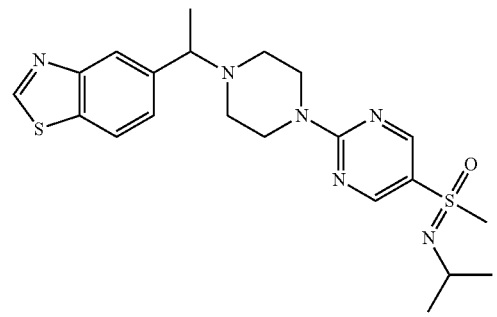 [SMILES: CC(C)N=S(C)(=O)c1cnc(N2CCN(C(C)c3ccc4scnc4c3)CC2)nc1]

To a stirred solution of example 22 (0.15 g, 0.37 mmol) in DMF (3.0 mL, 10 V), NaH (60%) (17 mg, 0.746 mmol) was added at 0° C. and stirred for 15 min. Then iso-propyl bromide (91 mg, 0.74 mmol) was added to the reaction mixture and the reaction mixture was stirred overnight at RT. Completion of the reaction was monitored by TLC, then the reaction mixture was concentrated under vacuum. The crude was purified by prep HPLC (Condition Method B). Yield: 8% (12.5 mg, white solid). $^1$H NMR (400 MHz, DMSO-$d_6$): δ 9.39 (d, J=2.0 Hz, 1H), 8.58 (d, J=2.0 Hz, 2H), 8.12 (d, J=8.8 Hz, 1H), 8.03 (s, 1H), 7.50 (d, J=8.8 Hz, 1H), 4.11-4.10 (m, 4H), 3.85 (q, J=6.8 Hz, 1H), 3.18-3.09 (m, 4H), 2.52-2.33 (m, 4H), 1.42 (d, J=6.4 Hz, 3H), 1.02 (d, J=7.2 Hz, 6H). LCMS: (Method A) 445.0 (M+H), Rt. 2.2 min, 96.5% (Max). HPLC: (Method A) Rt. 2.3 min, 97.4% (Max).

Example 29: (2-(4-(1-(benzo[d]thiazol-5-yl)ethyl)piperazin-1-yl)pyrimidin-5-yl)((2-methoxyethyl)imino)(methyl)-$\lambda^6$-sulfanone

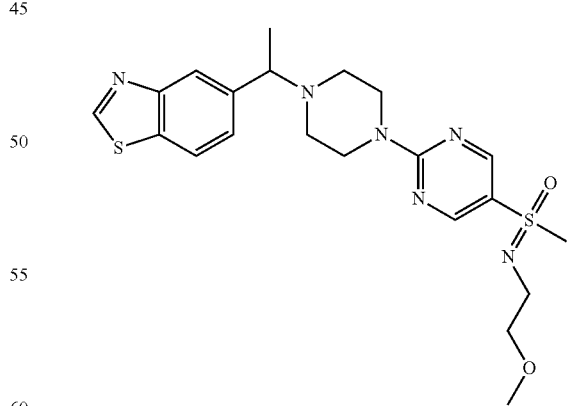

To a stirred solution of example 22 (0.15 g, 0.51 mmol) in DMF (3.0 mL, 10 V), NaH (60%) (0.13 mg, 0.55 mmol) was added at 0° C. and stirred for 15 min. Then methoxymethyl bromide (103 mg, 0.74 mmol) was added and the reaction mixture was stirred overnight at RT. Completion of the reaction was monitored by TLC, then the reaction mixture was concentrated under vacuum. The resulting crude was purified by prep HPLC (method B). Yield: 8% (14.3 mg, white solid). ¹H NMR (400 MHz, DMSO-$d_6$): δ 9.38 (s, 1H), 8.59 (s, 2H), 8.11 (d, J=8.4 Hz, 1H), 8.03 (s, 1H), 7.50 (dd, J=8.4, 1.2 Hz, 1H), 3.85-3.82 (m, 4H), 3.68 (d, J=6.4 Hz, 1H), 3.18 (s, 3H), 3.12 (s, 3H), 2.95-2.82 (m, 2H), 2.50-2.33 (m, 4H), 1.40 (d, J=6.4 Hz, 3H). LCMS: (Method A) 460.9 (M+H), Rt. 2.1 min, 99.1% (Max). HPLC: (Method A) Rt. 2.1 min, 99.1% (Max).

Example 30: (6-(4-(1-(benzo[d]thiazol-5-yl)ethyl)piperazin-1-yl)pyridin-3-yl)(methyl)(methylimino)-$\lambda^6$-sulfanone

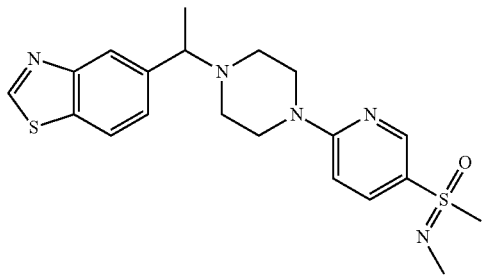

To the stirred solution of example 26 (0.11 g, 0.27 mmol) in THF (2 mL), NaH (60%) (0.03 g, 0.55 mmol) was added at 0° C. and stirred for 15 min. Then MeI (0.05 mL, 0.87 mmol) was added to the reaction mixture and stirred overnight at RT. After completion of the reaction (monitored by TLC), the resulting reaction mixture was quenched with ice cold water (2 mL) and the aqueous layer was extracted with EtOAc (2×15 mL). The combined organic layer was dried over anhydrous $Na_2SO_4$ and evaporated under vacuum. The resulting crude material was purified by Prep HPLC (Method B) to afford the tittle compound. Yield: 23% (27 mg, off white solid). ¹H NMR (400 MHz, DMSO-$d_6$): δ 9.39 (s, 1H), 8.37 (s, 1H), 8.13 (d, J=8.4 Hz, 1H), 8.03 (s, 1H), 7.75 (d, J=9.2 Hz, 1H), 7.51 (d, J=8.4 Hz, 1H), 6.91 (d, J=9.2 Hz, 1H), 3.64-3.57 (m, 5H), 3.05 (s, 3H), 2.44-2.41 (m, 7H), 1.42 (d, J=6.4 Hz, 3H). LCMS: (Method A) 415.8 (M+H), Rt. 1.9 min, 97.5% (Max). HPLC: (Method A) Rt. 2.1 min, 97.3% (Max).

Example 31: ((2-(4-(1-(benzo[d]thiazol-5-yl)ethyl)piperazin-1-yl)pyrimidin-5-yl)imino)dimethyl-$\lambda^6$-sulfanone

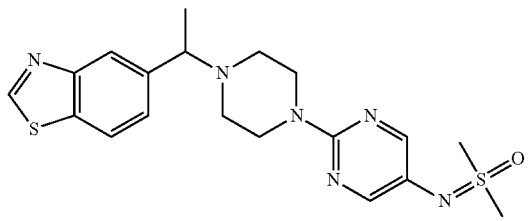 [SMILES: CC(c1ccc2scnc2c1)N1CCN(c2ncc(N=S(C)(C)=O)cn2)CC1]

Step 1: 5-(1-(4-(5-bromopyrimidin-2-yl)piperazin-1-yl)ethyl)benzo[d]thiazole

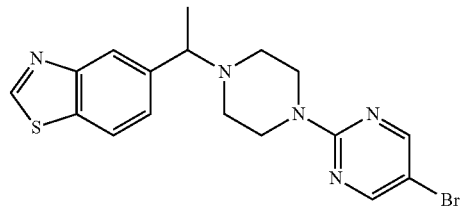 [SMILES: CC(c1ccc2scnc2c1)N1CCN(c2ncc(Br)cn2)CC1]

To a stirred solution of intermediate 6 (0.5 g, 2.02 mmol) in DMF (10 mL), TEA (0.84 mL, 6.06 mmol) and 5-bromo-2-chloropyrimidine (0.469 g, 2.42 mmol) were added at RT and stirred overnight at 90° C. After completion of the reaction (monitored by TLC), the reaction mixture was evaporated at 45° C. under vacuum and the resulting mixture was dissolved in DCM (10 mL). The organic layer was washed with water (5 mL), brine solution (5 mL), dried over anhydrous $Na_2SO_4$ and evaporated under vacuum. The resulting crude material was purified by flash column chromatography (Biotage Isolera, 60% EtOAC in pet-ether) to afford the title compound. Yield: 61% (500 mg, white solid). ¹H NMR (400 MHz, DMSO-$d_6$): δ 9.38 (s, 1H), 8.42 (s, 2H), 8.11 (d, J=8.4 Hz, 1H), 8.01 (s, 1H), 7.49 (d, J=8.0 Hz, 1H), 3.69-3.64 (m, 5H), 2.40-2.33 (m, 4H), 1.40 (d, J=6.4 Hz, 3H). LCMS: (Method A) 406.2 (M+H), Rt. 3.0 min, 99.9% (Max).

Step 2: ((2-(4-(1-(benzo[d]thiazol-5-yl)ethyl)piperazin-1-yl)pyrimidin-5-yl)imino)dimethyl-$\lambda^6$-sulfanone

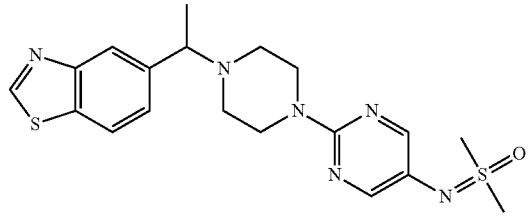 [SMILES: CC(c1ccc2scnc2c1)N1CCN(c2ncc(N=S(C)(C)=O)cn2)CC1]

To a stirred solution of 5-(1-(4-(5-bromopyrimidin-2-yl)piperazin-1-yl)ethyl)benzo[d]thiazole (300 mg, 0.74 mmol) in dry toluene (6 mL), Pd(OAc)$_2$ (6.6 mg, 0.03 mmol), Ru-phos (27.7 mg, 0.06 mmol), cesium carbonate (727 mg, 2.23 mmol) and S,S-Dimethyl sulphimide (83.2 mg, 0.9 mmol) were added and heated overnight at 110° C. Completion of the reaction was monitored by TLC, then the reaction mixture was concentrated under vacuum. The resulting crude material was purified by flash chromatography (Biotage Isolera, eluent: 8-10% methanol in $CHCl_3$) to afford the title compound. Yield: 4% (10.7 mg, brown solid). ¹H NMR (400 MHz, DMSO-$d_6$): δ 9.39 (d, J=8.0 Hz, 1H), 8.12 (d, J=8.0 Hz, 1H), 8.03-8.01 (m, 3H), 7.51-7.49 (m, 1H), 3.64-3.59 (m, 4H), 3.37-3.36 (m, 1H), 3.18 (s, 6H), 2.42-2.34 (m, 4H), 1.42 (d, J=8.0 Hz, 3H). LCMS: (Method A) 417.0 (M+H), Rt. 2.1 min, 98.5% (Max). HPLC: (Method A) Rt. 2.1 min, 98.8 (Max).

Example 33: (4-(4-(1-(benzo[d]thiazol-5-yl)ethyl)piperazin-1-yl)phenyl)(imino)(methyl)-λ⁶-sulfanone

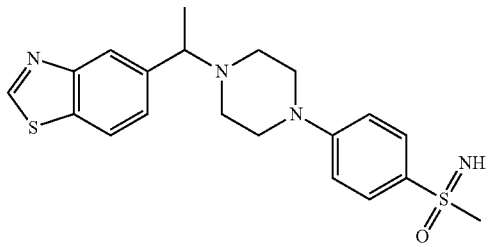 [SMILES: CC(c1ccc2scnc2c1)N1CCN(c2ccc(S(C)(=N)=O)cc2)CC1]

Step 1: 5-(1-(4-(4-(methylthio)phenyl)piperazin-1-yl)ethyl)benzo[d]thiazole

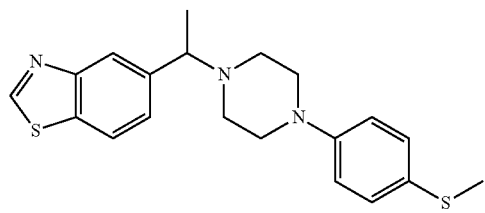 [SMILES: CSc1ccc(N2CCN(C(C)c3ccc4scnc4c3)CC2)cc1]

To a stirred solution of intermediate 18 (1.6 g, 6.56 mmol) and TEA (2.76 mL, 19.67 mmol) in DMF (10 mL), Intermediate 1 (1.29 g, 6.56 mmol) was added at RT and stirred at 70° C. overnight. Completion of the reaction was monitored by TLC, then the reaction mixture was evaporated at 50° C. under vacuum. To the resulting mixture, water (10 mL) was added and the aqueous layer was extracted with EtOAc (2×50 mL). The combined organic layer was dried over anhydrous Na₂SO₄ and concentrated under vacuum. The resulting crude material was purified by flash chromatography (Biotage Isolera, gradient: 1-2% MeOH in DCM) to afford the title compound. Yield: 25% (600 mg, off white solid). ¹H NMR (400 MHz, DMSO-d₆): δ 9.94 (s, 1H), 8.13 (d, J=8.4 Hz, 1H), 8.04 (s, 1H), 7.68 (d, J=8.8 Hz, 2H), 7.51 (d, J=8.4 Hz, 1H), 7.01 (d, J=9.2 Hz, 2H), 3.68-3.66 (m, 1H), 3.34-3.30 (m, 4H), 2.37 (s, 3H), 2.68-2.34 (m, 4H), 1.42 (d, J=6.8 Hz, 3H). LCMS: (Method A) 369.9 (M+H), Rt. 2.3 min, 83.3% (Max).

Step 2: 5-(1-(4-(4-(methylsulfinyl)phenyl)piperazin-1-yl)ethyl)benzo[d]thiazole

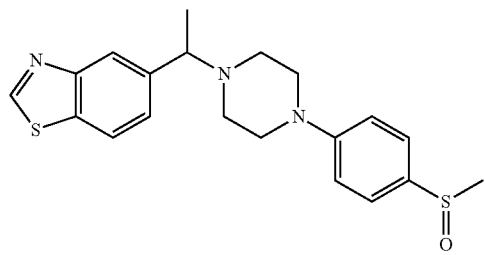 [SMILES: CC(c1ccc2scnc2c1)N1CCN(c2ccc(S(C)=O)cc2)CC1]

To a stirred solution of 5-(1-(4-(4-(methylthio)phenyl)piperazin-1-yl)ethyl)benzo[d]thiazole (700 mg, 1.90 mmol) in DCM (7 mL, 10 V) at 0° C., m-CPBA (722 mg, 2.09 mmol) was added portion wise and stirred for 1 h at 0° C. After completion of the reaction (monitored by TLC), the reaction mixture was quenched with 10% NaHCO₃ solution and the aqueous layer was extracted with DCM (2×100 mL). The combined organic layer was washed with brine (30 mL), dried over anhydrous Na₂SO₄ and concentrated under vacuum. The resulting crude material was purified by flash chromatography (Biotage Isolera, eluent: 60-70% EtOAc in pet ether) to afford the title compound. Yield: 34% (250 mg, pale yellow gummy solid). ¹H NMR (400 MHz, DMSO-d₆): δ 9.94 (s, 1H), 8.13 (d, J=8.4 Hz, 1H), 8.04 (s, 1H), 7.68 (d, J=8.8 Hz, 2H), 7.51 (d, J=8.4 Hz, 1H), 7.01 (d, J=9.2 Hz, 2H), 3.68-3.66 (m, 1H), 3.34-3.30 (m, 4H), 2.65 (s, 3H), 2.68-2.34 (m, 4H), 1.42 (d, J=6.80 Hz, 3H). LCMS: (Method A) 386.5 (M+H), Rt. 1.7 min, 83.3% (Max).

Step 3: (4-(4-(1-(benzo[d]thiazol-5-yl)ethyl)piperazin-1-yl)phenyl)(imino)(methyl)-λ⁶-sulfanone

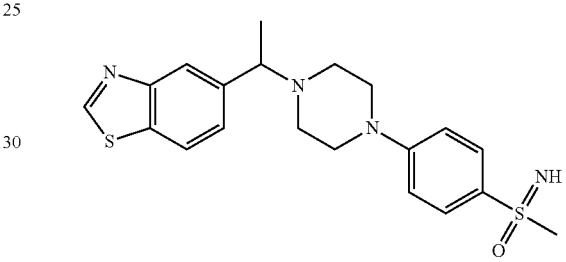

To a stirred solution of 5-(1-(4-(4-(methylsulfinyl)phenyl)piperazin-1-yl)ethyl)benzo[d]thiazole (250 mg, 0.65 mmol) in DCM (5 mL, 20 V), trifluoroacetamide (146 mg, 1.30 mmol), MgO (118 mg, 2.59 mmol), Rh₂(OAc)₄ (14.32 mg, 0.03 mmol) and PhI(OAc)₂ (166 mg, 0.97 mmol) were added and the reaction mixture was stirred overnight at RT. Completion of the reaction was monitored by TLC, then the reaction mixture was filtered through celite and concentrated under vacuum. The resulting crude material was purified by flash chromatography (Biotage Isolera, eluent: 55-60% EtOAc in pet ether) to obatin the pure intermediate N-((4-(4-(1-(benzo[d]thiazol-5-yl)ethyl)piperazin-1-yl)phenyl)(methyl)(oxo)-λ⁶-sulfanylidene)-2,2,2-trifluoroacetamide. Yield: 8% (25 mg, off white solid).

To this intermediate, methanol (10 mL, 20 V) and K₂CO₃ (89 mg, 0.648 mmol) were added and stirred for 20 min. After 20 min, the reaction mixture was filtered through celite and concentrated under vacuum. To the resulting mixture, water (50 mL) was added and the aqueous layer was extracted with DCM (2×100 mL). The combined organic layer was dried over anhydrous Na₂SO₄ and concentrated under vacuum. The resulting crude material was purified by flash chromatography (Biotage Isolera, gradient: 1-2% methanol in DCM) to afford the title compound. Yield: 6% (4.86 mg, off white solid). ¹H NMR (400 MHz, DMSO-d₆): δ 9.94 (s, 1H), 8.13 (d, J=8.4 Hz, 1H), 8.04 (s, 1H), 7.68 (d, J=8.8 Hz, 2H), 7.51 (d, J=8.4 Hz, 1H), 7.01 (d, J=9.2 Hz, 2H), 3.89 (s, 1H), 3.68-3.66 (m, 1H), 3.34-3.30 (m, 4H), 2.97 (s, 3H), 2.68-2.34 (m, 4H), 1.42 (d, J=6.80 Hz, 3H). LCMS: (Method A) 401.0 (M+H), Rt. 1.9 min, 98.2% (Max). HPLC: (Method A) Rt. 1.8 min, 96.9% (Max).

Example 34: (2-(4-((S)-1-(benzo[d]thiazol-5-yl)ethyl)piperazin-1-yl)pyrimidin-5-yl)(imino)(methyl)-λ⁶-sulfanone or (2-(4-((R)-1-(benzo[d]thiazol-5-yl)ethyl)piperazin-1-yl)pyrimidin-5-yl)(imino)(methyl)-λ⁶-sulfanone Example 35: (S)-(2-(4-((S)-1-(benzo[d]thiazol-5yl)ethyl)piperazin-1-yl)pyrimidin-5-yl)(imino)(methyl)-λ⁶-sulfanone or (R)-(2-(4-((S)-1-(benzo[d]thiazol-5-yl)ethyl)piperazin-1-yl)pyrimidin-5-yl)(imino)(methyl)-λ⁶-sulfanone or (S)-(2-(4-((R)-1-(benzo[d]thiazol-5-yl)ethyl)piperazin-1-yl)pyrimidin-5-yl)(imino)(methyl)-λ⁶-sulfanone or (R)-(2-(4-((R)-1-(benzo[d]thiazol-5-yl)ethyl)piperazin-1-yl)pyrimidin-5-yl)(imino)(methyl)-λ⁶-sulfanone

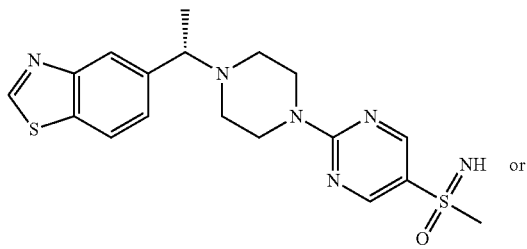

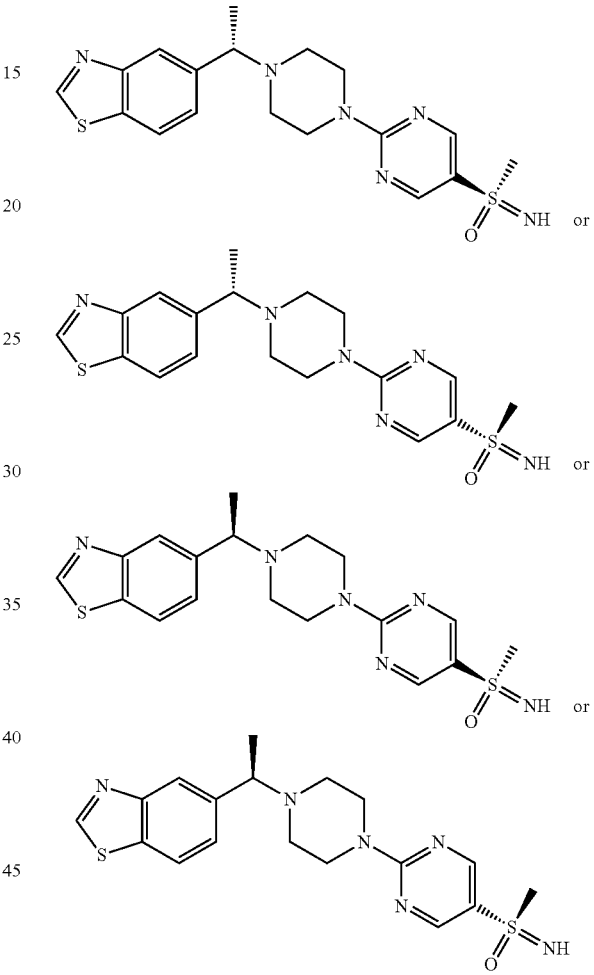

To a stirred solution of intermediate 7 (400 mg, 1.41 mmol) in ACN (5 mL), TEA (0.6 mL, 4.23 mmol) and intermediate 10 (445 mg, 1.54 mmol) were added at RT and stirred overnight. Completion of the reaction was monitored by TLC, then the reaction mixture was evaporated at 50° C. under vacuum. To the resulting mixture, water (10 mL) was added and the aqueous layer was extracted with EtOAc (2×50 mL). The combined organic layer was dried over anhydrous Na₂SO₄ and concentrated under vacuum. The resulting crude material was purified by flash chromatography (silica gel: 230-400 mesh, eluent: 50% EtOAc in pet-ether) to obtain the pure intermediate N-((6-(4-(1-(benzo[d]thiazol-5-yl)ethyl)piperazin-1-yl)pyridin-3-yl)(methyl)(oxo)-λ⁶-sulfanylidene)-2,2,2-trifluoroacetamide. Yield: 39% (273 mg, off white solid).

To this intermediate, methanol (7 mL, 20 V) and K₂CO₃ (414 mg, 4.53 mmol) were added and stirred at RT for 20 min. After 20 min, the reaction mixture was filtered through celite and concentrated under vacuum. To the resulting mixture, water (50 mL) was added and the aqueous layer was extracted with DCM (2×100 mL). The combined organic layer was dried over anhydrous Na₂SO₄ and concentrated under vacuum. The resulting crude material was purified by flash chromatography (Biotage Isolera, gradient: 1-2% methanol in DCM) to afford the title compound. Yield: 34% (190 mg, off white solid). ¹H NMR (400 MHz, DMSO-d₆): δ 9.39 (s, 1H), 8.65 (s, 2H), 8.12 (d, J=8.4 Hz, 1H), 8.03 (s, 1H), 7.51-7.49 (m, 1H), 4.24 (s, 1H), 3.86-3.83 (m, 4H), 3.69-3.67 (m, 1H), 3.07 (s, 3H), 2.54-2.39 (m, 4H), 1.41 (d, J=6.8 Hz, 3H). LCMS: (Method A) 402.8 (M+H), Rt. 1.8 min, 99.7% (Max). HPLC: (Method A) Rt. 1.8 min, 99.8% (Max).

To a stirred solution of intermediate 7 (400 mg, 1.41 mmol) in ACN (5 mL), TEA (0.6 mL, 4.23 mmol) and intermediate 11 (445 mg, 1.54 mmol) were added at RT and stirred overnight. Completion of the reaction was monitored by TLC, then the reaction mixture was evaporated at 50° C. under vacuum. To the resulting mixture, water (10 mL) was added and the aqueous layer was extracted with EtOAc (2×50 mL). The combined organic layer was dried over anhydrous Na₂SO₄ and concentrated under vacuum. The resulting crude material was purified by flash chromatography (silica gel: 230-400 mesh, eluent: 50% EtOAc in pet-ether) to obtain the pure intermediate. Yield: 39% (273 mg, off white solid).

To this intermediate methanol (7 mL, 20 V) and K₂CO₃ (414 mg, 4.53 mmol) were added and stirred at RT for 20 min. After 20 min, the reaction mixture was filtered through celite and concentrated under vacuum. To the resulting mixture, water (50 mL) was added and the aqueus layer was extracted with DCM (2×100 mL). The combined organic layer was dried over anhydrous Na₂SO₄ and concentrated under vacuum. The resulting crude material was purified by flash chromatography (Biotage Isolera, gradient: 1-2% methanol in DCM) to afford the title compound. Yield: 10% (15 mg, off white solid). $^1$H NMR (400 MHz, DMSO-$d_6$): δ 9.39 (s, 1H), 8.65 (s, 2H), 8.13 (d, J=8.0 Hz, 1H), 8.03 (s, 1H), 7.51-7.49 (m, 1H), 4.24 (s, 1H), 3.86-3.83 (m, 4H), 3.69-3.67 (m, 1H), 3.07 (s, 3H), 2.54-2.39 (m, 4H), 1.41 (d, J=6.8 Hz, 3H). LCMS: (Method A) 403.3 (M+H), Rt. 1.8 min, 99.6% (Max). HPLC: (Method A) Rt. 1.8 min, 99.2% (Max). Chiral SFC: (Method B) Rt 9.3 min, 99.9% (Max). $[α]^{25}_D$=−107.69, c 0.104 (MeOH).

Example 36: (S)-(2-(4-((S)-1-(benzo[d]thiazol-5-yl)ethyl)piperazin-1-yl)pyrimidin-5-yl)(imino)(methyl)-$λ^6$-sulfanone or (R)-(2-(4-((S)-1-(benzo[d]thiazol-5-yl)ethyl)piperazin-1-yl)pyrimidin-5-yl)(imino)(methyl)-$λ^6$-sulfanone or (S)-(2-(4-((R)-1-(benzo[d]thiazol-5-yl)ethyl)piperazin-1-yl)pyrimidin-5-yl)(imino)(methyl)-$λ^6$-sulfanone or (R)-(2-(4-((R)-1-(benzo[d]thiazol-5-yl)ethyl)piperazin-1-yl)pyrimidin-5-yl)(imino)(methyl)-$λ^6$-sulfanone

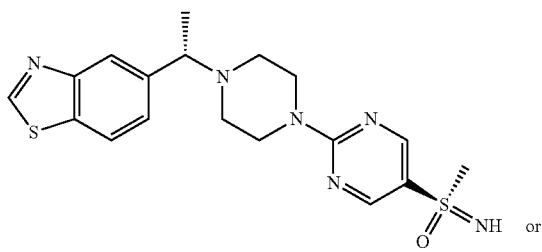

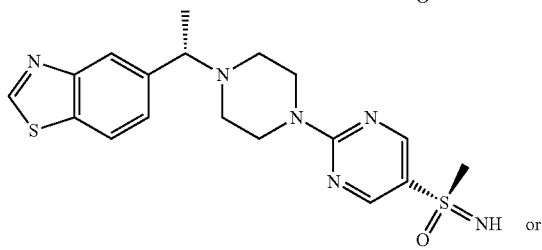

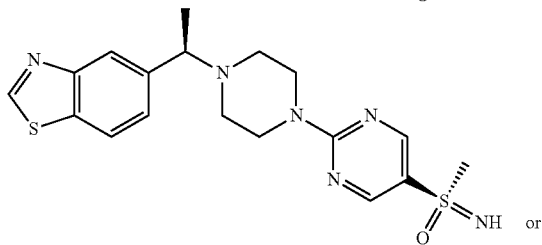

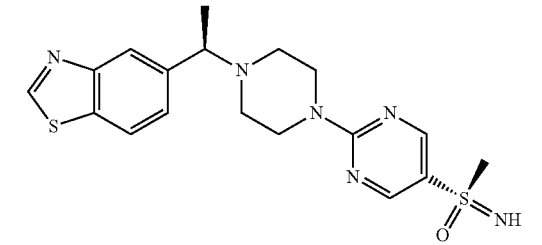

To a stirred solution of intermediate 7 (400 mg, 1.41 mmol) in ACN (5 mL), TEA (0.6 mL, 4.23 mmol) and intermediate 12 (445 mg, 1.54 mmol) were added and the reaction mixture was stirred overnight at RT. Completion of the reaction was monitored by TLC, then the reaction mixture was evaporated at 50° C. under vacuum. To the resulting mixture, water (10 mL) was added and the aqueous layer was extracted with EtOAc (2×50 mL). The combined organic layer was dried over anhydrous Na₂SO₄ and concentrated under vacuum. The resulting crude material was purified by flash chromatography (silica gel: 230-400 mesh, eluent: 50% EtOAc in pet-ether) to obtain the pure intermediate. Yield: 39% (273 mg, off white solid).

To this intermediate, methanol (7 mL, 20 V) and K₂CO₃ (414 mg, 4.53 mmol) were added and stirred for 20 min. After 20 min, the reaction mixture was filtered through celite and concentrated under vacuum. To the resulting mixture, water (50 mL) was added and the aqueous layer was extracted with DCM (2×100 mL). The combined organic layer was dried over anhydrous Na₂SO₄ and concentrated under vacuum. The resulting crude material was purified by flash chromatography (Biotage Isolera, gradient: 1-2% methanol in DCM) to afford the title compound. Yield: 14% (22 mg, off white solid). $^1$H NMR (400 MHz, DMSO-$d_6$): δ 9.39 (t, J=2.0 Hz, 1H), 8.65 (t, J=2.0 Hz, 2H), 8.12 (d, J=8.4 Hz, 1H), 8.03 (s, 1H), 7.50 (d, J=8.4 Hz, 1H), 4.24 (s, 1H), 3.84-3.82 (m, 4H), 3.68 (d, J=6.4 Hz, 1H), 3.07 (s, 3H), 2.51-2.34 (m, 4H), 1.41 (d, J=6.4 Hz, 3H). LCMS: (Method A) 403.3 (M+H), Rt. 1.8 min, 93.9% (Max). HPLC: (Method A) Rt. 1.9 min, 94.5% (Max). Chiral SFC: (Method B) Rt 10.2 min, 98.8% (Max). $[α]^{25}_D$=−18.64, c 0.103 (MeOH).

Example 37: (S)-(2-(4-((S)-1-(benzo[d]thiazol-5-yl)ethyl)piperazin-1-yl)pyrimidin-5-yl)(methyl)(methylimino)-$λ^6$-sulfanone or (R)-(2-(4-((S)-1-(benzo[d]thiazol-5-yl)ethyl)piperazin-1-yl)pyrimidin-5-yl)(methyl)(methylimino)-$λ^6$-sulfanone or (S)-(2-(4-((R)-1-(benzo[d]thiazol-5-yl)ethyl)piperazin-1-yl)pyrimidin-5-yl)(methyl)(methylimino)-$λ^6$-sulfanone or (R)-(2-(4-((R)-1-(benzo[d]thiazol-5-yl)ethyl)piperazin-1-yl)piperazin-1-yl)pyrimidin-5-yl)(methyl)(methylimino)-$λ^6$-sulfanone

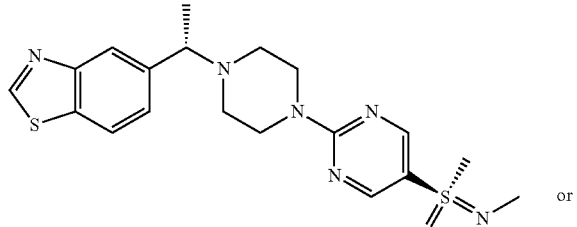

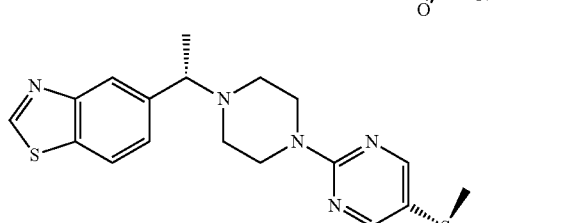

-continued

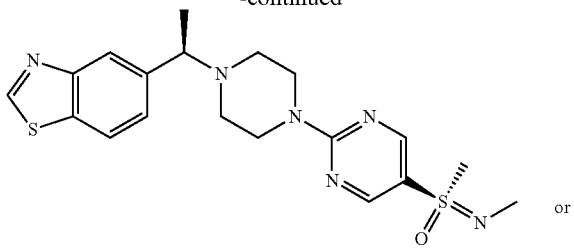

or

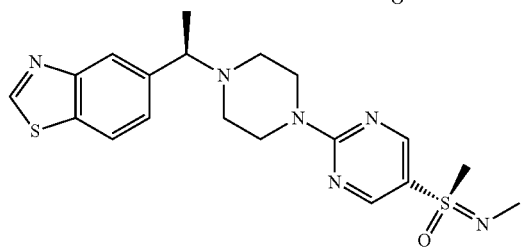

To a stirred solution of example 35 (150 mg, 0.372 mmol) in DMF (5 mL), NaH (60%) (35.79 mg, 0.74 mmol) was added at 0° C. and stirred for 15 min. Then iodomethane (0.05 mL, 0.74 mmol) was added to the reaction mixture and stirred at RT for 2 h. After completion of the reaction (monitored by TLC), the reaction mixture was quenched with ice cold water (10 mL) and the aqueous layer was extracted with EtOAc (2×50 mL). The combined organic layer was dried over anhydrous $Na_2SO_4$ and concentrated under vacuum. The resulting crude material was purified by flash chromatography (Biotage Isolera, gradient: 1-2% methanol in DCM) to afford the title compound. Yield: 27% (41.2 mg, off white solid). $^1$H NMR (400 MHz, DMSO-$d_6$): δ 9.39 (s, 1H), 8.55 (s, 2H), 8.12 (d, J=8.0 Hz, 1H), 8.03 (s, 1H), 7.51 (d, J=1.6, 8.0 Hz, 1H), 3.87-3.84 (m, 4H), 3.71-3.66 (m, 1H), 3.11 (s, 3H), 2.56-2.42 (m, 7H), 1.41 (d, J=6.8 Hz, 3H). LCMS: (Method A) 417.0 (M+H), Rt. 1.9 min, 98.1% (Max). HPLC: (Method A) Rt. 1.9 min, 98.5% (Max).

Example 38: (R)-(2-(4-(1-(benzo[d]thiazol-5-yl)ethyl)piperazin-1-yl)pyrimidin-5-yl)(imino)(methyl)-λ$^6$-sulfanone or (S)-(2-(4-(1-(benzo[d]thiazol-5-yl)ethyl)piperazin-1-yl)pyrimidin-5-yl)(imino)(methyl)-λ$^6$-sulfanone

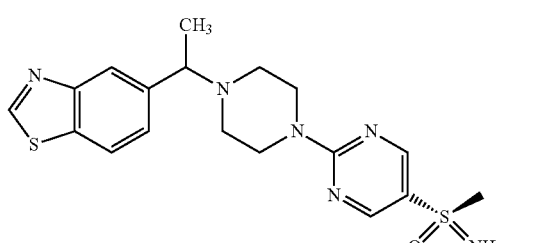

or

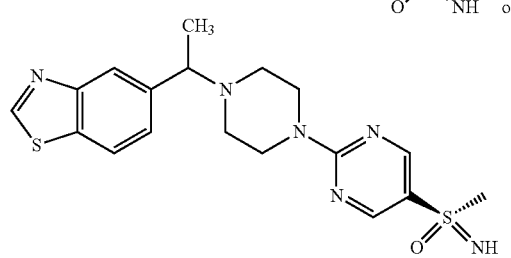

Step 1: N—((R)-(2-(4-(1-(benzo[d]thiazol-5-yl)ethyl)piperazin-1-yl)pyrimidin-5-yl)(methyl)(oxo)-λ$^6$-sulfanylidene)-2,2,2-trifluoroacetamide or N—((S)-(2-(4-(1-(benzo[d]thiazol-5-yl)ethyl)piperazin-1-yl)pyrimidin-5-yl)(methyl)(oxo)-λ$^6$-sulfanylidene)-2,2,2-trifluoroacetamide To a stirred solution of intermediate 6 (0.47 g, 1.46 mmol) in ACN (2.0 mL,), TEA (0.88 mL, 5.8 mmol) and intermediate 12 (464 mg 1.6 mmol) were added and the reaction mixture was stirred at RT for 30 min. Completion of the reaction was monitored by TLC, then the reaction mixture was concentrated under vacuum. The resulting crude material was purified by flash chromatography (Biotage Isolera, 60-80% EtOAc in pet ether) to afford the title compound. Yield: 44% (320 mg, white solid). $^1$H NMR (400 MHz, DMSO-$d_6$): δ 9.39 (s, 1H), 8.75 (s, 2H), 8.13 (d, J=8.4 Hz, 1H), 8.04 (s, 1H), 7.51 (d, J=8.4 Hz, 1H), 3.89 (t, J=4.8 Hz, 4H), 3.76 (s, 3H), 3.70 (d, J=6.8 Hz, 1H), 2.58-2.43 (m, 4H), 1.41 (d, J=6.4 Hz, 3H). LCMS: (Method A) 268.0 (M+H), Rt. 1.9 min, 92.8% (Max). HPLC: (Method A) Rt. 3.8 min, 96.1% (Max).

Step 2: (R)-(2-(4-(1-(benzo[d]thiazol-5-yl)ethyl)piperazin-1-yl)pyrimidin-5-yl)(imino)(methyl)-λ$^6$-sulfanone or (S)-(2-(4-(1-(benzo[d]thiazol-5-yl)ethyl)piperazin-1-yl)pyrimidin-5-yl)(imino)(methyl)-λ$^6$-sulfanone To a stirred solution of the product of step 1 (310 mg, 0.62 mmol) in MeOH (2 mL) and DCM (1 mL), $K_2CO_3$ (200 mg, 1.0 mmol) was added and stirred for 1 h. Completion of the reaction was monitored by TLC, then the reaction mixture was concentrated under vacuum. The resulting crude material was purified by flash chromatography (Biotage Isolera, gradient: 3-4% methanol in DCM) to afford the title compound. Yield: 84% (210 g, white solid). $^1$H NMR (400 MHz, DMSO-$d_6$): δ 9.38 (s, 1H), 8.64 (s, 2H), 8.11 (d, J=8.4 Hz, 1H), 8.02 (s, 1H), 7.49 (dd, J=8.2, 1.2 Hz, 1H), 4.23 (s, 1H), 3.84 (t, J=4.8 Hz, 4H), 3.06 (s, 3H), 2.54-2.41 (m, 4H), 1.40 (d, J=6.4 Hz, 3H). LCMS: (Method A) 403.1 (M+H), Rt. 1.6 min, 99.9% (Max). HPLC: (Method A) Rt. 1.9 min, 99.7% (Max).

Example 39: (R)-(2-(4-(1-(benzo[d]thiazol-5-yl)ethyl)piperazin-1-yl)pyrimidin-5-yl)(imino)(methyl)-λ$^6$-sulfanone or (S)-(2-(4-(1-(benzo[d]thiazol-5-yl)ethyl)piperazin-1-yl)pyrimidin-5-yl)(imino)(methyl)-λ$^6$-sulfanone

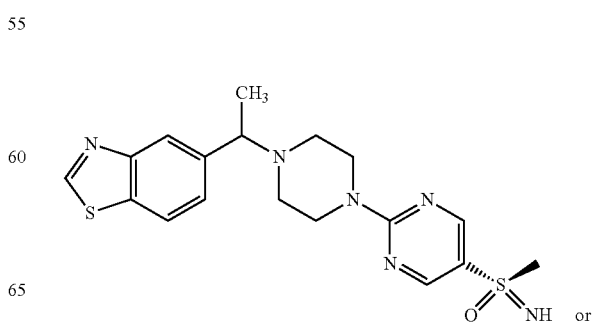

or

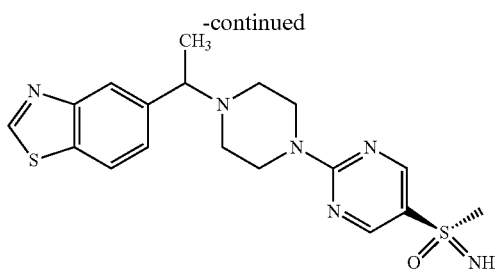

To a stirred solution of intermediate 6 (0.47 g, 1.46 mmol) in ACN (2.0 mL), TEA (0.88 mL, 5.80 mmol) and intermediate 11 (464 mg 1.60 mmol) were added at RT and the reaction mixture was stirred for 30 min at RT. Completion of the reaction was monitored by TLC, then the reaction mixture was concentrated under vacuum. The resulting crude material was purified by flash chromatography (Biotage Isolera, 60-80% EtOAc in pet ether) to afford the pure intermediate N—((R)-(2-(4-(1-(benzo[d]thiazol-5-yl)ethyl) piperazin-1-yl)pyrimidin-5-yl)(methyl)(oxo)-$\lambda^6$-sulfanylidene)-2,2,2-trifluoroacetamide or N—((S)-(2-(4-(1-(benzo[d]thiazol-5-yl)ethyl)piperazin-1-yl)pyrimidin-5-yl) (methyl)(oxo)-$\lambda^6$-sulfanylidene)-2,2,2-trifluoroacetamide. Yield: 44% (320 mg, white solid). $^1$H NMR (400 MHz, DMSO-$d_6$): δ 9.39 (s, 1H), 8.75 (s, 2H), 8.13 (d, J=8.4 Hz, 1H), 8.04 (s, 1H), 7.51 (d, J=8.4 Hz, 1H), 3.89 (t, J=4.8 Hz, 4H), 3.76 (s, 3H), 3.70 (d, J=6.8 Hz, 1H), 2.58-2.43 (m, 4H), 1.41 (d, J=6.4 Hz, 3H). LCMS: (Method A) 403.1.0 (M+H), Rt. 1.9 min, 92.8% (Max). HPLC: (Method A) Rt. 3.8 min, 96.1% (Max).

To a stirred solution of this intermediate (310 mg, 0.62 mol) in MeOH (2 mL) and DCM (1 mL), K$_2$CO$_3$ (200 mg, 1.0 mol) was added and stirred for 1 h at RT. Completion of the reaction was monitored by TLC, then the reaction mixture was concentrated under vacuum. The resulting crude material was purified by flash chromatography (Biotage Isolera, gradient: 3-4% methanol in DCM) to afford the title compound. Yield: 84% (210 g, white solid). $^1$H NMR (400 MHz, DMSO-$d_6$): δ 9.38 (s, 1H), 8.64 (s, 2H), 8.11 (d, J=8.4 Hz, 1H), 8.02 (s, 1H), 7.49 (dd, J=8.2, 1.2 Hz, 1H), 4.23 (s, 1H), 3.84 (t, J=4.8 Hz, 4H), 3.06 (s, 3H), 2.54-2.41 (m, 4H), 1.40 (d, J=6.4 Hz, 3H). LCMS: (Method A) 403.1 (M+H), Rt. 1.6 min, 99.9% (Max). HPLC: (Method A) Rt. 1.9 min, 99.7% (Max).

Example 40: (S)-(2-(4-((R)-1-(benzo[d]thiazol-5-yl) ethyl)piperazin-1-yl)pyrimidin-5-yl)(imino)(methyl)-$\lambda^6$-sulfanone or (R)-(2-(4-((R)-1-(benzo[d]thiazol-5-yl)ethyl)piperazin-1-yl)pyrimidin-5-yl)(imino) (methyl)-$\lambda^6$-sulfanone or (S)-(2-(4-((S)-1-(benzo[d] thiazol-5-yl)ethyl)piperazin-1-yl)pyrimidin-5-yl) (imino)(methyl)-$\lambda^6$-sulfanone or (R)-(2-(4-((S)-1-(benzo[d]thiazol-5-yl)ethyl)piperazin-1-yl) pyrimidin-5-yl)(imino)(methyl)-$\lambda^6$-sulfanone

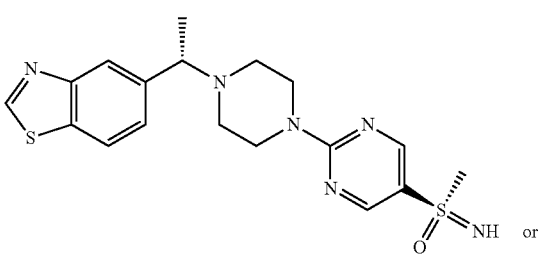

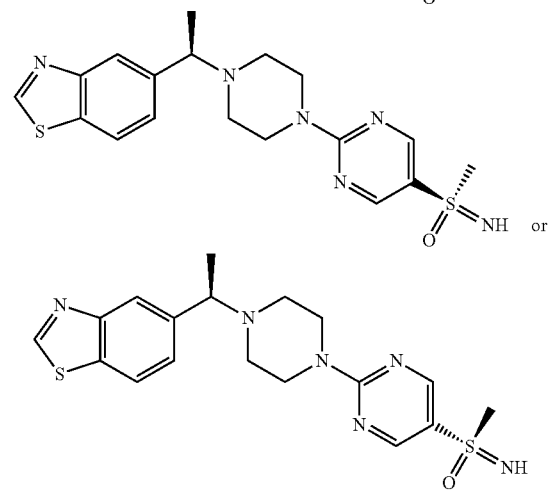

The mixture of two enantiomers obtained from example 39 was separated by SFC (Method H: 20 mM ammonia in methanol, column: YMC Cellulose C). The first eluting peak was concentrated to afford the title compound. Yield: 21% (35 mg, off white solid). $^1$H NMR: (400 MHz, DMSO-$d_6$): δ 9.38 (s, 1H), 8.65 (s, 2H), 8.12 (d, J=8.0 Hz, 1H), 8.02 (s, 1H), 7.49 (d, J=8.0 Hz, 1H), 4.23 (s, 1H), 3.84 (d, J=4.4 Hz, 4H), 3.67 (d, J=6.4 Hz, 1H), 3.06 (s, 3H), 2.44-2.40 (m, 2H), 1.41 (d, J=6.40 Hz, 3H). LCMS: (Method A) 403.1 (M+H), Rt 1.6 min, 99.3% (Max). HPLC: (Method A) Rt 1.8 min, 98.9% (Max). Chiral SFC: (Method B) Rt. 8.1 min, 100% (Max).

Example 41: (S)-(2-(4-((R)-1-(benzo[d]thiazol-5-yl) ethyl)piperazin-1-yl)pyrimidin-5-yl)(imino)(methyl)-$\lambda^6$-sulfanone or (R)-(2-(4-((R)-1-(benzo[d]thiazol-5-yl)ethyl)piperazin-1-yl)pyrimidin-5-yl)(imino) (methyl)-$\lambda^6$-sulfanone or (S)-(2-(4-((S)-1-(benzo[d] thiazol-5-yl)ethyl)piperazin-1-yl)pyrimidin-5-yl) (imino)(methyl)-$\lambda^6$-sulfanone or (R)-(2-(4-((S)-1-(benzo[d]thiazol-5-yl)ethyl)piperazin-1-yl) pyrimidin-5-yl)(imino)(methyl)-$\lambda^6$-sulfanone

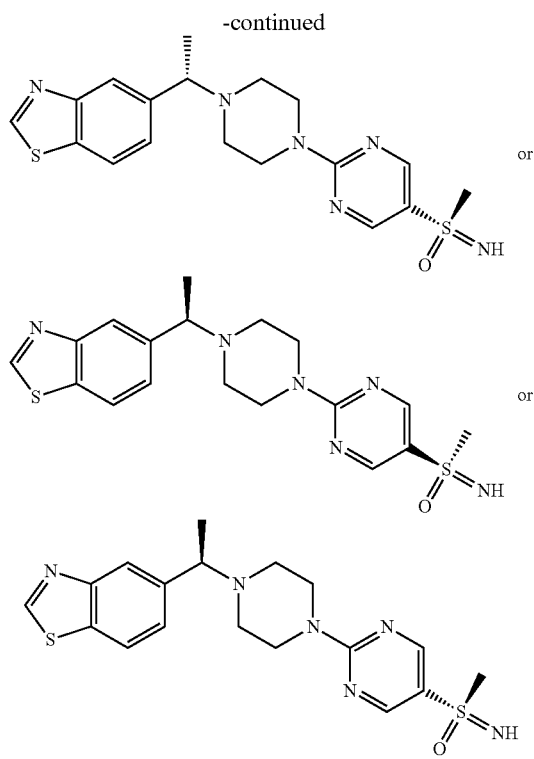

The mixture of two enantiomers of example 38 was separated by SFC (Method H: 20 mM ammonia in methanol, column: YMC Cellulose C). The first eluting peak was concentrated to afford the title compound. Yield: 28% (46 mg, off white solid). $^1$H NMR: (400 MHz, DMSO-d$_6$): δ 9.39 (d, J=1.6 Hz, 1H), 8.66 (d, J=1.6 Hz, 2H), 8.13 (q, J=1.6 Hz, 1H), 8.03 (s, 1H), 7.51 (d, J=8.4 Hz, 1H), 4.25 (s, 1H), 3.85 (m, 4H), 3.69 (d, J=6.8 Hz, 1H), 3.08 (s, 3H), 2.45-2.34 (m, 2H), 1.42 (d, J=6.40 Hz, 3H). LCMS: (Method A) 403.1 (M+H), Rt 1.6 min, 99.7% (Max). HPLC: (Method A), Rt 1.9 min, 99.5% (Max). Chiral SFC: (Method B) Rt. 9.33 min, 100% (Max).

Example 42: Imino(methyl)(2-(4-(1-(2-methylbenzo[d]thiazol-5-yl)ethyl)piperazin-1-yl)pyrimidin-5-yl)-λ$^6$-sulfanone

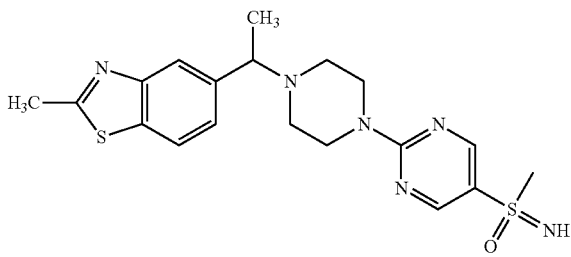 [SMILES: Cc1nc2cc(C(C)N3CCN(c4ncc(S(C)(=N)=O)cn4)CC3)ccc2s1]

To a stirred solution of intermediate 8 (0.88 g, 3.80 mmol) in DMF(11.0 mL, 10 V), TEA (1.6 mL, 11.41 mmol) and intermediate 10 (1.1 g, 3.80 mmol) were added and the reaction mixture was stirred overnight at RT. Completion of the reaction was monitored by TLC, then the reaction mixture was concentrated under vacuum. The resulting crude material was purified by flash chromatography (Biotage Isolera, eluent: 60% EtOAc in pet ether) to afford the pure intermediate 2,2,2-trifluoro-N-(methyl(2-(4-(1-(2-methylbenzo[d]thiazol-5-yl)ethyl)piperazin-1-yl)pyrimidin-5-yl)(oxo)-λ$^6$-sulfanylidene)acetamide. Yield: 22% (246 mg, white solid).

To this intermediate methanol (22.0 mL, 20 V) and K$_2$CO$_3$ (1.46 g, 11.41 mmol) were added and stirred for 20 min. After 20 min, the reaction mixture was filtered through celite and concentrated under vacuum. To the resulting mixture, water (50 mL) was added and the aqueous layer was extracted with DCM (2×100 mL). The combined organic layer was dried over anhydrous Na$_2$SO$_4$ and concentrated under vacuum. The resulting crude material was purified by flash chromatography (Biotage Isolera, gradient: 1-2% methanol in EtOAc) to afford the title compound. Yield: 23% (15 mg, white solid). $^1$H NMR (400 MHz, DMSO-d$_6$): δ 8.65 (s, 2H), 7.97 (d, J=8.0 Hz, 1H), 7.84 (s, 1H), 7.38 (d, J=8.4 Hz, 1H), 4.23 (s, 1H), 3.84 (t, J=4.8 Hz, 4H), 3.63 (d, J=6.8 Hz, 1H), 3.06 (s, 3H), 2.60 (s, 3H), 2.43-2.39 (m, 4H), 1.39 (d, J=6.8 Hz, 3H). LCMS: (Method A) 417.3 (M+H), Rt. 2.1 min, 97.3% (Max). HPLC: (Method A) Rt. 2.2 min, 97.1% (Max).

Example 43: ethyl(imino)(2-(4-(1-(2-methylbenzo[d]thiazol-5-yl)ethyl)piperazin-1-yl)pyrimidin-5-yl)-λ$^6$-sulfanone

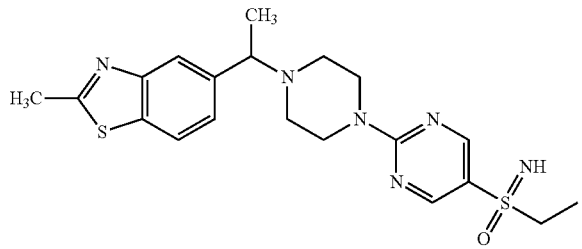 [SMILES: CCS(=N)(=O)c1cnc(N2CCN(C(C)c3ccc4sc(C)nc4c3)CC2)nc1]

To a stirred solution of intermediate 8 (0.25 g, 1.01 mmol) in DMF (2.50 mL, 10 V), TEA (0.4 mL, 3.03 mmol) and intermediate 13 were added (0.30 g, 1.01 mmol) at RT and stirred overnight. Completion of the reaction was monitored by TLC, then the reaction mixture was concentrated under vacuum. The resulting crude material was purified by flash chromatography (Biotage Isolera, eluent: 40% EtOAc in pet ether) to afford the intermediate N-(ethyl(2-(4-(1-(2-methylbenzo[d]thiazol-5-yl)ethyl)piperazin-1-yl)pyrimidin-5-yl)(oxo)-λ$^6$-sulfanylidene)-2,2,2-trifluoroacetamide. Yield: 94% (0.48 g, pale yellow gummy solid).

To this intermediate methanol (2.5 mL, 20 V) and K$_2$CO$_3$ (0.40 g, 3.23 mmol) were added and stirred at RT for 20 min. After 20 min, the reaction mixture was filtered through celite and concentrated under vacuum. To the resulting mixture, water (50 mL) was added and the aqueous layer was extracted with DCM (2×100 mL). The combined organic layer was dried over anhydrous Na$_2$SO$_4$ and concentrated under vacuum. The resulting crude material was purified by flash chromatography (Biotage Isolera, gradient: 1-2% methanol in EtOAc) to afford the title compound. Yield: 5% (20 mg, white solid). $^1$H NMR (400 MHz, DMSO-d$_6$): δ 8.58 (s, 2H), 7.97 (d, J=8.4 Hz, 1H), 7.84 (s, 1H), 7.38 (d, J=7.6 Hz, 1H), 4.22 (s, 1H), 3.83 (t, J=4.4 Hz, 4H), 3.65-3.60 (m, 1H), 3.17-3.08 (m, 2H), 2.78 (s, 3H), 2.52-2.32 (m, 4H), 1.38 (d, J=6.4 Hz, 3H), 1.07 (t, J=7.2 Hz, 3H). LCMS:

(Method A) 431.3 (M+H), Rt. 2.5 min, 98.2% (Max). HPLC: (Method A) Rt. 2.2 min, 98.3% (Max).

Example 44: Imino(2-(4-(1-(2-methylbenzo[d]thiazol-5-yl)ethyl)piperazin-1-yl)pyrimidin-5-yl)(propyl)-λ⁶-sulfanone

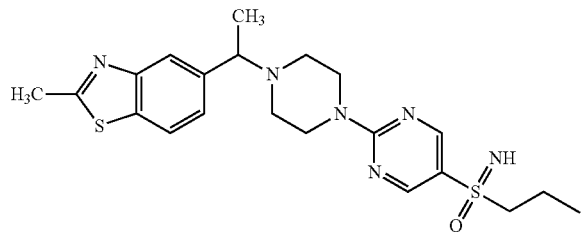 [SMILES: CCCS(=N)(=O)c1cnc(N2CCN(C(C)c3ccc4sc(C)nc4c3)CC2)nc1]

To a stirred solution of intermediate 8 (249 mg, 9.50 mmol) in DMF (2.5 mL), TEA (0.5 mL, 3.80 mmol) and intermediate 14 (300 mg, 9.50 mmol) were added at RT and stirred overnight. Completion of the reaction was monitored by TLC, then the reaction mixture was evaporated at 50° C. under vacuum. To the resulting mixture, water (2 mL) was added and the aqueous layer was extracted with EtOAc (2×50 mL). The combined organic layer was dried over $Na_2SO_4$ and concentrated under vacuum. The resulting crude material was purified by flash chromatography (silica gel: 230-400 mesh, eluent: 50% EtOAc in pet-ether) to afford the pure intermediate 2,2,2-trifluoro-N-((2-(4-(1-(2-methylbenzo[d]thiazol-5-yl)ethyl)piperazin-1-yl)pyrimidin-5-yl)(oxo)(propyl)-λ⁶-sulfanylidene)acetamide. Yield: 27% (136 mg, off white solid).

To this intermediate methanol (7 mL, 20 V) and $K_2CO_3$ (414 mg, 4.53 mmol) were added and stirred for 20 min. After 20 min, the reaction mixture was filtered through celite and concentrated under vacuum. To the resulting mixture, water (20 mL) was added and the aqueous layer was extracted with DCM (2×100 mL). The combined organic layer was dried over anhydrous $Na_2SO_4$ and concentrated under vacuum. The resulting crude material was purified by flash chromatography (Biotage Isolera, gradient: 1-2% methanol in DCM) to afford the title compound. Yield: 18% (26.5 mg, off white solid). ¹H NMR (400 MHz, DMSO-$d_6$): δ 8.59 (s, 2H), 7.97 (d, J=8.0 Hz, 1H), 7.85 (s, 1H), 7.38 (d, J=8.4 Hz, 1H), 4.22 (s, 1H), 3.85-3.83 (m, 4H), 3.66-3.61 (m, 1H), 3.12-3.08 (m, 2H), 2.79 (s, 3H), 2.49-2.39 (m, 2H), 1.57-1.51 (m, 2H), 1.39 (d, J=6.40 Hz, 3H), 0.88 (t, J=7.20 Hz, 3H). LCMS: (Method A) 445.2 (M+H), Rt. 2.2 min, 99.7% (Max). HPLC: (Method A) Rt 2.4 min, 99.7% (Max).

Example 45: methyl(2-(4-(1-(2-methylbenzo[d]thiazol-5-yl)ethyl)piperazin-1-yl)pyrimidin-5-yl)(methylimino)-λ⁶-sulfanone

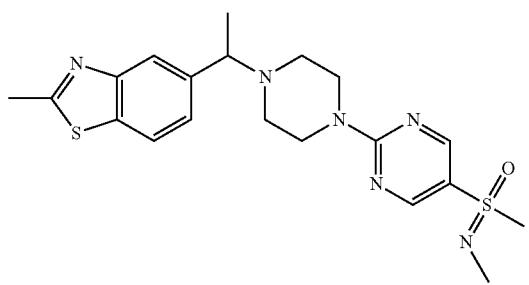

To a stirred solution of example 42 (0.15 g, 0.36 mmol) in THF (1.5 mL, 10V), NaH (60%) (26 mg, 0.54 mmol) was added at 0° C. and stirred for 15 min. Then MeI (0.05 mL, 0.9 mmol) was added to the reaction mixture in a sealed tube and heated overnight at 90° C. After completion of the reaction (monitored by TLC), the reaction mixture was concentrated under vacuum and the resulting crude material was purified by flash chromatography (Biotage Isolera, eluent: 5-6% methanol in DCM). The obtained material was further purified by Prep. HPLC (Method B) to afford the title compound. Yield: 9% (13 mg, off white solid). ¹H NMR (400 MHz, DMSO-$d_6$): δ 8.55 (s, 2H), 7.97 (d, J=8.4 Hz, 1H), 7.84 (s, 1H), 7.39 (d, J=8.4 Hz, 1H), 3.85-3.84 (m, 4H), 3.64-3.62 (m, 1H), 3.10 (s, 3H), 2.78 (s, 3H), 2.54-2.53 (m, 2H), 2.46 (s, 3H), 2.44-2.42 (m, 2H), 1.39 (d, J=6.8 Hz, 3H). LCMS: (Method A) 430.8 (M+H), Rt. 2.2 min, 98.7% (Max). HPLC: (Method A) Rt. 2.1 min, 99.3% (Max).

Example 46: imino(methyl)(6-(4-(1-(2-methylbenzo[d]thiazol-5-yl)ethyl)piperazin-1-yl)pyridin-3-yl)-λ⁶-sulfanone

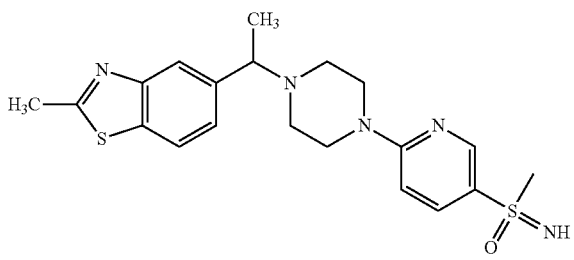 [SMILES: Cc1nc2cc(C(C)N3CCN(c4ccc(S(C)(=N)=O)cn4)CC3)ccc2s1]

To a stirred solution of intermediate 8 (350 mg, 1.34 mmol) in DMF (3.5 mL), TEA (0.6 mL, 4.02 mmol) and intermediate 15 (422 mg, 1.47 mmol) were added at RT and stirred overnight. Completion of the reaction was monitored by TLC, then the reaction mixture was evaporated at 50° C. under vacuum. To the resulting mixture, water (10 mL) was added and the aqueous layer was extracted with EtOAc (2×50 mL). The combined organic layer was dried over anhydrous $Na_2SO_4$ and concentrated under vacuum. The resulting crude material was purified by flash chromatography (silica gel: 230-400 mesh, eluent: 50% EtOAc in pet-ether) to afford the pure intermediate 2,2,2-trifluoro-N-(methyl(6-(4-(1-(2-methylbenzo[d]thiazol-5-yl)ethyl)piperazin-1-yl)pyridin-3-yl)(oxo)-λ⁶-sulfanylidene)acetamide. Yield: 40% (241 mg, off white solid).

To this intermediate methanol (7 mL, 20 V) and $K_2CO_3$ (414 mg, 4.53 mmol) were added and stirred for 20 min. After 20 min, the reaction mixture was filtered through celite and concentrated under vacuum. To the resulting mixture, water (50 mL) was added and the aqueous layer was extracted with DCM (2×100 mL). The combined organic layer was dried over anhydrous $Na_2SO_4$ and concentrated under vacuum. The resulting crude material was purified by flash chromatography (Biotage Isolera, gradient: 1-2% methanol in DCM) to afford the title compound. Yield: 30% (163.7 mg, off white solid). ¹H NMR (400 MHz, DMSO-$d_6$): δ 8.48 (d, J=2.4 Hz, 1H), 7.96 (d, J=8.4 Hz, 1H), 7.86-7.84 (m, 2H), 7.38 (dd, J=8.0, 1.2 Hz, 1H), 6.87 (d, J=9.2 Hz, 1H), 4.02 (s, 1H), 3.63-3.59 (m, 5H), 3.00 (s, 3H), 2.78 (s, 3H), 2.54-2.49 (m, 2H), 2.43-2.37 (m, 2H), 1.38 (d, J=6.8 Hz, 3H). LCMS: (Method A) 415.8 (M+H), Rt. 2.1 min, 99.0% (Max). HPLC: (Method A) Rt. 2.1 min, 99.2% (Max).

Example 47: methyl(6-(4-(1-(2-methylbenzo[d]thiazol-5-yl)ethyl)piperazin-1-yl)pyridin-3-yl)(methylimino)-λ⁶-sulfanone

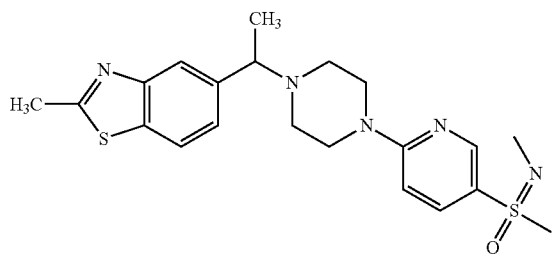

To the stirred solution of example 46 (0.11 g, 0.26 mmol) in THF (2 mL), NaH (60%) (0.03 g, 0.52 mmol) was added at 0° C. and stirred for 15 min. Then MeI (0.05 mL, 0.79 mmol) was added to the reaction mixture and stirred at RT overnight. After completion of the reaction (monitored by TLC), the reaction mixture was quenched with ice cold water (2 mL) and the aqueous layer was extracted with EtOAc (2×15 mL). The combined organic layer was dried over anhydrous Na$_2$SO$_4$ and evaporated under vacuum. The resulting crude material was purified by Prep HPLC (Method B) to afford the tittle compound. Yield: 15% (17 mg, off white solid). $^1$H NMR (400 MHz, DMSO-d$_6$): δ 8.37 (d, J=2.4 Hz, 1H), 7.97 (d, J=8.4 Hz, 1H), 7.85 (s, 1H), 7.76-7.73 (m, 1H), 7.39 (d, J=8.4 Hz, 1H), 6.91 (d, J=9.2 Hz, 1H), 3.63-3.58 (m, 5H), 3.04 (s, 3H), 2.79 (s, 3H), 2.51-2.48 (m, 2H), 2.44 (s, 3H), 2.44-2.40 (m, 2H), 1.39 (d, J=6.80 Hz, 3H). LCMS: (Method A) 429.8 (M+H), Rt. 2.2 min, 96.2% (Max). HPLC: (Method A) Rt. 2.1 min, 99.6% (Max).

Example 48: (ethylimino)(methyl)(2-(4-(1-(2-methylbenzo[d]thiazol-5-yl)ethyl)piperazin-1-yl)pyrimidin-5-yl)-λ⁶-sulfanone

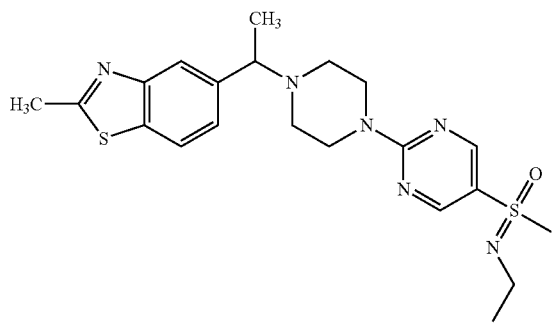

To the stirred solution of example 42 (150 mg, 0.35 mmol) in THF (1.5 mL), NaH (60%) (19 mg, 0.39 mmol) was added at 0° C. and stirred for 15 min. Then EtI (0.18 mL, 0.54 mmol, 3.0 M in THF) was added and stirred at RT overnight. After the completion of the reaction (monitored by TLC), the resulting reaction mixture was poured into ice cold water (2×50 mL) and the aqueous layer was extracted with EtOAc (2×100 mL). The combined organic layer was washed with brine (50 mL), dried over anhydrous Na$_2$SO$_4$ and concentrated under vacuum. The resulting crude material was purified by flash chromatography (Biotage Isolera, gradient: 3% MeOH in DCM) to afford the title compound. Yield: 19% (30 mg, pale-yellow solid). $^1$H NMR (400 MHz, DMSO-d$_6$): δ 8.56 (s, 2H), 7.97 (d, J=8.0 Hz, 1H), 7.85 (s, 1H), 7.39 (dd, J=8.2, 1.2 Hz, 1H), 3.84 (t, J=4.8 Hz, 4H), 3.63 (d, J=6.4 Hz, 1H), 3.10 (s, 3H), 2.84-2.73 (m, 5H), 2.55-2.39 (m, 4H), 1.39 (d, J=6.4 Hz, 3H), 1.03 (t, J=7.20 Hz, 3H). LCMS: (Method A) 445.0 (M+H), Rt. 2.3 min, 91.3% (Max). HPLC: (Method A) Rt. 2.2 min, 92.0% (Max).

Example 49: (isopropylimino)(methyl)(2-(4-(1-(2-methylbenzo[d]thiazol-5-yl)ethyl)piperazin-1-yl)pyrimidin-5-yl)-λ⁶-sulfanone

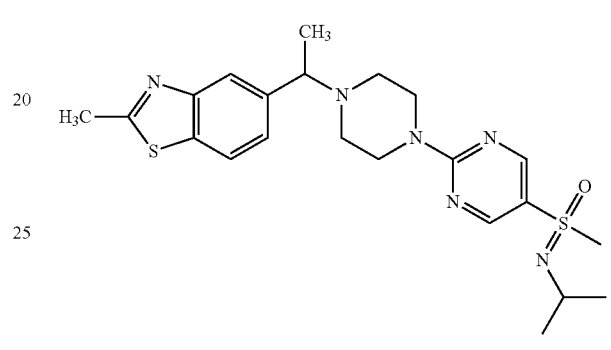

To the stirred solution of example 42 (150 mg, 0.35 mmol) in DMF (1.5 mL), NaH (60%) (19 mg, 0.39 mmol) was added at 0° C. and stirred for 15 min. Then isopropyl iodide (0.1 mL, 1.05 mmol) was added and stirred overnight at 60° C. After completion of the reaction (monitored by TLC), the reaction was quenched with the ice cold water (2×50 mL) and the aqueous layer was extracted with EtOAc (2×100 mL). The combined organic layer was washed with brine (50 mL), dried over anhydrous Na$_2$SO$_4$ and concentrated under vacuum. The resulting crude material was purified by Prep. HPLC (Method A) to afford the title compound. Yield: 8% (11 mg, pale yellow solid). $^1$H NMR (400 MHz, DMSO-d$_6$): δ 8.58 (s, 2H), 7.97 (d, J=8.4 Hz, 1H), 7.85 (s, 1H), 7.39 (dd, J=8.2, 1.2 Hz, 1H), 3.84 (t, J=5.2 Hz, 4H), 3.63 (d, J=6.8 Hz, 1H), 3.15-3.08 (m, 4H), 2.79 (s, 3H), 2.50-2.33 (m, 4H), 1.39 (d, J=6.4 Hz, 3H), 1.05 (d, J=6.4 Hz, 3H), 0.98 (d, J=6.4 Hz, 3H). LCMS: (Method A) 459.0 (M+H), Rt. 2.4 min, 99.3% (Max). HPLC: (Method A) Rt. 2.5 min, 99.3% (Max).

Example 50: imino(methyl)(4-(4-(1-(2-methylbenzo[d]thiazol-5-yl)ethyl)piperazin-1-yl)phenyl)-λ⁶-sulfanone Step 1: 2-methyl-5-(1-(4-(4-(methylthio)phenyl)piperazin-1-yl)ethyl)benzo[d]thiazole

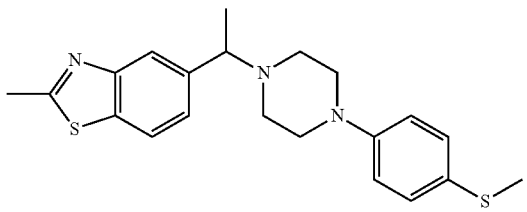

To a stirred solution of intermediate 18 (1.72 g, 6.12 mmol) in DMF (10 mL), TEA (3.45 mL, 24.4 mmol) and Intermediate 2 (1.30 g, 6.12 mmol) were added at RT and stirred overnight at 70° C. After completion of the reaction (monitored by TLC), the reaction mixture was evaporated at 50° C. under vacuum. To the resulting mixture, water (10 mL) was added and the aqueous layer was extracted with EtOAc (2×50 mL). The combined organic layer was dried over anhydrous Na$_2$SO$_4$ and concentrated under vacuum. The resulting crude material was purified by flash chromatography (Biotage Isolera, gradient: 1-2% MeOH in DCM) to afford tittle compound. Yield: 39% (900 mg, off white solid). $^1$H NMR (400 MHz, DMSO-d$_6$): δ 8.13 (d, J=8.4 Hz, 1H), 8.04 (s, 1H), 7.68 (d, J=8.8 Hz, 2H), 7.51 (d, J=8.4 Hz, 1H), 7.01 (d, J=9.2 Hz, 2H), 3.68-3.66 (m, 1H), 3.34-3.30 (m, 4H), 2.96 (s, 3H) 2.37 (s, 3H), 2.68-2.34 (m, 4H), 1.42 (d, J=6.8 Hz, 3H). LCMS: (Method A) 384.3 (M+H), Rt. 2.3 min, 83.3% (Max).

Step 2: 2-methyl-5-(1-(4-(4-(methylsulfinyl)phenyl)piperazin-1-yl)ethyl)benzo[d]thiazole

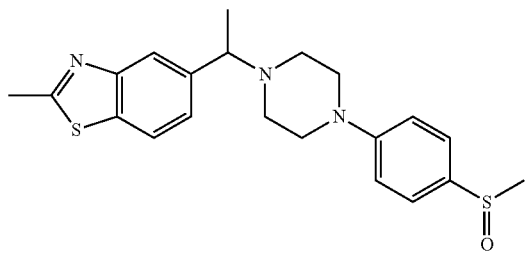

To a stirred solution of 2-methyl-5-(1-(4-(4-(methylthio)phenyl)piperazin-1-yl)ethyl)benzo[d]thiazole (850 mg, 2.21 mmol) in DCM (7 mL, 10 V), m-CPBA (0.5 g, 2.88 mmol) was added portion wise at 0° C. for 60 min. After completion of the reaction (monitored by TLC), the reaction mixture was quenched with 10% NaHCO$_3$ solution and the aqueous layer was extracted with DCM (2×100 mL). The combined organic layer was washed with brine (30 mL), dried over anhydrous Na$_2$SO$_4$ and concentrated under vacuum. The resulting crude material was purified by flash chromatography (Biotage Isolera, eluent: 60-70% EtOAc in pet ether) to afford the title compound. Yield: 51% (450 mg, pale yellow solid). $^1$H NMR (400 MHz, DMSO-d$_6$): δ 8.13 (d, J=8.4 Hz, 1H), 8.04 (s, 1H), 7.68 (d, J=8.8 Hz, 2H), 7.51 (d, J=8.4 Hz, 1H), 7.01 (d, J=9.2 Hz, 2H), 3.68-3.66 (m, 1H), 3.34-3.30 (m, 4H), 2.97 (s, 3H), 2.65 (s, 3H), 2.68-2.34 (m, 4H), 1.42 (d, J=6.8 Hz, 3H). LCMS: (Method A) 400.3 (M+H), Rt. 1.7 min, 83.3% (Max).

Step 3: Imino(methyl)(4-(4-(1-(2-methylbenzo[d]thiazol-5-yl)ethyl)piperazin-1-yl)phenyl)-λ$^6$-sulfanone

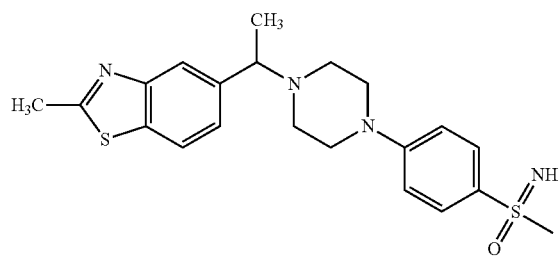

To a stirred solution of 2-methyl-5-(1-(4-(4-(methylsulfinyl)phenyl)piperazin-1-yl)ethyl)benzo[d]thiazole (420 mg, 1.05 mmol) in DCM (8 mL, 20 V), trifluoroacetamide (240 mg, 2.1 mmol), MgO (404 mg, 4.2 mmol), Rh$_2$(OAC)$_4$ (24 mg, 0.05 mmol) and PhI(OAc)$_2$ (507 mg, 1.5 mmol) were added at RT and stirred overnight at same temperature. After completion of the reaction (monitored by TLC), the reaction mixture was filtered through celite and concentrated under vacuum. The resulting crude material was purified by flash chromatography (Biotage Isolera, eluent: 55-60% EtOAc in pet ether) to afford the pure intermediate 2,2,2-trifluoro-N-(methyl(4-(4-(1-(2-methylbenzo[d]thiazol-5-yl)ethyl)piperazin-1-yl)phenyl)(oxo)-λ$^6$-sulfanylidene)acetamide. Yield: 40% (210 mg, off white solid).

To this intermediate, methanol (10 mL, 20 V) and K$_2$CO$_3$ (300 mg, 2.30 mmol) were added and stirred for 20 min. After 20 min, the reaction mixture was filtered through celite and concentrated under vacuum. To the resulting mixture, water (50 mL) was added and the aqueous layer was extracted with DCM (2×100 mL). The combined organic layer was dried over anhydrous Na$_2$SO$_4$ and concentrated under vacuum. The resulting crude material was purified by flash chromatography (Biotage Isolera, gradient: 1-2% methanol in DCM) to afford the title compound. Yield: 4% (16 mg, off white solid). $^1$H NMR (400 MHz, DMSO-d$_6$): δ 7.98 (d, J=8.0 Hz, 1H), 7.86 (s, 1H), 7.68 (d, J=8.8 Hz, 2H), 7.40 (d, J=8.4 Hz, 1H), 7.01 (d, J=8.8 Hz, 2H), 3.86 (s, 1H), 3.61 (d, J=6.4 Hz, 1H), 3.34-3.28 (m, 4H), 2.97 (s, 3H), 2.80 (s, 3H), 2.59-2.46 (m, 4H), 1.40 (d, J=6.4 Hz, 3H). LCMS: (Method A) 415.2 (M+H), Rt. 2.2 min, 96.5% (Max). HPLC: (Method A) Rt. 2.2 min, 96.0% (Max).

Examples 51, 52, 53 and 54: (S)-imino(methyl)(2-(4-((S)-1-(2-methylbenzo[d]thiazol-5-yl)ethyl)piperazin-1-yl)pyrimidin-5-yl)-λ$^6$-sulfanone and (R)-Imino(methyl)(2-(4-((S)-1-(2-methylbenzo[d]thiazol-5-yl)ethyl)piperazin-1-yl)pyrimidin-5-yl)-λ$^6$-sulfanone and (S)-Imino(methyl)(2-(4-((R)-1-(2-methylbenzo[d]thiazol-5-yl)ethyl)piperazin-1-yl)pyrimidin-5-yl)-λ$^6$-sulfanone and (R)-Imino(methyl)(2-(4-((R)-1-(2-methylbenzo[d]thiazol-5-yl)ethyl)piperazin-1-yl)pyrimidin-5-yl)-λ$^6$-sulfanone

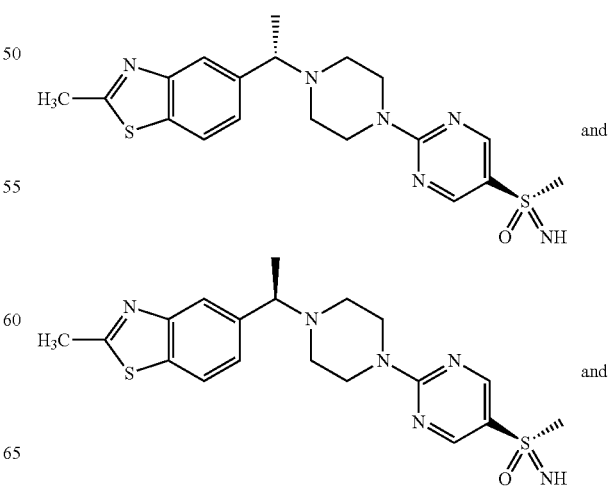

-continued

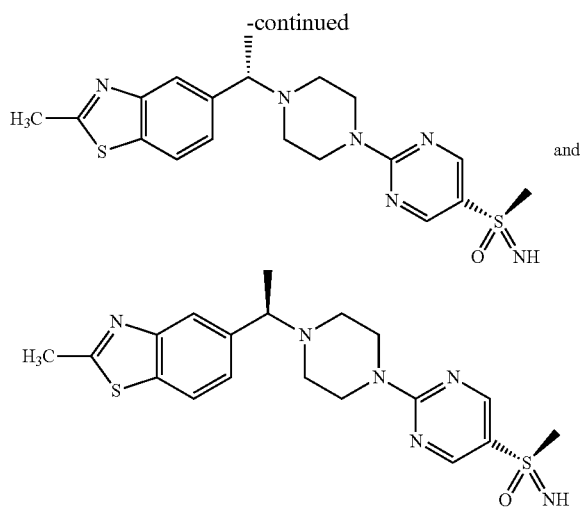

To a stirred solution of intermediate 8 (1.10 g, 4.20 mmol) in ACN (11 mL), TEA (1.6 mL, 11.5 mmol) and intermediate 10 (1.10 g, 4.00 mmol) were added and RT and the resulting mixture was stirred overnight. After completion of the reaction (monitored by TLC), the resulting mixture was concentrated under vacuum. The resulting crude material was purified by flash chromatography (Biotage Isolera, eluent: 90-95% EtOAc in pet ether) to afford the pure intermediate 2,2,2-trifluoro-N-(methyl(2-(4-(1-(2-methyl-benzo[d]thiazol-5-yl)ethyl)piperazin-1-yl)pyrimidin-5-yl)(oxo)-$\lambda^6$-sulfanylidene)acetamide. Yield: 61% (1.2 g, off white solid).

To this intermediate, methanol (2.5 mL) and $K_2CO_3$ (500 mg, 0.3.1 mmol) were added and stirred for 15 min. After 15 min, the reaction mixture was filtered through celite and concentrated under vacuum. The resulting crude material was purified by flash chromatography (Biotage Isolera, eluent: 3-4% methanol in DCM) to afford the tittle compound as racemic form. The four enantiomers of this racemic compound were separated by SFC (Method I: Chiral purification mobile phase: 40% 20 mM ammonia in IPA, column: LUX A1, flow rate: 4.0 mL).

Analysis of the first eluting fraction (example 51); Yield: 12% (55 mg, off white solid). $^1$H NMR (400 MHz, DMSO-$d_6$): δ 8.65 (s, 2H), 7.97 (d, J=8.4 Hz, 1H), 7.84 (s, 1H), 7.39 (d, J=8.0 Hz, 1H), 4.23 (s, 1H), 3.85-3.84 (m, 4H), 3.66-3.64 (m, 1H), 3.07 (s, 3H), 2.79 (s, 3H), 2.50-2.43 (m, 4H), 1.39 (d, J=6.8 Hz, 3H). LCMS: (Method A) 416.8 (M+H), Rt. 2.1 min, 99.4% (Max). HPLC: (Method A) Rt. 2.0 min, 99.7% (Max). Chiral SFC: (Method C) Rt. 3.8 min, 100% (Max).

Analysis of the second eluting fraction (example 52); Yield: 11% (46 mg, off white solid). $^1$H NMR (400 MHz, DMSO-$d_6$): δ 8.65 (s, 2H), 7.97 (d, J=8.4 Hz, 1H), 7.84 (s, 1H), 7.39 (d, J=8.0 Hz, 1H), 4.23 (s, 1H), 3.85-3.84 (m, 4H), 3.66-3.64 (m, 1H), 3.07 (s, 3H), 2.79 (s, 3H), 2.50-2.43 (m, 4H), 1.39 (d, J=6.80 Hz, 3H). LCMS: (Method A) 416.8 (M+H), Rt. 2.1 min, 99.2% (Max). HPLC: (Method A) Rt. 2.0 min, 99.7% (Max). Chiral SFC: (Method C) Rt. 4.5 min, 97.6% (Max).

Analysis of the third eluting fraction (example 53); Yield: 15% (65 mg, off white solid). $^1$H NMR (400 MHz, DMSO-$d_6$): δ 8.65 (s, 2H), 7.97 (d, J=8.4 Hz, 1H), 7.84 (s, 1H), 7.39 (d, J=8.0 Hz, 1H), 4.23 (s, 1H), 3.85-3.84 (m, 4H), 3.66-3.64 (m, 1H), 3.07 (s, 3H), 2.79 (s, 3H), 2.50-2.43 (m, 4H), 1.39 (d, J=6.80 Hz, 3H). LCMS: (Method A) 416.8 (M+H), Rt. 2.1 min, 99.4% (Max). HPLC: (Method A) Rt. 2.0 min, 99.4% (Max). Chiral SFC: (Method C) Rt. 4.9 min, 97.4% (Max).

Analysis of the fourth eluting fraction (example 54); Yield: 17% (75 mg, off white solid). $^1$H NMR (400 MHz, DMSO-$d_6$): δ 8.65 (s, 2H), 7.97 (d, J=8.4 Hz, 1H), 7.84 (s, 1H), 7.39 (d, J=8.0 Hz, 1H), 4.23 (s, 1H), 3.85-3.84 (m, 4H), 3.66-3.64 (m, 1H), 3.07 (s, 3H), 2.79 (s, 3H), 2.50-2.43 (m, 4H), 1.39 (d, J=6.80 Hz, 3H). LCMS: (Method A) 416.8 (M+H), Rt. 2.1 min, 98.2% (Max). HPLC: (Method A) Rt. 2.0 min, 97.9% (Max). Chiral SFC: (Method C) Rt. 8.5 min, 98.9% (Max).

Example B01: Pharmaceutical Preparations (A) Injection vials: A solution of 100 g of an active ingredient according to the invention and 5 g of disodium hydrogen phosphate in 3 l of bi-distilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

(B) Suppositories: A mixture of 20 g of an active ingredient according to the invention was melted with 100 g of soy lecithin and 1400 g of cocoa butter, poured into moulds and allowed to cool. Each suppository contained 20 mg of active ingredient.

(C) Solution: A solution was prepared from 1 g of an active ingredient according to the invention, 9.38 g of $NaH_2PO_4$ $2H_2O$, 28.48 g of $Na_2HPO_4$ $12H_2O$ and 0.1 g of benzalkonium chloride in 940 ml of bi-distilled water. The pH was adjusted to 6.8, and the solution was made up to 1 l and sterilized by irradiation. This solution could be used in the form of eye drops.

(D) Ointment: 500 mg of an active ingredient according to the invention were mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient.

(F) Coated tablets: Tablets were pressed analogously to (E) and subsequently coated in a conventional manner with a coating of sucrose, potato starch, talc, tragacanth and dye.

(G) Capsules: 2 kg of an active ingredient according to the invention were introduced into hard gelatin capsules in a conventional manner in such a way that each capsule contained 20 mg of the active ingredient.

(H) Ampoules: A solution of 1 kg of an active ingredient according to the invention in 60 l of bi-distilled water was sterile filtered, transferred into ampoules, lyophilized under sterile conditions and sealed under sterile conditions. Each ampoule contained 10 mg of active ingredient.

(I) Inhalation spray: 14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

Example C01: Physical Properties Characterization Methods

X-ray Powder Diffraction (XRPD)

Approximately 5-10 mg of sample was gently compressed on the XRPD zero back ground single obliquely cut silica sample holder. The sample was then loaded into a Philips X-Pert PRO diffractometer and analysed using the following experimental conditions.
Tube anode: Cu
Generator tension: 40 kV
Tube current: 40 mA
Wavelength alpha1: 1.5406 Å
Wavelength alpha2: 1.5444 Å
Start angle [2 theta]: 5
End angle [2 theta]: 50
Continuous scan
For suspected novel salts a slower scan speed was also used over a range of 4-40° 2θ.
Raman Spectroscopy
Samples were analysed by a Nicolet Almega DXR Dispersive Raman Microscope for its Raman spectrum using the following conditions:
Exposure Time: 1.0 s
Acquisition No: 10
Spectrograph Aperture: 50 μm pinhole
Grating: 600 lines/mm
Laser: He-Ne 633 nm 100% power
Then the measured Raman spectra were corrected by baseline subtraction using the software OMNIC™ v 9.
Nuclear Magnetic Resonance (NMR)
The compounds were dissolved in deuterated DMSO at the concentration of 7 mg/mL. The $^1$H NMR spectra were obtained by Bruker Avance 400 (Bruker, Coventry, UK). The FID files were processed by NMR software MestReNova V8.0. The chemical shifts and integrals of the peaks were analysed.
Simultaneous Thermal Analysis (STA)
Approximately 5 mg of sample was accurately weighed into a ceramic crucible and it was placed into the chamber of Perkin-Elmer STA 6000 TGA/DTA analyzer at ambient temperature. The sample was then heated at a rate of 10° C./min, typically from 30° C. to 300° C., during which time the change in weight was monitored as well as DTA signal. The purge gas used was nitrogen at a flow rate of 20 cm$^3$/min.
Gravimetric Vapour Sorption (GVS)
Approximately 10 mg of sample was placed into a wire-mesh vapour sorption balance pan and loaded into an 'IgaSorp' vapour sorption balance (Hiden Analytical Instruments). The sample was then dried by maintaining a 0% humidity environment until no further weight change was recorded. Subsequently, the sample was then subjected to a ramping profile from 0-90% RH at 10% RH increments, maintaining the sample at each step until equilibration had been attained (99% step completion). Upon reaching equilibration, the % RH within the apparatus was ramped to the next step and the equilibration procedure repeated. After completion of the sorption cycle, the sample was then dried using the same procedure. The adsorption/desorption cycle was generally repeated a second time in case the sample had changed during the first cycle. The weight change during the sorption/desorption cycles were then monitored, allowing for the hygroscopic nature of the sample to be determined.

Example C02: Method of Preparation of Succinate Salt of Example 35

A preferred method of preparation of the succinate salt was as follows:
A compound of Example 35 (3.0 g) and succinic acid (0.97 g) were weighed out into a 20 mL glass vial and ethanol (10 mL) was added to the physical solid mixture. The resulting suspension was heated until a clear solution was obtained which was then temperature-cycled between 40° C. and ambient temperature over 18 hours overnight. During this time crystals were precipitated and had amassed. More ethanol (2 mL) was added to mobilise and the product was filtered at ambient temperature, washed with ethanol (2×5 mL) and dried in a vacuum oven at 50° C. for 24 hours to constant weight. (Yield 3.1 g).

Example C03: Visual Aqueous Solubility

The succinate salt was weighed into glass vials and water was added in 100 μL portions up to 1 mL then 0.5 mL portions thereafter. The succinate salt had good solubility, completely dissolving in 0.8 mL water (>12.5 mg/mL).
Characterizing data for the succinate salt is summarized below:
The XRPD pattern is shown on FIG. 1
The NMR data was consistent with a stoichiometric mono-salt (FIG. 2).
STA showed no weight loss leading up to the melt with onset at ~125.5° C. The sample was not hydrated or solvated (FIG. 3).
GVS indicated the sample was only slightly hygroscopic with a reversible weight gain of 1.8% to 80% RH.
There was no change in XRPD following water slurry at 10 mg/200 μL.
There was no change in the X-ray pattern following slurry in IPA/water.
This salt had very good aqueous solubility estimated visually at ~12.5 mg/mL
It has no evidence of a tendency to form hydrates
These combined observations would make the succinate salt of compound of Example 35 a suitable candidate for further study and development Example C04: Fumarate Salt of a Compound of Example 35

A compound of Example 35 (300 mg) was warmed in ethanol (2 mL) in order to dissolve the solid. Fumaric acid (95 mg) was added to the warm solution and the mixture was stirred efficiently. More ethanol (1 ML) was added. A clear solution was observed initially but a solid was gradually precipitated as the mixture cooled to ambient temperature. The resulting suspension was temperature-cycled between 40° C. and ambient temperature overnight (18-24 hours). The product was filtered, washed with ethanol (2×1 mL) and dried in a vacuum oven at 45° C. to constant weight (Yield 350 mg, 91%).

Example C05: Visual Aqueous Solubility

The fumarate salt was weighed into glass vials and water was added in 100 μL portions up to 1 mL then 0.5 mL portions thereafter. The fumarate was completely dissolving in 3 mL water (>3.3 mg/mL).
Characterizing data for the fumarate salt is summarized below:
The XRPD pattern is shown in FIG. 4. No polymorphic form has been found.
The NMR data was consistent with a stoichiometric mono-salt (FIG. 5).
STA showed no weight loss leading up to the melt with onset at ~169° C. The sample was not hydrated or solvated (FIG. 6).

GVS indicated the sample was only slightly hygroscopic with a reversible marginal weight gain of 2.1% to 80% RH.

There was no change in XRPD following water slurry at 10 mg/200 μL.

There was no change in the X-ray pattern following slurry in IPA/water

The aqueous solubility of the fumarate was measured at ~3.3 mg/mL.

Example C06: Comparative Examples

Comparative Example C06-1: Succinate Salt Form 2 Preparation of a Compound of Example 35

The succinate of Example 35 (200 mg) prepared in example C02 (form 1) was suspended in 2-propanol (2 mL) and heated to dissolve. A few crystals obtained after slow crystallisation form 2-propanol or tetrahydrofuran were added to the warm solution and crystals were precipitated as the mixture cooled to ambient temperature. Excess solvent was allowed to evaporate under nitrogen flow and the product was further dried at 50° C. under vacuum for ~24 hours to constant weight.

The XRPD pattern is shown in FIG. 7

The NMR data was consistent with a stoichiometric mono-salt (FIG. 8).

GVS indicated the sample was slightly hygroscopic with a reversible weight gain of 1.25% to 80% RH. Also, there was a partial conversion to Form 1 evident in the X-ray pattern, obtained post GVS. This demonstrates the thermodynamic instablility of Form 2.

Slurries with Form 1 and Form 2 of the respective salt in ethanol, 90/10 2-propanol/water, 2-propanol and tetrahydrofuran all resulted in complete conversion to Form 1 at ambient temperature and at 40° C. This again demonstrates the thermodynamic instablility of Form 2.

Thus, Form 2 would not meet current regulatory requirements for drug development.

Comparative Example C06-2: Hydrochloride Salt Preparation of a Compound of Example 35

A compound of Example 35 (300 mg) was warmed in acetone (3 mL) so that the solid dissolved. Hydrochloric acid (5.825 M, 135 μL), prepared by diluting concentrated acid by two, was added to the warm solution and mixed well. An oil separated initially which was scratched using a spatula resulting in the product solidifying within 5-10 minutes. The resulting suspension was temperature-cycled between 40° C. and ambient temperature overnight (18-24 hours). The product was filtered, washed with acetone (2×1 mL) and dried in a vacuum oven at 45° C. for to constant weight. (Yield 194 mg, 57%).

Characterizing data for the hydrochloride salt are summarized below:

The XRPD pattern is shown in FIG. 9.

STA showed a weight loss of ~3.6% between 50° C. and 150° C. This was consistent with the theoretical value for a hydrated version of the salt (FIG. 10).

GVS also indicated the sample was clearly hygroscopic with a reversible weight gain of 3.6% to 70% RH and 4% to 80% RH.

The salt turned into an oily matter following suspension in water.

Due to the above negative properties, this hydrochloride salt would not meet current regulatory requirements for drug development.

Comparative Example C06-3: Benzoate Salt of a Compound of Example 35

A compound of Example 35 (300 mg) was heated to reflux in acetone (2 mL). Although the solid did not dissolve completely, benzoic acid (100 mg) was added to the warm mixture, and more acetone (1 mL) was added. The mixture was heated again to reflux and a clear solution was obtained. This solution was temperature-cycled between 40° C. and ambient temperature overnight (18 hours), but remained clear. Approximately half the volume of solvent was allowed to evaporate and a solid separated over ~24 hours. The product was filtered, washed with acetone (2×1 mL) and dried in a vacuum oven at 45° C. to constant weight. (Yield 290 mg, 74%).

Characterizing data for the benzoate salt is summarized below:

The XRPD pattern is shown in FIG. 11.

The NMR data was consistent with a stoichiometric mono-salt (FIG. 12).

There was a change in XRPD following slurry in water and in IPA/water, indicating that the polymorphic form of this salt is not thermodynamic stable, and therefore not suitable for a pharmaceutical development.

Comparative Example C06-4: Mesylate Salt of a Compound of Example 35

A compound of Example 35 (300 mg) was warmed in acetone (3 mL) so that the solid dissolved. Methane sulphonic acid (27μ) was added to a warm mixture resulting in the initial formation of an oily agglomerate. The mixture was ultrasonicated for about 1 minute and some solid appeared to separate. The mixture was temperature-cycled between 40° C. and ambient temperature overnight (18 hours) and about half of the volume of solvent was allowed to evaporate. A solid product resulted which was filtered and dried in a vacuum oven at 45° C. to constant weight (Yield 95 mg).

Characterizing data for the mesylate salt is summarized below:

The X-ray pattern for the product was consistent with a mixture of the parent free base and amorphous salt, indicating that the mesylate salt cannot be reproducibly isolated as a solid form. Thus, the mesylate salt of Example 35 is not suitable for pharmaceutical development.

Comparative Example C06-5: Comparative Visual Aqueous Solubility with the Free Base of Example 35

The free base Example 35 (10 mg) was weighed into glass vials and water was added in 100 μL portions up to 1 mL then 0.5 mL portions thereafter. Solubility was assessed visually following a brief period of equilibration. The free base did not give any indication it was soluble at all in 8 mL water (<<1.25 mg/mL).

Salts of compounds of formula I with various acids other than succinic acid and fumaric acid did not yield a suitable pharmaceutical properties i.e. have not been soluble, stable or solid or have other properties not suitable for pharma-

The invention claimed is:
1. A mono-succinic acid salt of compound Ia,
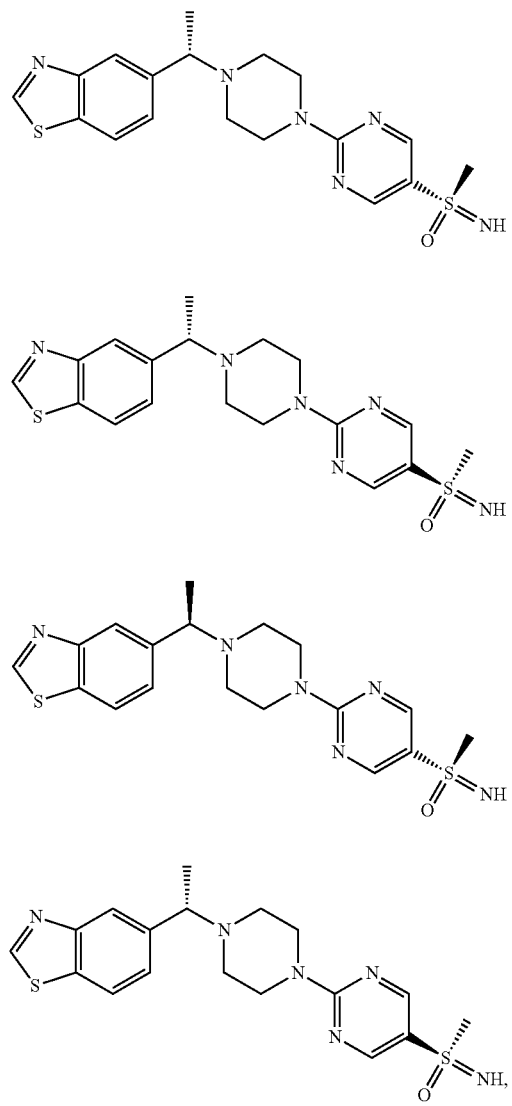
wherein the salt is in a solid form having the characteristic X-ray powder diffraction pattern as shown on FIG. 1.
2. A mono-fumaric acid salt of compound Ia,
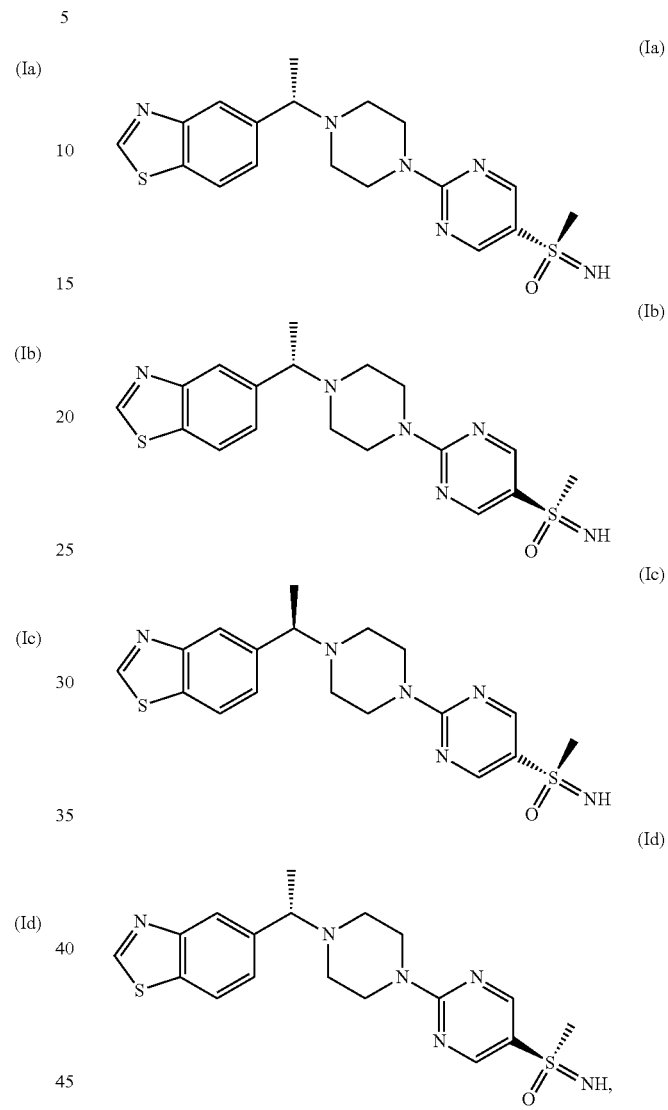
wherein the salt is in a solid form having the characteristic X-ray powder diffraction pattern as shown on FIG. 4.
* * * * *